(12) United States Patent
O'Hagan et al.

(10) Patent No.: US 10,485,761 B2
(45) Date of Patent: Nov. 26, 2019

(54) IRRADIATED BIODEGRADABLE POLYMER MICROPARTICLES

(71) Applicant: GLAXOSMITHKLINE BIOLOGICALS, SA, Rixensart (BE)

(72) Inventors: Derek O'Hagan, Winchester, MA (US); Manmohan Singh, Cary, NC (US); Siddhartha Jain, Troy, NY (US); Padma Malyala, Acton, MA (US)

(73) Assignee: GLAXOSMITHKLINE BIOLOGICALS, S.A., Rixensart (BE)

( * ) Notice: Subject to any disclaimer, the term of this patent is extended or adjusted under 35 U.S.C. 154(b) by 0 days.

(21) Appl. No.: 15/981,104

(22) Filed: May 16, 2018

(65) Prior Publication Data

US 2018/0280301 A1    Oct. 4, 2018

Related U.S. Application Data

(63) Continuation of application No. 13/574,958, filed as application No. PCT/US2011/022257 on Jan. 24, 2011, now abandoned.
(Continued)

(51) Int. Cl.
*A61K 9/14*        (2006.01)
*A61K 39/00*      (2006.01)
(Continued)

(52) U.S. Cl.
CPC ...... *A61K 9/14* (2013.01); *A61J 1/00* (2013.01); *A61K 39/00* (2013.01); *A61K 39/095* (2013.01); *A61K 2039/55555* (2013.01)

(58) Field of Classification Search
CPC . A61J 1/00; A61K 2039/55555; A61K 39/00; A61K 39/095; A61K 9/14; A61K 2300/00; A61K 39/39; A61K 31/4745; A61K 31/7115; A61K 33/06; A61K 39/12; A61K 45/06; A61K 2039/55561; A61K 9/1647; A61K 2039/6093; A61K 9/5153; A61K 2039/555; A61K 31/7088; A61K 39/0011; A61K 39/385; A61K 2039/541; A61K 2039/55511; A61K 47/593; A61K 2039/55522; A61K 31/337; A61K 39/35; A61K 9/0019; A61K 2039/54; A61K 2039/542; A61K 2039/543; A61K 31/70; A61K 39/0005; A61K 39/0013; A61K 47/58; A61K 47/6921; A61K 47/6929;
(Continued)

(56) References Cited

U.S. PATENT DOCUMENTS

| | | | | |
|---|---|---|---|---|
| 5,650,173 A | * | 7/1997 | Ramstack et al. | 424/489 |
| 5,770,559 A | * | 6/1998 | Manning et al. | 424/489 |

(Continued)

OTHER PUBLICATIONS

Puthli et al. AAPS PharmSciTech. Jun. 2009; 10(2): 443-452 (Year: 2009).*

*Primary Examiner* — Janet L Epps-Smith
(74) *Attorney, Agent, or Firm* — Birch, Stewart, Kolasch & Birch, LLP

(57) ABSTRACT

In one aspect, the present invention provides sterile microparticle compositions comprising biodegradable microparticles, which comprise at least one biodegradable polymer. In other aspects, the present invention provides methods of making and using such compositions as well as articles of manufacture and kits containing the same.

9 Claims, 1 Drawing Sheet

Related U.S. Application Data

(60) Provisional application No. 61/297,809, filed on Jan. 24, 2010.

(51) Int. Cl.
*A61K 39/095* (2006.01)
*A61J 1/00* (2006.01)

(58) Field of Classification Search
CPC ............ A61K 2039/70; A61K 39/0002; A61K 47/02; A61K 47/22; A61K 47/24; A61K 47/60; A61K 47/646; A61K 47/68; A61K 47/6931; A61K 2039/5154; A61K 2039/545; A61K 2039/55566; A61K 2039/60; A61K 31/74; A61K 39/002; A61K 39/21; A61K 47/6911; A61K 47/6937; A61K 9/1611; A61K 9/19; A61K 2039/5156; A61K 2039/53; A61K 2039/55516; A61K 31/00; A61K 38/20; A61K 38/21; A61K 39/0008; A61K 39/001; A61K 39/02; A61K 39/05; A61K 39/08; A61K 39/36; A61K 47/26; A61K 9/0021; A61K 9/0024; A61K 9/127; A61K 9/1641; A61K 9/1652; A61K 9/1676; A61K 9/5115; A61K 2039/515; A61K 2039/55505; A61K 2039/577; A61K 2039/6006; A61K 2039/605; A61K 2039/622; A61K 33/00; A61K 35/18; A61K 38/00; A61K 38/38; A61K 41/0004; A61K 41/0071; A61K 47/06; A61K 47/50; A61K 47/6901; A61K 47/6927; A61K 49/0002; A61K 9/10; A61K 9/1075; A61K 9/16; A61K 9/1635; A61K 9/167; A61K 9/1688; A61K 9/1694; A61K 9/5031; A61K 9/5084; A61K 9/5123; A61K 9/5146; A61K 2039/507; A61K 2039/5256; A61K 2039/55533; A61K 2039/55572; A61K 2039/55577; A61K 2039/55588; A61K 2039/57; A61K 2039/58; A61K 2039/585; A61K 2039/62; A61K 31/01; A61K 31/10; A61K 31/192; A61K 31/196; A61K 31/216; A61K 31/436; A61K 31/4422; A61K 31/4545; A61K 31/4709; A61K 31/496; A61K 31/58; A61K 31/745; A61K 31/765; A61K 31/78; A61K 38/02; A61K 38/13; A61K 38/16; A61K 38/1816; A61K 38/193; A61K 38/28; A61K 39/0001; A61K 39/0003; A61K 39/085; A61K 39/099; A61K 39/245; A61K 39/395; A61K 47/34; A61K 47/38; A61K 47/52; A61K 47/544; A61K 47/595; A61K 47/643; A61K 47/69; A61K 47/6915; A61K 47/6923; A61K 47/6939; A61K 49/1818; A61K 51/12; A61K 51/1244; A61K 9/00; A61K 9/007; A61K 9/0075; A61K 9/08; A61K 9/107; A61K 9/12; A61K 9/145; A61K 9/146; A61K 9/148; A61K 9/1617; A61K 9/1623; A61K 9/1664; A61K 9/5015; A61K 9/5057; A61K 9/51; A61K 9/5138; A61K 9/5192; A61K 9/7007; C08L 101/02; C08L 1/02; C08L 1/08; C08L 3/02; C08L 5/00; C08L 5/02; C08L 5/06; Y02A 50/466; Y02A 50/401; Y02A 50/386; Y02A 50/388; Y02A 50/39; Y02A 50/396; Y02A 50/403; Y02A 50/469; Y02A 50/478; Y02A 50/48; Y02A 50/484; Y02A 50/412; Y02A 50/464; Y02A 50/41; Y02A 50/394; Y02A 50/423; A61L 31/10; A61L 27/34; A61L 17/10; A61L 17/145; A61L 27/14; A61L 15/46; A61L 17/005; A61L 2300/404; A61L 2300/606; A61L 2400/12; A61L 27/12; A61L 27/36; A61L 27/38; A61L 27/48; A61L 27/54; A61L 27/58; A61L 29/16; A61L 31/048; A61L 31/129; A61L 31/148; A61L 31/16
USPC ............... 424/184.1, 489, 400, 450; 977/773
See application file for complete search history.

(56) References Cited

U.S. PATENT DOCUMENTS

| | | | |
|---|---|---|---|
| 6,228,423 B1* | 5/2001 | Sokoll et al. ............. | 427/213.3 |
| 7,893,096 B2* | 2/2011 | Valiante, Jr. .................. | 514/359 |
| 2005/0079138 A1* | 4/2005 | Chickering et al. ........... | 424/46 |
| 2005/0271591 A1* | 12/2005 | Walovitch ............ | A61K 49/223 |
| | | | 424/9.5 |
| 2008/0131466 A1* | 6/2008 | Reed et al. ................ | 424/282.1 |
| 2011/0280949 A1* | 11/2011 | Malyala .................. | A61K 9/19 |
| | | | 424/501 |

* cited by examiner

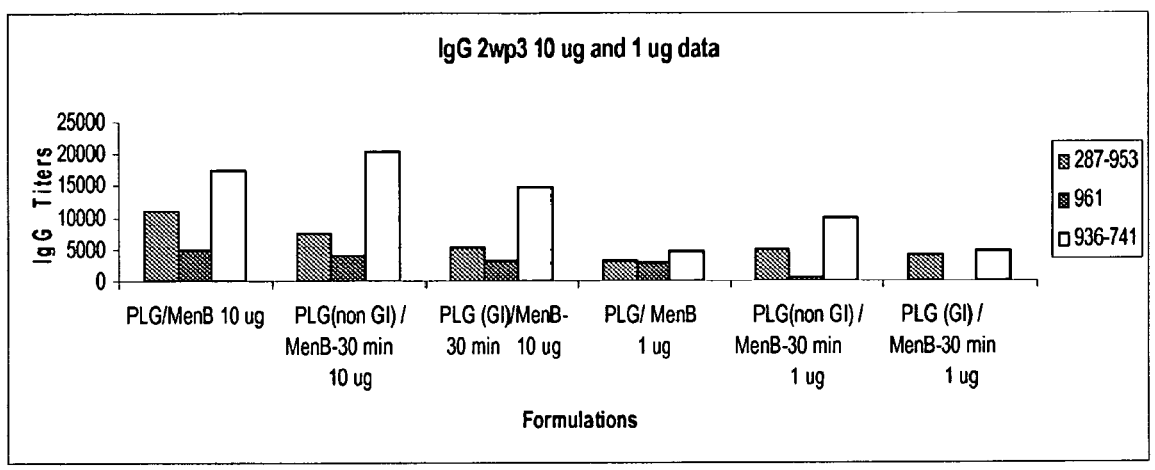

IRRADIATED BIODEGRADABLE POLYMER MICROPARTICLES

RELATED APPLICATION

This application is a Continuation of U.S. application Ser. No. 13/574,958, filed Jan. 6, 2013, which is the U.S. National Phase of International Application Number PCT/US2011/022257, filed Jan. 24, 2011 and published in English, which claims priority from U.S. provisional application No. 61/297,805, filed Jan. 24, 2010, which is incorporated by reference herein in their entirety.

BACKGROUND

Particulate carriers have been used with adsorbed or entrapped antigens in attempts to elicit adequate immune responses. Such carriers present multiple copies of a selected antigen to the immune system and are believed to promote trapping and retention of antigens in local lymph nodes. The particles can be phagocytosed by macrophages and can enhance antigen presentation through cytokine release.

For example, commonly owned International Publication No. WO 98/33487 and co-pending U.S. Patent Application Publication No. 2003/0049298 describe the use of antigen-adsorbed and antigen-encapsulated microparticles to stimulate immunological responses, including cell-mediated immunological responses, as well as methods of making the microparticles. Polymers that may be used to form the microparticles include poly(lactide) and poly(lactide-co-glycolide) (PLG).

Commonly owned International Publication No. WO 00/06123 and WO 01/36599 and U.S. Pat. No. 6,884,435 disclose methods of making microparticles having adsorbed macromolecules, including polynucleotides and polypeptide antigens. The microparticles comprise, for example, a polymer such as a poly(alpha-hydroxy acid) (e.g., PLGA, a polyhydroxy butyric acid, a polycaprolactone, a polyorthoester, a polyanhydride, and the like) and are formed using, for example, cationic, anionic or nonionic detergents. Microparticles containing anionic detergents, such as PLG microparticles containing sodium dodecyl sulfate (SDS), can be used with positively charged macromolecules, such as polypeptides. Microparticles containing cationic detergents, such as PLG microparticles with CTAB (also known as cetrimide or cetyl trimethyl ammonium bromide), can be used with negatively charged macromolecules, such as DNA. The use of such microparticles to stimulate immunological responses, including cell-mediated immunological responses, is also disclosed.

SUMMARY OF THE INVENTION

The present invention provides sterile microparticle compositions comprising biodegradable microparticles, which comprise at least one biodegradable polymer.

In certain embodiments, the sterile microparticle compositions are dry.

In certain embodiments, the microparticle compositions are blank (i.e., they are free of active agents such as pharmaceuticals including drugs, immunological adjuvants, antigens, etc.).

In certain embodiments, the biodegradable polymers within the sterile microparticle compositions of the invention are synthetic biodegradable polymers, for example, selected from polyesters (e.g., poly[hydroxy acids], poly [cyclic esters], etc.), polycarbonates, polyorthoesters, polyanhydrides, polycyanoacrylates, polyphosphazines, and combinations thereof, among others.

In certain embodiments, the sterile microparticle compositions are gamma irradiated. By gamma irradiating the microparticle compositions in a sealed environment after their preparation, it is possible to provide a sterile product, even where the microparticle compositions have been manufactured under aseptic conditions.

Sterile microparticle compositions in accordance with the invention may be provided, for example, within a sealed container that is configured to allow for the introduction and removal of sterile fluid (e.g., within a glass vial having a rubber septum, etc.).

By providing sterile dry microparticle compositions within such a sealed container, the microparticles may be exposed to an aqueous fluid (e.g., Water for Injection), thereby forming an aqueous suspension of the microparticles, which can subsequently be withdrawn and administered to a patient.

Preferably, upon the addition of water in an amount such that the microparticle composition is present in a concentration of 25 mg/ml, a suspension is formed in which the suspended microparticles have a D(v,0.5) value that is less than 10 μm, for example ranging from 10 μm to 5 m to 2.5 μm to 1 μm to 500 nm to 250 nm to 100 nm or less.

In certain embodiments, such a sealed container may be provided along with a label indicating one or more members of the group consisting of the following: (a) a statement that the microparticle formulation has been gamma-irradiated, (b) storage information, (c) dosing information, and (d) instructions regarding how to administer the microparticle formation. In some instances, the sealed container and label may be contained within a suitable packaging material.

In certain embodiments, the microparticle compositions in accordance with the present invention comprise antigens. Examples of antigens include peptide-containing antigens, polysaccharide-containing antigens, polynucleotide-containing antigens, and hybrids of the same (e.g., peptide-polysaccharide hybrid antigens), among others. Antigens can be derived from, for example, from tumor cells and from pathogenic organisms such as viruses, bacteria, fungi and parasites.

Where the microparticle compositions are sterilized by gamma irradiation and where an antigen is resistant to the effects of such radiation, the antigen may be, for example, associated with the surface of the microparticles (e.g., adsorbed), entrapped or encapsulated within the microparticles, or both.

Many antigens, however, are not resistant to the effects of such irradiation, in which case the antigens may be combined with the microparticles after radiation sterilization. For example, a sterile aqueous antigen-containing fluid (e.g., solution, suspension, etc.) may be introduced to the microparticle compositions of the invention (which may be, for example, in dry form, in an aqueous suspension, etc.), thereby forming a sterile aqueous suspension containing the microparticles and antigen, which can subsequently be withdrawn and administered to a patient. In some of these embodiments, a substantial percentage of the antigen (e.g., 25 wt % or more) becomes adsorbed to the microparticles within a short period of time (e.g., 30 minutes or less), for example, from 25 wt % to 50 wt % to 75 wt % to 90 wt % to 95 wt % or more of the antigen may become adsorbed to the microparticles, preferably within a period ranging from 30 minutes to 10 minutes to 5 minutes to 1 minute or less.

In certain embodiments (e.g., where the antigen to be administered is a peptide-containing antigen), microparticles having a net negative charge may be employed to enhance adsorption. In certain other embodiments (e.g., where the antigen to be administered is a polynucleotide-containing antigen), microparticles having a net positive charge may be employed to enhance adsorption.

The net charge of a given microparticle population may be measured using known techniques including measurement of the microparticle zeta potential. In certain embodiments, upon the addition of water in an amount such that the microparticle composition is present in a concentration of 25 mg/ml, a suspension is formed in which the suspended microparticles have a zeta potential that is greater than +20 mV (for positively charged particles) or less than −20 mV (for negatively charged particles) at physiological pH.

In certain embodiments the microparticles are formed using a charged biodegradable polymer. In certain embodiments, microparticles are formed in the presence of a charged species or subsequently treated with a charged species. Examples of such charged species include ionic small molecules, ionic peptides, ionic polymers and ionic surfactants, among others.

In certain embodiments, the sterile microparticle compositions of the invention comprise cryoprotective agents. Such agents are particularly desirable, for instance, where sterile dry microparticle compositions are formed using a freeze-drying process (e.g., lyophilization).

Examples of cryoprotective agents include polyols, carbohydrates and combinations thereof, among others.

In certain embodiments, microparticle compositions in accordance with the present invention comprise immunological adjuvants. Examples of immunological adjuvants include CpG oligonucleotides, double-stranded RNA, E. coli heat-labile toxins, aluminium salts, liposaccharide phosphate compounds, liposaccharide phosphate mimetics, monophosphoryl lipid A analogues, small molecule immune potentiators (such as TLR agonists, including benzonaphthyridine compounds, lipopeptides, etc.), muramyl tripeptide phosphatidylethanolamine and tocopherols among others.

Where the microparticles are sterilized by gamma irradiation and where the immunological adjuvants are resistant to the effects of such radiation, the immunological adjuvants may be, for example, associated with the surface of the microparticles (e.g., adsorbed or otherwise bound), entrapped or encapsulated within the microparticles, or both.

Where immunological adjuvants are not resistant to the effects of such radiation, the immunological adjuvants may be combined with the microparticles after radiation sterilization. For example, a sterile antigen-containing solution or suspension may be introduced to the microparticles (which may be, for example, in dry form, in an aqueous suspension, etc.), thereby forming a sterile aqueous suspension containing the microparticles and adjuvant. In certain embodiments, a substantial percentage of the immunological adjuvant (e.g., 25 wt % or more) becomes adsorbed to the microparticles within a short period of time (e.g., 30 minutes or less), for example, from 25 wt % to 50 wt % to 75 wt % to 90 wt % to 95 wt % or more of the immunological adjuvant may become adsorbed to the microparticles within a period ranging from 30 minutes to 10 minutes to 5 minutes to 1 minute or less.

In certain embodiments, the microparticle compositions in accordance with the present invention comprise a small molecule immune potentiator resistant to the effects of gamma irradiation, entrapped or encapsulated within the microparticles. After gamma irradiation, an antigen is adsorbed to the surface of the microparticles with encapsulated small molecule immune potentiators. In certain embodiments, the small molecule immune potentiator is a TLR7 agonist (e.g., a benzonaphthyridine compound). In other embodiments, the small molecule immune potentiator is a TLR2 agonist (e.g., a lipopeptide). In certain embodiments, the microparticle compositions of the invention comprise both a TLR7 and a TLR2 agonist, encapsulated within the microparticles.

In certain embodiments, the microparticle compositions in accordance with the present invention comprise therapeutic agents or other charged drugs. Where the microparticles are sterilized by gamma irradiation and where a therapeutic agent, or a charged drug, is resistant to the effects of such radiation, the therapeutic agent, or charged drug as the case may be, may be, for example, associated with the surface of the microparticles (e.g., adsorbed or otherwise bound), entrapped or encapsulated within the microparticles, or both. Where a therapeutic agent, or a charged drug, is not resistant to the effects of such radiation, the therapeutic agent or charged drug is combined with the microparticles after radiation sterilization.

Other aspects of the present invention pertain to kits that contain microparticle compositions in accordance with the invention. For example, in certain embodiments, a kit is provided which comprises: (a) a first sealed container that contains a sterile dry microparticle composition as described herein, (b) an additional sealed container that contains one or more sterile vaccine antigens (e.g. in dry form, in the form of a sterile solution/suspension, etc.) and/or (c) an additional sealed container that contains one or more sterile immunological adjuvants (e.g. in dry form, in the form of a sterile solution/suspension, etc.). In certain embodiments, a kit is provided which comprises: (a) a first sealed container that contains a sterile dry microparticle composition as described herein, (b) an additional sealed container that contains one or more sterile therapeutic agents (e.g. in dry form, in the form of a sterile solution/suspension, etc.) and/or (c) an additional sealed container that contains one or more sterile pharmaceutically acceptable carrier.

The first sealed container and the one or more additional sealed containers are configured to allow the introduction and removal of sterile fluid (e.g., via a rubber septum, etc.). Such kits may be provided with labeling and/or packaging as described above.

In other aspects, the present invention provides methods of producing microparticle compositions such as the foregoing.

In still other aspects, the present invention provides methods of delivering the microparticle compositions to a host subject (e.g., for therapeutic, prophylactic, or diagnostic purposes). The host animal is preferably a vertebrate animal, more preferably a mammal, and even more preferably a human.

In certain embodiments, methods of delivering the microparticle compositions to a host subject are provided, which comprise (a) combining sterile dry biodegradable polymer microparticles with an aqueous fluid containing one or more antigens, thereby adsorbing at least a portion of the antigen on surface of the microparticles and (b) administering the combination to a mammal, preferably within 30 minutes of mixing, more preferably within 10 minutes of mixing, even more preferably as soon as is convenient, after mixing.

These and other aspects, embodiments, and advantages of the present invention will become more readily apparent to those of ordinary skill in the art in view of the disclosure herein.

BRIEF DESCRIPTION OF THE DRAWINGS

FIG. 1 is a bar graph illustrating ELISA antibody titers in mice at 1 and 10 µg dosages for three Men antigens (287-953, 961 and 936-741) for the following (a) Men overnight adsorption on non-gamma-irradiated PLG and lyophilization, (b) Men 30 minute adsorption on non-gamma-irradiated PLG, and (c) Men 30 minute adsorption on gamma-irradiated PLG.

DETAILED DESCRIPTION OF THE INVENTION

1. Microparticles

The present invention provides sterile microparticle compositions comprising biodegradable microparticles that comprise at least one biodegradable polymer. In certain embodiments, the sterile microparticle compositions are dry and/or blank.

Useful biodegradable polymers for forming the microparticles of the invention include homopolymers, copolymers and polymer blends, both natural and synthetic. Such polymers may be derived, for example, from the following: polyesters (e.g., polyhydroxy acids, polycaprolactones, etc.), polycarbonates, polyorthoesters, polyanhydrides, polycyanoacrylates (e.g., polyalkylcyanoacrylate or "PACA"), polyphosphazines, and combinations thereof. More typical are polyesters, for example, homopolymers and copolymers of glycolic acid, L-lactic acid, D,L-lactic acid, hydroxybutyric acid, hydroxyvaleric acid, caprolactone and dioxanone, among others. Even more typical are homopolymers and copolymers of L-lactide, D,L-lactide, and glycolide, for example, polyglycolide, polylactide, for example, poly(L-lactide) or poly(D,L-lactide) (referred to as PLA herein) and poly(lactide-co-glycolide), for example, poly(L-lactide-co-glycolide) and poly(D,L-lactide-co-glycolide) (designated as "PLG" or "PLGA" herein).

The above polymers are available in a variety of molecular weights, and a suitable molecular weight for a given use is readily determined by one of skill in the art. Thus, for example, a suitable molecular weight for PLA may be on the order of about 2,000 to 5,000. A suitable molecular weight for PLG may range from about 5,000 to about 200,000.

Where copolymers are employed, copolymers with a variety of monomer ratios may be available. For example, where PLG is used to form the microparticles, a variety of lactide:glycolide molar ratios will find use herein, and the ratio is largely a matter of choice, depending in part on any coadministered adsorbed and/or entrapped species and the rate of degradation desired. For example, a 50:50 PLG polymer, containing 50% D,L-lactide and 50% glycolide, will provide a faster resorbing copolymer, while 75:25 PLG degrades more slowly, and 85:15 and 90:10, even more slowly, due to the increased lactide component. Mixtures of microparticles with varying lactide:glycolide ratios may also find use herein in order to achieve the desired release kinetics. Degradation rate of the microparticles of the present invention can also be controlled by such factors as polymer molecular weight and polymer crystallinity.

Where used, PLG copolymers are typically those having a lactide/glycolide molar ratio ranging, for example, from 20:80 to 25:75 to 40:60 to 45:55 to 55:45 to 60:40 to 75:25 to 80:20, and having a molecular weight ranging, for example, from 5,000 to 10,000 to 20,000 to 40,000 to 50,000 to 70,000 to 100,000 to 200,000 Daltons, among others.

PLG copolymers with varying lactide:glycolide ratios, molecular weights and end groups are readily available commercially from a number of sources including from Boehringer Ingelheim, Germany, Birmingham Polymers, Inc., Birmingham, Ala., USA, DURECT Corporation, Pelham, Ala. and Lakeshore Biomaterials, Birmingham, Ala., USA. Some exemplary PLG copolymers, available from Boehringer Ingelheim, include: (a) RG 502, a PLG having predominantly alkyl ester end groups on one of the chain ends, a 50:50 lactide/glycolide molar ratio and a molecular weight of 12,000 Da, (b) RG 503, a PLG having predominantly alkyl ester end groups on one of the chain ends, a 50:50 lactide/glycolide molar ratio and a molecular weight of 34,000 Da, (c) RG 504, a PLG having predominantly alkyl ester end groups on one of the chain ends, a 50:50 lactide/glycolide molar ratio and a molecular weight of 48,000 Da, (d) RG 752, a PLG having predominantly alkyl ester end groups on one of the chain ends, a 75:25 lactide/glycolide molar ratio and a molecular weight of 22,000 Da, (e) RG 755, a PLG having predominantly alkyl ester end groups on one of the chain ends, a 75:25 lactide/glycolide molar ratio and a molecular weight of 68,000 Da, (f) RG 502H, a PLG having a 50:50 lactide/glycolide molar ratio, and having predominantly free carboxyl end groups on one of the chain ends, and (g) RG 503H, a PLG having a 50:50 lactide/glycolide molar ratio, and having predominantly free carboxyl end groups on one of the chain ends.

Microparticles in accordance with the invention can be prepared using any suitable method.

For example, in some embodiments, microparticles can be formed using spray-drying and coacervation as described in, e.g., Thomasin et al., *J. Controlled Release*, 41:131 (1996); U.S. Pat. No. 2,800,457; Masters, K. (1976) *Spray Drying* 2nd Ed. Wiley, New York; air-suspension coating techniques, such as pan coating and Wurster coating, as described by Hall et al., (1980) The "Wurster Process" in *Controlled Release Technologies: Methods, Theory, and Applications* (A. F. Kydonieus, ed.), Vol. 2, pp. 133-154 CRC Press, Boca Raton, Fla. and Deasy, P. B., *Crit. Rev. Ther. Drug Carrier Syst.* S(2):99-139 (1988); and ionic gelation as described by, e.g., Lim et al., *Science* 210:908-910 (1980).

More preferably microparticles may be formed using a water-in-oil-in-water (w/o/w) solvent evaporation process or using a nanoprecipitation method.

The w/o/w solvent evaporation process is described, for example, in O'Hagan et al., *Vaccine* 11:965-969 (1993), Jeffery et al., *Pharm. Res.* 10:362 (1993), and WO 00/06123 to O'Hagan et al. In general, a polymer of interest, such as PLG, is dissolved in an organic solvent, such as dimethylchloride (also called methylene chloride and dichloromethane), ethyl acetate, acetonitrile, acetone, chloroform, and the like. The polymer solution is then combined with a first volume of aqueous solution and emulsified to form an o/w emulsion. The aqueous solution can be, for example, deionized water, normal saline, a buffered solution, for example, phosphate-buffered saline (PBS) or a sodium citrate/ethylenediaminetetraacetic acid (sodium citrate/ETDA) buffer solution, among others. Typically, the volume ratio of polymer solution to aqueous solution ranges from about 5:1 to about 20:1, more typically about 10:1. Emulsification is conducted using any equipment appropriate for this task, and is typically a high-shear device such as, e.g., a homogenizer. A volume of the o/w emulsion is then combined with a larger second volume of an aqueous solution, which typically contains a surfactant, for instance, an uncharged surfactant (e.g., PVA (polyvinyl alcohol), povidone (also known as polyvinylpyrrolidone or PVP), sorbitan esters, polysorbates, polyoxyethylated glycol monoethers, polyoxyethylated alkyl phenols, or poloxamers, among others), a cationic surfactant (discussed below) or an anionic surfactant (discussed below). The volume ratio of aqueous solution to o/w emulsion typically ranges from about 2:1 to 10:1, more typically about 4:1. This mixture is then homogenized to produce a stable w/o/w double emulsion. Organic solvents are then evaporated to yield microparticles. Microparticles manufactured in the presence of charged surfactants, such as anionic or cationic surfactants, can yield microparticles with a surface having a net negative or a net positive charge, which can adsorb a wide variety of molecules. For example, microparticles manufactured with anionic surfactants, such as sodium dodecyl sulfate (SDS), e.g., SDS-PLG microparticles, may adsorb positively charged species, for example, polypeptide-containing species such as proteins. Similarly, microparticles manufactured with cationic surfactants, such as CTAB, e.g., PLG/CTAB microparticles, may adsorb negatively charged species, for example, polynucleotide-containing species such as DNA, RNA, DNA-RNA heteropolymers, or oligonucleotides.

The nanoprecipitation method, also referred to as the solvent displacement method, is another example of a suitable method for forming microparticles for use in the invention. See, e.g., European Patent No. 0274961B1 entitled "Process for the preparation of dispersible colloidal systems of a substance in the form of nanocapsules," Devissaguet et al., U.S. Pat. No. 5,049,322 by the same title, Fessi et al., U.S. Pat. No. 5,118,528, entitled "Process for the preparation of dispersible colloidal systems of a substance in the form of microparticles," and Wendorf et al., WO 2008/051245, entitled "Nanoparticles for use in Immunogenic compositions." In this technique, for instance, a polymer may be dissolved in an organic solvent (e.g., a hydrophilic organic solvent such as acetone, ethanol, etc.). The resulting organic solution may then be combined with a further solvent, which is miscible with the organic solvent while being a non-solvent for the polymer, typically an aqueous solution. The aqueous solution can be, for example, deionized water, normal saline, a buffered solution, such as for example, phosphate-buffered saline (PBS) or a sodium citrate/ethylenediaminetetraacetic acid (sodium citrate/EDTA) buffer solution. The organic solution and aqueous solution may then be combined in suitable relative volumes (e.g. typically from 1:2 to 2:1, more typically about 1:1). For example, the organic solution may be poured or injected into the non-solvent while stirring, or vice versa. By selecting a system in which the polymer is soluble in the organic solvent, while being significantly less soluble in the miscible blend of the organic solvent with the non-solvent, a suspension of microparticles may be formed virtually instantaneously. Subsequently, the organic solvent can be eliminated from the suspension, for example, by evaporation.

In some embodiments, it is desirable to provide one or more additional species (in addition to biodegradable polymer), which may be associated with the interior (e.g., entrapped) and/or surface (e.g. adsorbed) of the microparticles or may be non-associated with the microparticles. Such additional species can include, for instance, agents to adjust tonicity or pH, cryoprotective agents, microparticle charge inducing agents (e.g., charged surfactants, charged polymers, etc.), immunological adjuvants, antigens, and so forth.

Such additional species may be provided during the microparticle formation process, particularly where the additional species is not rendered inoperable by any subsequent sterilization processes (e.g., a gamma irradiation process). In the above described microparticle formation techniques (e.g., w/o/w solvent evaporation, nanoprecipitation, etc.), the organic and/or aqueous solutions employed can thus further contain various additional species as desired. For example, these additional species may be added (a) to an organic solution, if in oil-soluble or oil-dispersible form or (b) to an aqueous solution, if in water-soluble or water-dispersible form.

In other embodiments, one or more additional species may be added subsequent to microparticle formation (typically subsequent to organic solvent removal, as well as subsequent to washing steps, if any). These additional species are frequently added to the microparticles as an aqueous solution or dispersion. These species can, for instance, be in solution and/or accumulate at the particle-solution interface, for example, being adsorbed at the microparticle surface.

Once a suitable microparticle composition comprising microparticles is formed (e.g., using the above-described or other techniques), it may be lyophilized for future use.

In many embodiments, the microparticle composition is sterilized, for example, using a suitable sterilization process such as gamma irradiation. Such microparticle compositions may be sterilized, for example, after being loaded into a sealed container (e.g., a vial with a septum). Typical gamma irradiation dosages range, for example, from 10 to 30 kGy units.

2. Antigens

As noted above, microparticle compositions and kits in accordance with the invention may include one or more antigens, each antigen being provided in an effective amount (e.g., an amount effective for use in therapeutic, prophylactic, or diagnostic methods in accordance with the invention). For example, the compositions of the present invention may be used to treat or prevent diseases caused by any of the below-listed pathogens or tumors.

Antigens for use with the invention include, but are not limited to, one or more of the antigens set forth below, or antigens derived from one or more of the pathogens and tumors set forth below:

A. Bacterial Antigens

Bacterial antigens suitable for use in the invention include proteins, polysaccharides, lipopolysaccharides, and outer membrane vesicles which may be isolated, purified or derived from a bacterium. In addition, bacterial antigens include bacterial lysates and inactivated bacteria formulations. Bacteria antigens can be produced by recombinant expression. Bacterial antigens preferably include epitopes which are exposed on the surface of the bacteria during at least one stage of its life cycle. Bacterial antigens are preferably conserved across multiple serotypes. Bacterial antigens include antigens derived from one or more of the bacteria set forth below as well as the specific antigens examples identified below.

*Neisseria meningitides:* Meningitides antigens include proteins (such as those identified in WO99/24578; WO99/36544; WO99/57280; WO00/22430; Tettelin et al. (2000) *Science* 287:1809-1815; WO96/29412; and Pizza et al. (2000) *Science* 287:1816-1820), saccharides (including a polysaccharide, oligosaccharide or lipopolysaccharide), or outer-membrane vesicles (WO01/52885; Bjune et al. (1991) *Lancet* 338(8775): 1093-1096; Fuskasawa et al. (1999) *Vaccine* 17:2951-2958; and Rosenqist et al. (1998) *Dev. Biol. Strand* 92:323-333) purified or derived from *N. men-*

*ingitides* serogroup such as A, C, W135, Y, and/or B. *Meningitides* protein antigens can be selected from adhesions, autotransporters, toxins, Fe acquisition proteins, and membrane associated proteins (preferably integral outer membrane protein).

*Streptococcus pneumoniae*: *Streptococcus pneumoniae* antigens include a saccharide (including a polysaccharide or an oligosaccharide) and/or protein from *Streptococcus pneumoniae*. Saccharide antigens can be selected from serotypes 1, 2, 3, 4, 5, 6B, 7F, 8, 9N, 9V, 10A, 11A, 12F, 14, 15B, 17F, 18C, 19A, 19F, 20, 22F, 23F, and 33F. Protein antigens can be selected from a protein identified in WO 98/18931; WO 98/18930; U.S. Pat. Nos. 6,699,703; 6,800,744; WO 97/43303; and WO 97/37026. *Streptococcus pneumoniae* proteins can be selected from the Poly Histidine Triad family (PhtX), the Choline Binding Protein family (CbpX), CbpX truncates, LytX family, LytX truncates, CbpX truncate-LytX truncate chimeric proteins, pneumolysin (Ply), PspA, PsaA, Sp128, Sp101, Sp130, Sp125 or Sp133.

*Streptococcus pyogenes* (Group A *Streptococcus*): Group A *Streptococcus* antigens include proteins identified in WO 02/34771 and WO 2005/032582 (including GAS 40), fusions of fragments of GAS M proteins (including those described in WO 02/094851; and Dale (1999) *Vaccine* 17:193-200, and Dale (1996) *Vaccine* 14(10): 944-948), fibronectin binding protein (Sfbl), Streptococcal heme-associated protein (Shp), and Streptolysin S (SagA).

*Moraxella catarrhalis*: *Moraxella* antigens include antigens identified in WO 02/18595; and WO 99/58562, outer membrane protein antigens (HMW-OMP), C-antigen, and/or LPS.

*Bordetella pertussis*: Pertussis antigens include petussis holotoxin (PT) and filamentous haemagglutinin (FHA) from *B. pertussis*, optionally also combination with pertactin and/or agglutinogens 2 and 3 antigen.

*Staphylococcus aureus*: Staph aureus antigens include *S. aureus* type 5 and 8 capsular polysaccharides optionally conjugated to nontoxic recombinant *Pseudomonas aeruginosa* exotoxin A, such as STAPHVAX™ *S. aureus* vaccine, and antigens derived from surface proteins, invasins (leukocidin, kinases, hyaluronidase), surface factors that inhibit phagocytic engulfment (capsule, Protein A), carotenoids, catalase production, Protein A, coagulase, clotting factor, and membrane-damaging toxins (optionally detoxified) that lyse eukaryotic cell membranes (hemolysins, leukotoxin, leukocidin).

*Staphylococcus epidermis*: *S. epidermidis* antigens include slime-associated antigen (SAA).

*Clostridium tetani* (Tetanus): Tetanus antigens include tetanus toxoid (TT), preferably used as a carrier protein in conjunction/conjugated with the compositions of the present invention.

*Cornynebacterium diphtheriae* (Diphtheria): Diphtheria antigens include diphtheria toxin, preferably detoxified, such as $CRM_{197}$. Additionally, antigens capable of modulating, inhibiting or associated with ADP ribosylation are contemplated for combination/co-administration/conjugation with the compositions of the present invention. The diphtheria toxoids may be used as carrier proteins.

*Haemophilus influenzae* B (Hib): Hib antigens include a Hib saccharide antigen.

*Pseudomonas aeruginosa*: *Pseudomonas* antigens include endotoxin A, Wzz protein, *P. aeruginosa* LPS, more particularly LPS isolated from PAO1 (05 serotype), and Outer Membrane Proteins, including Outer Membrane Proteins F (OprF) (Price et al. (2001) *Infect Immun* 69(5):3510-3515).

*Legionella pneumophila*. Bacterial antigens can be derived from *Legionella pneumophila*.

*Streptococcus agalactiae* (Group B *Streptococcus*): Group B *Streptococcus* antigens include protein and saccharide antigens, such as those identified in WO 02/34771; WO 03/093306; WO 04/041157; and WO 2005/002619 (including proteins GBS 59, GBS 67, GBS 80, GBS 104, GBS 276, GBS 322, and including saccharide antigens derived from serotypes Ia, Ib, Ia/c, II, III, IV, V, VI, VII and VIII).

*Neiserria gonorrhoeae*: Gonorrhoeae antigens include Por (or porin) protein, such as PorB (see, e.g., Zhu et al. (2004) *Vaccine* 22:660-669), a transferring binding protein, such as TbpA and TbpB (see, e.g., Price et al. (2004) *Infect. Immun.* 71(1):277-283), an opacity protein (such as Opa), a reduction-modifiable protein (Rmp), and outer membrane vesicle (OMV) preparations (see, e.g., Plante et al. (2000) *J. Infect. Dis.* 182:848-855); WO 99/24578; WO 99/36544; WO 99/57280; and WO02/079243).

*Chlamydia trachomatis*: *Chlamydia trachomatis* antigens include antigens derived from serotypes A, B, Ba and C (agents of trachoma, a cause of blindness), serotypes $L_1$, $L_2$ & $L_3$ (associated with Lymphogranuloma venereum), and serotypes, D-K. *Chlamydia* trachomas antigens also include antigens identified in WO 00/37494; WO 03/049762; WO 03/068811; and WO 05/002619, including PepA (CT045), LcrE (CT089), ArtJ (CT381), DnaK (CT396), CT398. OmpH-like (CT242), L7/L12 (CT316), OmcA (CT444), AtosS (CT467), CT547, Eno (CT587), HrtA (CT823), MurG (CT761), CT396 and CT761, and specific combinations of these antigens.

*Treponema pallidum* (Syphilis): Syphilis antigens include TmpA antigen.

*Haemophilus ducreyi* (causing chancroid): *Ducreyi* antigens include outer membrane protein (DsrA).

*Enterococcus faecalis* or *Enterococcus faecium*: Antigens include a trisaccharide repeat and other *Enterococcus* derived antigens provided in U.S. Pat. No. 6,756,361.

*Helicobacter pylori*: *H pylori* antigens include Cag, Vac, Nap, HopX, HopY and urease antigen.

*Staphylococcus saprophyticus*: Antigens include the 160 kDa hemagglutinin of *S. saprophyticus* antigen.

*Yersinia enterocolitica* Antigens include LPS (Xu et al. (2002) *Infect. Immun.* 70(8): 4414-4423).

*E. coli*: *E. coli* antigens can be derived from enterotoxigenic *E. coli* (ETEC), enteroaggregative *E. coli* (EAggEC), diffusely adhering *E. coli* (DAEC), enteropathogenic *E. coli* (EPEC), or enterohemorrhagic *E. coli* (EHEC).

*Bacillus anthracis* (anthrax): *B. anthracis* antigens are optionally detoxified and can be selected from A-components (lethal factor (LF) and edema factor (EF)), both of which can share a common B-component known as protective antigen (PA). In certain embodiments, the compositions of the present invention do not include an anthrax antigen.

*Yersinia pestis* (plague): Plague antigens include F1 capsular antigen (Gosfield et al. (2003) *Infect. Immun* 71(1)): 374-383), LPS (Fields et al. (1999) *Infect. Immun* 67(10): 5396-5408), *Yersinia pestis* V antigen (Hill et al. (1997) *Infect. Immun* 65(11): 4476-4482.

*Mycobacterium tuberculosis*: Tuberculosis antigens include lipoproteins, LPS, BCG antigens, a fusion protein of antigen 85B (Ag85B) and ESAT-6 optionally formulated in cationic lipid vesicles (Olsen et al. (2004) *Infect. Immun.* 72(10): 6148-6150), *Mycobacterium tuberculosis* (Mtb) isocitrate dehydrogenase associated antigens (Banerjee et al. (2004) *Proc. Natl. Acad. Sci USA* 101 (34): 12652-12657), and MPT51 antigens ((Suzuki et al. (2004) *Infect. Immun.* 72(7):3829-3837).

*Rickettsia*: Antigens include outer membrane proteins, including the outer membrane protein A and/or B (OmpB) (Chao et al. (2004) *Biochim. Biophys. Acta.* 1702(2):145-152), LPS, and surface protein antigen (SPA) (Carl et al. (1989)-J. Autoirmmun. 2 Suppl:81-91).

*Listeria monocytogenes*. Bacterial antigens can be derived from *Listeria monocytogenes*.

*Chlamydia pneumoniae*: Antigens include those identified in WO 02/02606 and WO 05/084306, including CPn0324, Cpn0301, Cpn0482, Cpn0503, Cpn0525, Cpn0558, Cpn0584, Cpn0800, Cpn0979, Cpn0498, Cpn0300, Cpn0042, Cpn0013, Cpn450, Cpn0661, Cpn0557, Cpn0904, Clpn0795, Cpn0186 and Cpn0604, and specific combinations of these antigens.

*Vibrio cholerae*: Antigens include proteinase antigens, LPS, particularly lipopolysaccharides of *Vibrio cholerae* II, 01 Inaba O-specific polysaccharides, *V. cholera* 0139, antigens of IEM108 vaccine (Liang et al. (2003) *Infect. Immun.* 71(10):5498-5504), and *Zonula occludens* toxin (Zot).

*Salmonella typhi* (typhoid fever): Antigens include capsular polysaccharides preferably conjugates (Vi, i.e. vax-TyVi).

*Borrelia burgdorferi* (Lyme disease): Antigens include lipoproteins (such as OspA, OspB, Osp C and Osp D), other surface proteins such as OspE-related proteins (Erps), decorin-binding proteins (such as DbpA), and antigenically variable VI proteins, such as antigens associated with P39 and P13 (an integral membrane protein, Noppa et al. (2001); *Infect. Immun.* 69(5):3323-3334), VlsE Antigenic Variation Protein (Lawrenz et al. (1999) *J. Clin Microbiol.* 37(12): 3997-4004).

*Porphyromonas gingivalis*: Antigens include *P. gingivalis* outer membrane protein (OMP).

*Klebsiella*: Antigens include OMPs, including OMP A, and polysaccharides optionally conjugated to tetanus toxoid.

Other bacterial antigens include capsular antigens, polysaccharide antigens or protein antigens of any of the above. Further bacterial antigens also include outer membrane vesicle (OMV) preparations. Additionally, antigens include live, attenuated, and/or purified versions of any of the aforementioned bacteria. Antigens can be derived from gram-negative or gram-positive bacteria. Antigens can be derived from aerobic or anaerobic bacteria.

Additionally, any of the above bacterial-derived saccharides (polysaccharides, LPS, LOS or oligosaccharides) can be conjugated to another agent or antigen, such as a carrier protein (for example $CRM_{197}$). Such conjugation can be direct conjugation effected by reductive amination of carbonyl moieties on the saccharide to amino groups on the protein, as provided in U.S. Pat. No. 5,360,897; and Roy et al. (1984) *Can. J. Biochem. Cell Biol.* 62(5):270-275. In another embodiment, the saccharides can be conjugated through a linker, such as, with succinamide or other linkages provided in Hermanson, G. T., Bioconjugate Techniques, 1st ed., Academic Press (1996) and Wong, S. S., CRC, Chemistry of Protein Conjugation and Cross-Linking, 1st ed., CRC-Press (1991).

B. Viral Antigens

Viral antigens suitable for use in the invention include inactivated (or killed) virus, attenuated virus, split virus formulations, purified subunit formulations, viral proteins which may be isolated, purified or derived from a virus, and Virus Like Particles (VLPs). Viral antigens can be derived from viruses propagated on cell culture or other substrate or expressed recombinantly. Viral antigens preferably include epitopes which are exposed on the surface of the virus during at least one stage of its life cycle. Viral antigens are preferably conserved across multiple serotypes or isolates. Viral antigens include antigens derived from one or more of the viruses set forth below as well as the specific antigens examples identified below.

Orthomyxovirus: Viral antigens may be derived from an Orthomyxovirus, such as Influenza A, B and C. Orthomyxovirus antigens may be selected from one or more of the viral proteins, including hemagglutinin (HA), neuraminidase (NA), nucleoprotein (NP), matrix protein (M1), membrane protein (M2), one or more of the transcriptase components (PB1, PB2 and PA). Preferred antigens include HA and NA.

Influenza antigens may be derived from interpandemic (annual) flu strains. Influenza antigens may be derived from strains with the potential to cause pandemic a pandemic outbreak (i.e., influenza strains with new haemagglutinin compared to the haemagglutinin in currently circulating strains, or influenza strains which are pathogenic in avian subjects and have the potential to be transmitted horizontally in the human population, or influenza strains which are pathogenic to humans). Influenza antigens may be derived from viruses grown in eggs or cell culture.

Paramyxoviridae viruses: Viral antigens may be derived from Paramyxoviridae viruses, such as Pneumoviruses (RSV), Paramyxoviruses (PIV) and Morbilliviruses (Measles).

Pneumovirus: Viral antigens may be derived from a Pneumovirus, such as Respiratory syncytial virus (RSV), Bovine respiratory syncytial virus, Pneumonia virus of mice, and Turkey rhinotracheitis virus. Preferably, the Pneumovirus is RSV. Pneumovirus antigens may be selected from one or more of the following proteins, including surface proteins Fusion (F), Glycoprotein (G) and Small Hydrophobic protein (SH), matrix proteins M and M2, nucleocapsid proteins N, P and L and nonstructural proteins NS1 and NS2. Preferred Pneumovirus antigens include F, G and M. See e.g., Johnstone et al. (2004) *J. Gen. Virol.* 85 (Pt 11):3229-3238). Pneumovirus antigens may also be formulated in or derived from chimeric viruses. For example, chimeric RSV/PIV viruses may comprise components of both RSV and PIV.

Paramyxovirus: Viral antigens may be derived from a Paramyxovirus, such as Parainfluenza virus types 1-4 (PIV), Mumps, Sendai viruses, Simian virus 5, Bovine parainfluenza virus and Newcastle disease virus. Preferably, the Paramyxovirus is PIV or Mumps. Paramyxovirus antigens may be selected from one or more of the following proteins: Hemagglutinin Neuraminidase (HN), Fusion proteins F1 and F2, Nucleoprotein (NP), Phosphoprotein (P), Large protein (L), and Matrix protein (M). Preferred Paramyxovirus proteins include HN, F1 and F2. Paramyxovirus antigens may also be formulated in or derived from chimeric viruses. For example, chimeric RSV/PIV viruses may comprise components of both RSV and PIV. Commercially available mumps vaccines include live attenuated mumps virus, in either a monovalent form or in combination with measles and rubella vaccines (MMR).

Morbillivirus: Viral antigens may be derived from a Morbillivirus, such as Measles. Morbillivirus antigens may be selected from one or more of the following proteins: hemagglutinin (H), Glycoprotein (G), Fusion factor (F), Large protein (L), Nucleoprotein (NP), Polymerase phosphoprotein (P), and Matrix (M). Commercially available measles vaccines include live attenuated measles virus, typically in combination with mumps and rubella (MMR).

Picornavirus: Viral antigens may be derived from Picornaviruses, such as Enteroviruses, Rhinoviruses, Hepamavirus, Cardioviruses and Aphthoviruses. Antigens derived from Enteroviruses, such as Poliovirus are preferred.

Enterovirus: Viral antigens may be derived from an Enterovirus, such as Poliovirus types 1, 2 or 3, Coxsackie A virus types 1 to 22 and 24, Coxsackie B virus types 1 to 6, Echovirus (ECHO) virus) types 1 to 9, 11 to 27 and 29 to 34 and Enterovirus 68 to 71. Preferably, the Enterovirus is poliovirus. Enterovirus antigens are preferably selected from one or more of the following Capsid proteins VP1, VP2, VP3 and VP4. Commercially available polio vaccines include Inactivated Polio Vaccine (IPV) and Oral poliovirus vaccine (OPV).

Heparnavirus: Viral antigens may be derived from a Heparnavirus, such as Hepatitis A virus (HAV). Commercially available HAV vaccines include inactivated HIAV vaccine.

Togavirus: Viral antigens may be derived from a Togavirus, such as a Rubivirus, an Alphavirus, or an Arterivirus. Antigens derived from Rubivirus, such as Rubella virus, are preferred. Togavirus antigens may be selected from E1, E2, E3, C, NSP-1, NSPO-2, NSP-3 and NSP-4. Togavirus antigens are preferably selected from E1, E2 and E3. Commercially available Rubella vaccines include a live cold-adapted virus, typically in combination with mumps and measles vaccines (MMR).

Flavivirus: Viral antigens may be derived from a Flavivirus, such as Tick-borne encephalitis (TBE), Dengue (types 1, 2, 3 or 4), Yellow Fever, Japanese encephalitis, West Nile encephalitis, St. Louis encephalitis, Russian spring-summer encephalitis, Powassan encephalitis.

Flavivirus antigens may be selected from PrM, M, C, E, NS-1, NS-2a, NS2b, NS3, NS4a, NS4b, and NS5. Flavivirus antigens are preferably selected from PrM, M and E. Commercially available TBE vaccine include inactivated virus vaccines.

Pestivirus: Viral antigens may be derived from a Pestivirus, such as Bovine viral diarrhea (BVDV), Classical swine fever (CSFV) or Border disease (BDV).

Hepadnavirus: Viral antigens may be derived from a Hepadnavirus, such as Hepatitis B virus. Hepadnavirus antigens may be selected from surface antigens (L, M and S), core antigens (HBc, HBe). Commercially available HBV vaccines include subunit vaccines comprising the surface antigen S protein.

Hepatitis C virus: Viral antigens may be derived from a Hepatitis C virus (HCV). HCV antigens may be selected from one or more of E1, E2, E1/E2, NS345 polyprotein, NS 345-core polyprotein, core, and/or peptides from the nonstructural regions (Houghton et al. (1991) *Hepatology* 14:381-388).

Rhabdovirus: Viral antigens may be derived from a Rhabdovirus, such as a Lyssavirus (Rabies virus) and Vesiculovirus (VSV). Rhabdovirus antigens may be selected from glycoprotein (G), nucleoprotein (N), large protein (L) and nonstructural proteins (NS). Commercially available Rabies virus vaccine comprise killed virus grown on human diploid cells or fetal rhesus lung cells.

Caliciviridae: Viral antigens may be derived from Caliciviridae, such as Norwalk virus, and Norwalk-like Viruses, such as Hawaii Virus and Snow Mountain Virus.

Coronavirus: Viral antigens may be derived from a Coronavirus, SARS, Human respiratory coronavirus, Avian infectious bronchitis (IBV), Mouse hepatitis virus (MHV), and Porcine transmissible gastroenteritis virus (TGEV). Coronavirus antigens may be selected from spike (S), envelope (E), matrix (M), nucleocapsid (N), and Hemagglutinin-esterase glycoprotein (HE). Preferably, the Coronavirus antigen is derived from a SARS virus. SARS viral antigens are described in WO 04/92360;

Retrovirus: Viral antigens may be derived from a Retrovirus, such as an Oncovirus, a Lentivirus or a Spumavirus. Oncovirus antigens may be derived from HTLV-1, HTLV-2 or HTLV-5. Lentivirus antigens may be derived from HIV-1 or HIV-2. Retrovirus antigens may be selected from gag, pol, env, tax, tat, rex, rev, nef, vif, vpu, and vpr. HIV antigens may be selected from gag (p24gag and p55gag), env (gp160 and gp41), pol, tat, nef, rev vpu, miniproteins, (preferably p55 gag and gp140v delete). HIV antigens may be derived from one or more of the following strains: $HIV_{IIIb}$, $HIV_{SF2}$, $HIV_{LAV}$, $HIV_{LAI}$, $HIV_{MN}$, HIV-1$_{CM235}$, HIV-1$_{US4}$.

Reovirus: Viral antigens may be derived from a Reovirus, such as an Orthoreovirus, a Rotavirus, an Orbivirus, or a Coltivirus. Reovirus antigens may be selected from structural proteins $\lambda1$, $\lambda2$, $\lambda3$, $\mu1$, $\mu2$, $\sigma1$, $\sigma2$, or $\sigma3$, or nonstructural proteins $\sigma NS$, $\mu NS$, or $\sigma Is$. Preferred Reovirus antigens may be derived from a Rotavirus. Rotavirus antigens may be selected from VP1, VP2, VP3, VP4 (or the cleaved product VP5 and VP8), NSP 1, VP6, NSP3, NSP2, VP7, NSP4, or NSP5. Preferred Rotavirus antigens include VP4 (or the cleaved product VP5 and VP8), and VP7.

Parvovirus: Viral antigens may be derived from a Parvovirus, such as Parvovirus B19. Parvovirus antigens may be selected from VP-1, VP-2, VP-3, NS-1 and NS-2. Preferably, the Parvovirus antigen is capsid protein VP-2.

Delta hepatitis virus (HDV): Viral antigens may be derived HDV, particularly $\delta$-antigen from HDV (see, e.g., U.S. Pat. No. 5,378,814).

Hepatitis E virus (HEV): Viral antigens may be derived from HEV.

Hepatitis G virus (HGV): Viral antigens may be derived from HGV.

Human Herpesvirus: Viral antigens may be derived from a Human Herpesvirus, such as Herpes Simplex Viruses (HSV), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8). Human Herpesvirus antigens may be selected from immediate early proteins ($\alpha$), early proteins ($\beta$), and late proteins ($\gamma$). HSV antigens may be derived from HSV-1 or HSV-2 strains. HSV antigens may be selected from glycoproteins gB, gC, gD and gH, fusion protein (gB), or immune escape proteins (gC, gE, or gI). VZV antigens may be selected from core, nucleocapsid, tegument, or envelope proteins. A live attenuated VZV vaccine is commercially available. EBV antigens may be selected from early antigen (EA) proteins, viral capsid antigen (VCA), and glycoproteins of the membrane antigen (MA). CMV antigens may be selected from capsid proteins, envelope glycoproteins (such as gB and gH), and tegument proteins Papovaviruses: Antigens may be derived from Papovaviruses, such as Papillomaviruses and Polyomaviruses. Papillomaviruses include HPV serotypes 1, 2, 4, 5, 6, 8, 11, 13, 16, 18, 31, 33, 35, 39, 41, 42, 47, 51, 57, 58, 63 and 65. Preferably, HPV antigens are derived from serotypes 6, 11, 16 or 18. HPV antigens may be selected from capsid proteins (L1) and (L2), or E1-E7, or fusions thereof. HPV antigens are preferably formulated into virus-like particles (VLPs). Polyomyavirus viruses include BK virus and JK virus. Polyomavirus antigens may be selected from VP1, VP2 or VP3.

Other antigens, compositions, methods, and microbes for use in the invention are described in Plotkin, S. A. et al., *Vaccines*, $4^{th}$ ed., W.B. Saunders Co. (2004); Murray, P. R. et al., *Medical Microbiology* $5^{th}$ ed., *Mosby Elsevier* (2005);

Joklik, W. K. (ed.), *Virology*, 3rd ed., Appleton & Lange (1988); Howley, P. M. et al. (eds.), *Fundamental Virology*. 4th ed., Lippincott Williams & Wilkins (1991); and Fields, B. N. et al. (eds.), *Fields Virology*, 4th ed., Lippincott Williams & Wilkins (2001).

c. Fungal Antigens

Fungal antigens for use in the invention can be derived from one or more of the fungi set forth below.

Fungal antigens may be derived from Dermatophytres, including: *Epidermophyton floccusum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T. verrucosum* var. *album,* var. *discoides,* var. *ochraceum, Trichophyton violaceum,* and/or *Trichophyton faviforme.*

Fungal pathogens may be derived from *Aspergillus fumigatus, Aspergillus flavus, Aspergillus niger, Aspergillus nidulans, Aspergillus terreus, Aspergillus sydowii, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum. Klebsiella pneumoniae, Paracoccidioides brasiliensis, Pneumocystis carinii, Pythiumn insidiosum, Pityrosporum ovale, Saccharomyces cerevisae, Saccharomyces boulardii, Saccharomyces pombe, Scedosporium apiosperum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp, *Mucor* spp, *Absidia* spp, *Mortierella* spp, *Cunninghamella* spp, *Saksenaea* spp., *Alternaria* spp, *Curvularia* spp, *Helminthosporium* spp, *Fusarium* spp, *Aspergillus* spp, *Penicillium* spp, *Monolinia* spp, *Rhizoctonia* spp, *Paecilomyces* spp, *Pithomyces* spp, and *Cladosporium* spp.

Processes for producing fungal antigens are well known in the art (see U.S. Pat. No. 6,333,164). In a preferred method, a solubilized fraction extracted and separated from an insoluble fraction obtainable from fungal cells of which cell wall has been substantially removed or at least partially removed, characterized in that the process comprises the steps of: obtaining living fungal cells; obtaining fungal cells of which cell wall has been substantially removed or at least partially removed; bursting the fungal cells of which cell wall has been substantially removed or at least partially removed; obtaining an insoluble fraction; and extracting and separating a solubilized fraction from the insoluble fraction.

D. STD Antigens

The compositions of the invention can include one or more antigens derived from a sexually transmitted disease (STD). Such antigens can provide for prophylactis or therapy for STDs such as *chlamydia*, genital herpes, hepatits (such as HCV), genital warts, gonorrhoea, syphilis and/or chancroid (see WO 00/15255). Antigens may be derived from one or more viral or bacterial STDs. Viral STD antigens for use in the invention may be derived from, for example, HIV, herpes simplex virus (HSV-1 and HSV-2), human papillomavirus (HPV), and hepatitis (HCV). Bacterial STD antigens for use in the invention may be derived from, for example, *Neiserria gonorrhoeae, Chlamydia trachomatis, Treponema pallidum, Haemophilus ducreyi, E. coli,* and *Streptococcus agalactiae.* Examples of specific antigens derived from these pathogens are described above.

E. Respiratory Antigens

The compositions of the invention can include one or more antigens derived from a pathogen which causes respiratory disease. For example, respiratory antigens may be derived from a respiratory virus such as Orthomyxoviruses (influenza), Pneumovirus (RSV), Paramyxovirus (PIV), Morbillivirus (measles), Togavirus (Rubella), VZV, and Coronavirus (SARS). Respiratory antigens may be derived from a bacterium which causes respiratory disease, such as *Streptococcus pneumoniae, Pseudomonas aeruginosa, Bordetella pertussis, Mycobacterium tuberculosis, Mycoplasma pneumoniae, Chlamydia pneumoniae, Bacillus anthracis,* and *Moraxella catarrhalis.* Examples of specific antigens derived from these pathogens are described above.

F. Pediatric Vaccine Antigens

The compositions of the invention may include one or more antigens suitable for use in pediatric subjects. Pediatric subjects are typically less than about 3 years old, or less than about 2 years old, or less than about 1 years old. Pediatric antigens can be administered multiple times over the course of 6 months, 1, 2 or 3 years. Pediatric antigens may be derived from a virus which may target pediatric populations and/or a virus from which pediatric populations are susceptible to infection. Pediatric viral antigens include antigens derived from one or more of Orthomyxovirus (influenza), Pneumovirus (RSV), Paramyxovirus (PIV and Mumps), Morbillivirus (measles), Togavirus (Rubella), Enterovirus (polio), HBV, Coronavirus (SARS), and Varicella-zoster virus (VZV), Epstein Barr virus (EBV). Pediatric bacterial antigens include antigens derived from one or more of *Streptococcus pneumoniae, Neisseria meningitides, Streptococcus pyogenes* (Group A *Streptococcus*), *Moraxella catarrhalis, Bordetella pertussis, Staphylococcus aureus, Clostridium tetani* (Tetanus), *Corynebacterium diphtheriae* (Diphtheria), *Haemophilus influenzae* B (Hib), *Pseudomonas aeruginosa, Streptococcus agalactiae* (Group B *Streptococcus*), and *E. coli.* Examples of specific antigens derived from these pathogens are described above.

G. Antigens Suitable for Use in Elderly or Immunocompromised Individuals

The compositions of the invention can include one or more antigens suitable for use in elderly or immunocompromised individuals. Such individuals may need to be vaccinated more frequently, with higher doses or with adjuvanted formulations to improve their immune response to the targeted antigens. Antigens which may be targeted for use in elderly or immunocompromised individuals include antigens derived from one or more of the following pathogens: *Neisseria meningitides, Streptococcus pneumoniae, Streptococcus pyogenes* (Group A *Streptococcus*), *Moraxella catarrhalis, Bordetella pertussis, Staphylococcus aureus, Staphylococcus epidermis, Clostridium tetani* (Tetanus), *Corynebacterium diphtheriae* (Diphtheria), *Haemophilus influenzae* B (Hib), *Pseudomonas aeruginosa, Legionella pneumophila, Streptococcus agalactiae* (Group B *Streptococcus*), *Enterococcus faecalis, Helicobacter pylori, Clamydia pneumoniae,* Orthomyxovirus (influenza), Pneumovirus (RSV), Paramyxovirus (PIV and Mumps), Morbillivirus (measles), Togavirus (Rubella), Enterovirus (polio), HBV, Coronavirus (SARS), Varicella-zoster virus (VZV), Epstein Barr virus (EBV), Cytomegalovirus (CMV). Examples of specific antigens derived from these pathogens are described above.

H. Antigens Suitable for Use in Adolescent Vaccines

The compositions of the invention can include one or more antigens suitable for use in adolescent subjects. Adolescents may be in need of a boost of a previously administered pediatric antigen. Pediatric antigens which may be suitable for use in adolescents are described above. In addition, adolescents may be targeted to receive antigens derived from an STD pathogen in order to ensure protective or therapeutic immunity before the beginning of sexual activity. STD antigens which may be suitable for use in adolescents are described above.

I. Tumor Antigens

The compositions of the invention can include one or more tumor or cancer antigens. Tumor antigens can be, for example, peptide-containing tumor antigens, such as a polypeptide tumor antigen or glycoprotein tumor antigens. A tumor antigen can also be, for example, a saccharide-containing tumor antigen, such as a glycolipid tumor antigen or a ganglioside tumor antigen. A tumor antigen can further be, for example, a polynucleotide-containing tumor antigen that expresses a polypeptide-containing tumor antigen, for instance, an RNA vector construct or a DNA vector construct, such as plasmid DNA.

Tumor antigens include (a) polypeptide-containing tumor antigens, including polypeptides (which can range, for example, from 8-20 amino acids in length, although lengths outside this range are also common), lipopolypeptides and glycoproteins, (b) saccharide-containing tumor antigens, including poly-saccharides, mucins, gangliosides, glycolipids and glycoproteins, and (c) polynucleotides that express antigenic polypeptides.

Tumor antigens can be, for example, (a) full length molecules associated with cancer cells, (b) homologs and modified forms of the same, including molecules with deleted, added and/or substituted portions, and (c) fragments of the same. Tumor antigens can be provided in recombinant form. Tumor antigens include, for example, class I-restricted antigens recognized by CD8+ lymphocytes or class II-restricted antigens recognized by CD4+ lymphocytes.

Numerous tumor antigens are known in the art, including: (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors), (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLR-FUT, (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer), (d) shared antigens, for example, melanoma-melanocyte differentiation antigens such as MART-1/Melan A, gp100, MC1R, melanocyte-stimulating hormone receptor, tyrosinase, tyrosinase related protein-1/TRP1 and tyrosinase related protein-2/TRP2 (associated with, e.g., melanoma), (e) prostate associated antigens such as PAP, PSA, PSMA, PSH-P1, PSM-P1, PSM-P2, associated with e.g., prostate cancer, (f) immunoglobulin idiotypes (associated with myeloma and B cell lymphomas, for example), and (g) other tumor antigens, such as polypeptide- and saccharide-containing antigens including (i) glycoproteins such as sialyl Tn and sialyl Lex (associated with, e.g., breast and colorectal cancer) as well as various mucins; glycoproteins may be coupled to a carrier protein (e.g., MUC-1 may be coupled to KLH); (ii) lipopolypeptides (e.g., MUC-1 linked to a lipid moiety); (iii) polysaccharides (e.g., Globo H synthetic hexasaccharide), which may be coupled to a carrier proteins (e.g., to KLH), (iv) gangliosides such as GM2, GM12, GD2, GD3 (associated with, e.g., brain, lung cancer, melanoma), which also may be coupled to carrier proteins (e.g., KLH).

Other tumor antigens include p15, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29BCAA), CA 195, CA 242, CA-50, CAM43, CD68KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein\cyclophilin C-associated protein), TAAL6, TAG72, TLP, TPS, and the like. These as well as other cellular components are described for example in United States Patent Publication No. 2002/0007173 and references cited therein.

Tumor antigens may be derived, for example, from mutated or altered cellular components. After alteration, the cellular components no longer perform their regulatory functions, and hence the cell may experience uncontrolled growth. Representative examples of altered cellular components include ras, p53, Rb, altered protein encoded by the Wilms' tumor gene, ubiquitin, mucin, protein encoded by the DCC, APC, and MCC genes, as well as receptors or receptor-like structures such as neu, thyroid hormone receptor, platelet derived growth factor (PDGF) receptor, insulin receptor, epidermal growth factor (EGF) receptor, and the colony stimulating factor (CSF) receptor. These as well as other cellular components are described for example in U.S. Pat. No. 5,693,522 and references cited therein.

Bacterial and viral antigens, may be used in conjunction with the compositions of the present invention for the treatment of cancer. In particular, carrier proteins, such as $CRM_{197}$, tetanus toxoid, or Salmonella typhimurium antigen may be used in conjunction/conjugation with compounds of the present invention for treatment of cancer. The cancer antigen combination therapies will show increased efficacy and bioavailability as compared with existing therapies.

Additional information on cancer or tumor antigens can be found, for example, in Moingeon (2001) *Vaccine* 19:1305-1326; Rosenberg (2001) *Nature* 411:380-384; Dermine et al. (2002) *Brit. Med. Bull.* 62:149-162; Espinoza-Delgado (2002) *The Oncologist* 7 (suppl 3):20-33; Davis et al. (2003) *J. Leukocyte Biol.* 23:3-29; Van den Eynde et al. (1995) *Curr. Opin. Immunol.* 7:674-681; Rosenberg (1997) *Immunol. Today* 18:175-182; Offringa et al. (2000) *Curr. Opin. Immunol.* 2:576-582; Rosenberg (1999) *Immunity* 10:281-287; Sahin et al. (1997) *Curr. Opin. Immunol.* 9:709-716; Old et al. (1998) *J. Exp. Med.* 187:1163-1167; Chaux et al. (1999) *J. Exp. Med.* 189:767-778; Gold et al. (1965) *J. Exp. Med.* 122:467-468; Livingston et al. (1997) *Cancer Immunol. Immunother.* 45:1-6; Livingston et al. (1997) *Cancer Immunol. Immunother.* 45:10-19; Taylor-Papadimitriou (1997) *Immunol. Today* 18:105-107; Zhao et al. (1995) *J. Exp. Med.* 182:67-74; Theobald et al. (1995) *Proc. Natl. Acad. Sci. USA* 92:11993-11997; Gaudernack (1996) *Immunotechnology* 2:3-9; WO 91/02062; U.S. Pat. No. 6,015,567; WO 01/08636; WO 96/30514; U.S. Pat. Nos. 5,846,538; and 5,869,445.

Further antigens may also include an outer membrane vesicle (OMV) preparation.

Additional formulation methods and antigens (especially tumor antigens) are provided in U.S. Patent Publication No. 2004/0202680. See also U.S. Pat. No. 6,884,435.

J. Antigen References

The compositions of the invention can include antigens described in any of the following references:
1 International Publication No. WO99/24578.
2 International Publication No. WO99/36544.
3 International Publication No. WO99/57280.
4 International Publication No. WO00/22430.
5 Tettelin et al. (2000) *Science* 287:1809-1815.
6 International Publication No. WO96/29412.
7 Pizza et al. (2000) *Science* 287:1816-1820.
8 International Publication No. WO 01/52885.
9 Bjune et al. (1991) *Lancet* 338(8775):1093-1096.
10 Fuskasawa et al. (1999) *Vaccine* 17:2951-2958.
11 Rosenqist et al. (1998) *Dev. Biol. Strand* 92:323-333.
12 Costantino et al. (1992) *Vaccine* 10:691-698.
13 Costantino et al. (1999) *Vaccine* 17:1251-1263.
14 Watson (2000) *Pediatr. Infect. Dis. J.* 19:331-332.
15 Rubin (2000)*Pediatr. Clin. North Am.* 47:269-285.
16 Jedrzejas (2001)*Microbiol. Mol. Biol. Rev.* 65:187-207.
17 International Publication No. WO 02/02606.
18 Kalman et al. (1999) *Nature Genetics* 21:385-389.
19 Read et al. (2000) *Nucleic Acids Res.* 28:1397-1406.
20 Shirai et al. (2000) *J. Infect. Dis.* 181 (Suppl 3):S524-S527.
21 International Publication No. WO99/27105.
22 International Publication No. WO00/27994.
23 International Publication No. WO00/37494.
24 International Publication No. WO99/28475.
25 Bell (2000) *Pediatr. Infect. Dis. J.* 19:1187-1188.
26 Iwarson (1995) *APMIS* 103:321-326.
27 Gerlich et al. (1990) *Vaccine* 8 Suppl:S63-S68, S79-S80.
28 Hsu et al. (1999) *Clin. Liver Dis.* 3:901-915.
29 Gastofsson et al. (1996) *N. Engl. J. Med.* 334:349-355.
30 Rappuoli et al. (1991) *TIBTECH* 9:232-238.
31 Plotkin, S. A. et al., *Vaccines*, 4$^{th}$ ed., W.B. Saunders Co. (2004)
32 Del Guidice et al. (1998) *Mol. Aspects Med.* 19:1-70.
33 International Publication No. WO93/018150.
34 International Publication No. WO99/53310.
35 International Publication No. WO98/04702.
36 Ross et al. (2001) *Vaccine* 19:135-142.
37 Sutter et al. (2000) *Pediatr. Clin. North Am.* 47:287-308.
38 Zimmerman & Spann (1999)*Am. Fam. Physician* 59:113-118, 125-126.
39 Dreensen (1997) *Vaccine* 15 Suppl:S2-S6.
40 *MMWR Morb. Mortal Wkly Rep.* (1998) 16:47(1):12, 19.
41 McMichael (2000) Vaccine 19 Suppl 1:S101-S107.
42 Schuchat (1999) *Lancet* 353(9146):51-56.
43 GB patent applications 0026333.5, 0028727.6 & 0105640.7.
44 Dale (1999) *Infect. Disclin. North Am.* 13:227-243.
45 Ferretti et al. (2001) *Proc. Natl. Acad. Sci. USA* 98: 4658-4663.
46 Kuroda et al. (2001) *Lancet* 357(9264):1225-1240.
47 Ala'Aldeen et al. (2001) *Lancet* 357(9264):1218-1219.
48 Ramsay et al. (2001) *Lancet* 357(9251):195-196.
49 Lindberg (1999) *Vaccine* 17 Suppl 2:S28-S36.
50 Buttery & Moxon (2000) *J. R. Coil Physicians Long* 34:163-168.
51 Ahmad & Chapnick (1999) *Infect. Dis. Clin. North Am.* 13:113-133.
52 Goldblatt (1998)*J. Med. Microbiol.* 47:663-667.
53 European Patent No. EP 0 477 508B1.
54 U.S. Pat. No. 5,306,492.
55 International Publication No. WO98/42721.
56 Cruse et al. (eds.) *Conjugate Vaccines, particularly* vol. 10:48-114.
57 Hermanson, G. T., Bioconjugate Techniques, 1st ed., Academic Press (1996).
58 European Patent Publication No. 0 372 501.
59 European Patent Publication No. 0 378 881.
60 European Patent Publication No. 0 427 347.
61 International Publication No. WO 93/17712.
62 International Publication No. WO 98/58668.
63 European Patent Publication No. 0 471 177.
64 International Publication No. WO00/56360.
65 International Publication No. WO 00/67161.

The contents of all of the above cited patents, patent applications and journal articles are incorporated by reference as if set forth fully herein.

3. Immunological Adjuvants

As noted above, microparticle compositions and kits in accordance with the invention may include one or more immunological adjuvants. Immunological adjuvants for use with the invention include, but are not limited to, one or more of the following set forth below:

A. Mineral Containing Compositions

Mineral containing compositions suitable for use as immunological adjuvants include mineral salts, such as aluminum salts and calcium salts. The invention includes mineral salts such as hydroxides (e.g. oxyhydroxides), phosphates (e.g. hydroxyphosphates, orthophosphates), sulfates, etc. (see, e.g., Vaccine Design: The Subunit and Adjuvant Approach (Powell, M. F. and Newman, M. J. eds.) (New York: Plenum Press) 1995, Chapters 8 and 9), or mixtures of different mineral compounds (e.g. a mixture of a phosphate and a hydroxide adjuvant, optionally with an excess of the phosphate), with the compounds taking any suitable form (e.g. gel, crystalline, amorphous, etc.), and with adsorption to the salt(s) being preferred. The mineral containing compositions may also be formulated as a particle of metal salt (WO 00/23105).

Aluminum salts may be included in vaccines of the invention such that the dose of $Al^{3+}$ is between 0.2 and 1.0 mg per dose.

In one embodiment, the aluminum based adjuvant for use in the present invention is alum (aluminum potassium sulfate ($AlK(SO_4)_2$)), or an alum derivative, such as that formed in-situ by mixing an antigen in phosphate buffer with alum, followed by titration and precipitation with a base such as ammonium hydroxide or sodium hydroxide.

Another aluminum-based adjuvant for use in vaccine formulations of the present invention is aluminum hydroxide adjuvant ($Al(OH)_3$) or crystalline aluminum oxyhydroxide (AlOOH), which is an excellent adsorbant, having a surface area of approximately 500 $m^2/g$. In another embodiment, the aluminum based adjuvant is aluminum phosphate adjuvant ($AlPO_4$) or aluminum hydroxyphosphate, which contains phosphate groups in place of some or all of the hydroxyl groups of aluminum hydroxide adjuvant. Preferred aluminum phosphate adjuvants provided herein are amorphous and soluble in acidic, basic and neutral media.

In another embodiment, the adjuvant comprises both aluminum phosphate and aluminum hydroxide. In a more particular embodiment thereof, the adjuvant has a greater amount of aluminum phosphate than aluminum hydroxide, such as a ratio of 2:1, 3:1, 4:1, 5:1, 6:1, 7:1, 8:1, 9:1 or greater than 9:1, by weight aluminum phosphate to aluminum hydroxide. In another embodiment, aluminum salts in the vaccine are present at 0.4 to 1.0 mg per vaccine dose, or 0.4 to 0.8 mg per vaccine dose, or 0.5 to 0.7 mg per vaccine dose, or about 0.6 mg per vaccine dose.

Generally, the preferred aluminum-based adjuvant(s), or ratio of multiple aluminum-based adjuvants, such as aluminum phosphate to aluminum hydroxide is selected by optimization of electrostatic attraction between molecules such that the antigen carries an opposite charge as the adjuvant at the desired pH. For example, aluminum phosphate adjuvant (iep=4) adsorbs lysozyme, but not albumin at pH 7.4. Should albumin be the target, aluminum hydroxide adjuvant would be selected (iep 11.4). Alternatively, pretreatment of aluminum hydroxide with phosphate lowers its isoelectric point, making it a preferred adjuvant for more basic antigens.

B. Oil-Emulsions

Oil-emulsion compositions and formulations suitable for use as immunological adjuvants (with or without other specific immunostimulating agents such as muramyl peptides or bacterial cell wall components) include squalene-water emulsions, such as MF59 adjuvant (5% Squalene, 0.5% TWEEN80 (polyoxyethylene sorbitan monooleate), and 0.5% SPAN85 (sorbitan trioleate), formulated into submicron particles using a microfluidizer). See WO 90/14837. See also, Podda (2001) Vaccine 19: 2673-2680; Frey et al. (2003) Vaccine 21:4234-4237. MF59 adjuvant is used as the adjuvant in the FLUAD™ influenza virus trivalent subunit vaccine.

Adjuvants for use in the compositions include submicron oil-in-water emulsions. Preferred submicron oil-in-water emulsions for use herein are squalene/water emulsions optionally containing varying amounts of MTP-PE, such as a submicron oil-in-water emulsion containing 4-5% w/v squalene, 0.25-1.0% w/v TWEEN80 (polyoxyethylene sorbitan monooleate), and/or 0.25-1.0% SPAN85 (sorbitan trioleate), and, optionally, N-acetylmuramyl-L-alanyl-D-isogluatminyl-L-alanine-2-(1'-2'-dipalmitoyl-sn-glycero-3-huydroxyphosphophoryloxy)-ethylamine (MTP-PE), for example, the submicron oil-in-water emulsion known as MF59 adjuvant (WO 90/14837; U.S. Pat. Nos. 6,299,884; 6,451,325; and Ott et al., "MF59—Design and Evaluation of a Safe and Potent Adjuvant for Human Vaccines" in Vaccine Design: The Subunit and Adjuvant Approach (Powell, M. F. and Newman, M. J. eds.) (New York: Plenum Press) 1995, pp. 277-296). MF59 adjuvant contains 4-5% w/v Squalene (e.g. 4.3%), 0.25-0.5% w/v TWEEN80 (polyoxyethylene sorbitan monooleate), and 0.5% w/v SPAN85 (sorbitan trioleate) and optionally contains various amounts of MTP-PE, formulated into submicron particles using a microfluidizer such as Model 110Y microfluidizer (Microfluidics, Newton, Mass.). For example, MTP-PE may be present in an amount of about 0-500 jg/dose, more preferably 0-250 μg/dose and most preferably, 0-100 μg/dose. As used herein, the term "MF59-0" refers to the above submicron oil-in-water emulsion lacking MTP-PE, while the term MF59-MTP denotes a formulation that contains MTP-PE. For instance, "MF59-100" contains 100 jg MTP-PE per dose, and so on. MF69, another submicron oil-in-water emulsion for use herein, contains 4.3% w/v squalene, 0.25% w/v TWEEN80 (polyoxyethylene sorbitan monooleate), and 0.75% w/v SPAN85 (sorbitan trioleate) and optionally MTP-PE. Yet another submicron oil-in-water emulsion is MF75, also known as SAF, containing 10% squalene, 0.4% TWEEN 80 (polyoxyethylene sorbitan monooleate), 5% pluronic-blocked polymer L121, and thr-MDP, also microfluidized into a submicron emulsion. MF75-MTP denotes an MF75 formulation that includes MTP, such as from 100-400 μg MTP-PE per dose.

Submicron oil-in-water emulsions, methods of making the same and immunostimulating agents, such as muramyl peptides, for use in the compositions, are described in detail in WO 90/14837; U.S. Pat. Nos. 6,299,884; and 6,451,325.

Complete Freund's adjuvant (CFA) and incomplete Freund's adjuvant (IFA) may also be used as adjuvants in the invention.

c. Saponin Formulations

Saponin formulations are also suitable for use as immunological adjuvants in the invention. Saponins are a heterologous group of sterol glycosides and triterpenoid glycosides that are found in the bark, leaves, stems, roots and even flowers of a wide range of plant species. Saponins isolated from the bark of the *Quillaia saponaria* Molina tree have been widely studied as adjuvants. Saponins can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. Saponin adjuvant formulations include STIMULON® adjuvant (Antigenics, Inc., Lexington, Mass.).

Saponin compositions have been purified using High Performance Thin Layer Chromatography (HP-TLC) and Reversed Phase High Performance Liquid Chromatography (RP-HPLC). Specific purified fractions using these techniques have been identified, including QS7, QS17, QS18, QS21, QH-A, QH-B and QH-C. Preferably, the saponin is QS21. A method of production of QS21 is disclosed in U.S. Pat. No. 5,057,540. Saponin formulations may also comprise a sterol, such as cholesterol (see WO 96/33739).

Combinations of saponins and cholesterols can be used to form unique particles called Immunostimulating Complexes (ISCOMs). ISCOMs typically also include a phospholipid such as phosphatidylethanolamine or phosphatidylcholine. Any known saponin can be used in ISCOMs. Preferably, the ISCOM includes one or more of Quil A, QHA and QHC. ISCOMs are further described in EP 0 109 942, WO 96/11711 and WO 96/33739. Optionally, the ISCOMS may be devoid of (an) additional detergent(s). See WO 00/07621.

A review of the development of saponin based adjuvants can be found in Barr et al. (1998) *Adv. Drug Del. Rev.* 32:247-271. See also Sjolander et al. (1998)*Adv. Drug Del. Rev.* 32:321-338.

D. Virosomes and Virus Like Particles (VLPs)

Virosomes and Virus Like Particles (VLPs) are also suitable as immunological adjuvants. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, QB-phage (such as coat proteins), GA-phage, fr-phage, AP205 phage, and Ty (such as retrotransposon Ty protein p1). VLPs are discussed further in WO 03/024480; WO 03/024481; Niikura et al. (2002) Virology 293:273-280; Lenz et al. (2001) J. Immunol. 166(9):5346-5355; Pinto et al. (2003) J. Infect. Dis. 188:327-338; and Gerber et al. (2001) J. Virol. 75(10):4752-4760. Virosomes are discussed further in, for example, Gluck et al. (2002) Vaccine 20:B10-B16. Immunopotentiating reconstituted influenza virosomes (IRIV) are used as the subunit antigen delivery system in the intranasal trivalent INFLEXAL™ influenza vaccine product (Mischler and Metcalfe (2002) Vaccine 20 Suppl 5:B17-B23) and the INFLUVAC PLUS™ influenza vaccine product.

E. Bacterial or Microbial Derivatives

Immunological adjuvants suitable for use in the invention include bacterial or microbial derivatives such as:

(1) Non-toxic derivatives of enterobacterial lipopolysaccharide (LPS): Such derivatives include Monophosphoryl lipid A (MPL) and 3-O-deacylated MPL (3dMPL). 3dMPL is a mixture of 3 De-O-acylated monophosphoryl lipid A with 4, 5 or 6 acylated chains. A preferred "small particle" form of 3 De-O-acylated monophosphoryl lipid A is disclosed in EP 0 689 454. Such "small particles" of 3dMPL are small enough to be sterile filtered through a 0.22 micron membrane (see EP 0 689 454). Other non-toxic LPS derivatives include monophosphoryl lipid A mimics, such as aminoalkyl glucosaminide phosphate derivatives, e.g., RC-529. See Johnson et al. (1999) Bioorg. Med. Chem. Lett. 9:2273-2278.

(2) Lipid A Derivatives: Lipid A derivatives include derivatives of lipid A from Escherichia coli such as OM-174. OM-174 is described for example in Meraldi et al. (2003) Vaccine 21:2485-2491; and Pajak et al. (2003) Vaccine 21:836-842.

(3) Immunostimulatory oligonucleotides: Immunostimulatory oligonucleotides or polymeric molecules suitable for use as adjuvants in the invention include nucleotide sequences containing a CpG motif (a sequence containing an unmethylated cytosine followed by guanosine and linked by a phosphate bond). Bacterial double stranded RNA or oligonucleotides containing palindromic or poly(dG) sequences have also been shown to be immunostimulatory. The CpG's can include nucleotide modifications/analogs such as phosphorothioate modifications and can be double-stranded or single-stranded. Optionally, the guanosine may be replaced with an analog such as 2'-deoxy-7-deazaguanosine. See Kandimalla et al. (2003) Nucl. Acids Res. 31(9): 2393-2400; WO 02/26757; and WO 99/62923 for examples of possible analog substitutions. The adjuvant effect of CpG oligonucleotides is further discussed in Krieg (2003) Nat. Med. 9(7):831-835; McCluskie et al. (2002) FEMS Immunol. Med. Microbiol. 32:179-185; WO 98/40100; U.S. Pat. Nos. 6,207,646; 6,239,116; and 6,429,199. The CpG sequence may be directed to TLR9, such as the motif GTCGTT or TTCGTT. See Kandimalla et al. (2003) Biochem. Soc. Trans. 31 (part 3):654-658. The CpG sequence may be specific for inducing a Th1 immune response, such as a CpG-A ODN, or it may be more specific for inducing a B cell response, such a CpG-B ODN. CpG-A and CpG-B ODNs are discussed in Blackwell et al. (2003)J. Immunol. 170(8):4061-4068; Krieg (2002) TRENDS Immunol. 23(2): 64-65; and WO 01/95935. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, Kandimalla et al. (2003) BBRC 306:948-953; Kandimalla et al. (2003) Biochem. Soc. Trans. 31 (part 3):664-658; Bhagat et al. (2003) BBRC 300:853-861; and WO03/035836.

Immunostimulatory oligonucleotides and polymeric molecules also include alternative polymer backbone structures such as, but not limited to, polyvinyl backbones (Pitha et al. (1970) Biochem. Biophys. Acta 204(1):39-48; Pitha et al. (1970) Biopolymers 9(8):965-977), and morpholino backbones (U.S. Pat. Nos. 5,142,047; 5,185,444). A variety of other charged and uncharged polynucleotide analogs are known in the art. Numerous backbone modifications are known in the art, including, but not limited to, uncharged linkages (e.g., methyl phosphonates, phosphotriesters, phosphoamidates, and carbamates) and charged linkages (e.g., phosphorothioates and phosphorodithioates).

(4) ADP-ribosylating toxins and detoxified derivatives thereof: Bacterial ADP-ribosylating toxins and detoxified derivatives thereof may be used as adjuvants in the invention. Preferably, the protein is derived from E. coli (i.e., E. coli heat labile enterotoxin "LT"), cholera ("CT"), or pertussis ("PT"). The use of detoxified ADP-ribosylating toxins as mucosal adjuvants is described in WO 95/17211 and as parenteral adjuvants in WO 98/42375. Preferably, the adjuvant is a detoxified LT mutant such as LT-K63, LT-R72, and LTR192G. The use of ADP-ribosylating toxins and detoxified derivatives thereof, particularly LT-K63 and LT-R72, as adjuvants can be found in the following references: Beignon et al. (2002) Infect. Immun. 70(6):3012-3019; Pizza et al. (2001) Vaccine 19:2534-2541; Pizza et al. (2000) Int. J. Med. Microbiol. 290(4-5):455-461; Scharton-Kersten et al. (2000) Infect. Immun. 68(9):5306-5313; Ryan et al. (1999) Infect. Immun. 67(12):6270-6280; Partidos et al. (1999) Immunol. Lett. 67(3):209-216; Peppoloni et al. (2003) Vaccines 2(2):285-293; and Pine et al. (2002) J. Control Release 85(1-3):263-270. Numerical reference for amino acid substitutions is preferably based on the alignments of the A and B subunits of ADP-ribosylating toxins set forth in Domenighini et al. (1995) Mol. Microbiol. 15(6):1165-1167.

Compounds of formula I, II or III, or salts thereof, can also be used as adjuvants:

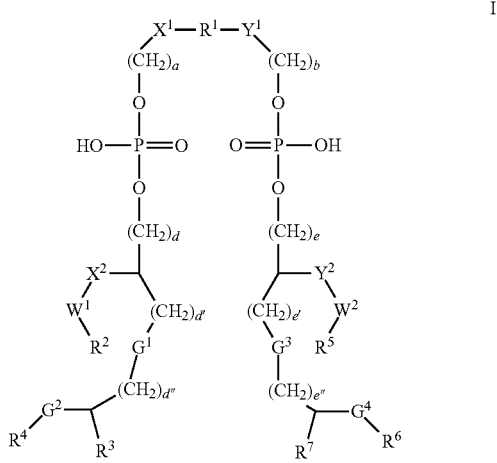

I

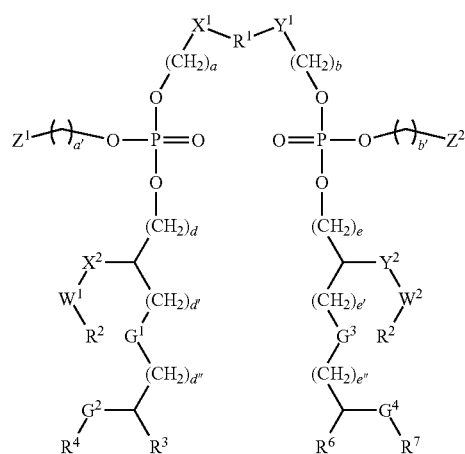
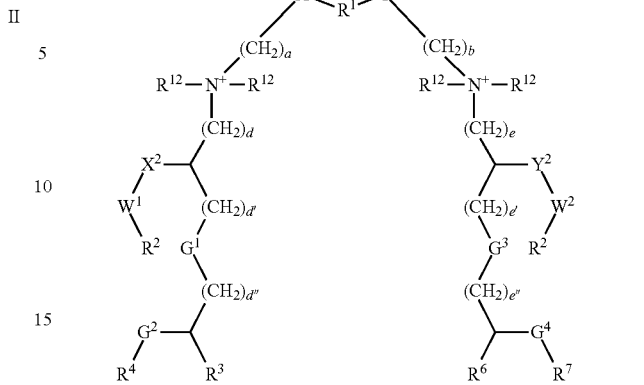
as defined in WO03/011223, such as 'ER 803058', 'ER 803732', 'ER 804053', ER 804058', 'ER 804059', 'ER 804442', 'ER 804680', 'ER 804764', ER 803022 or 'ER 804057' e.g.:
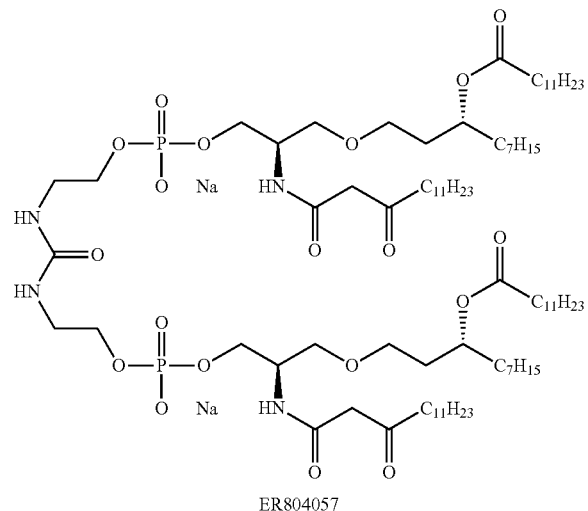
ER804057
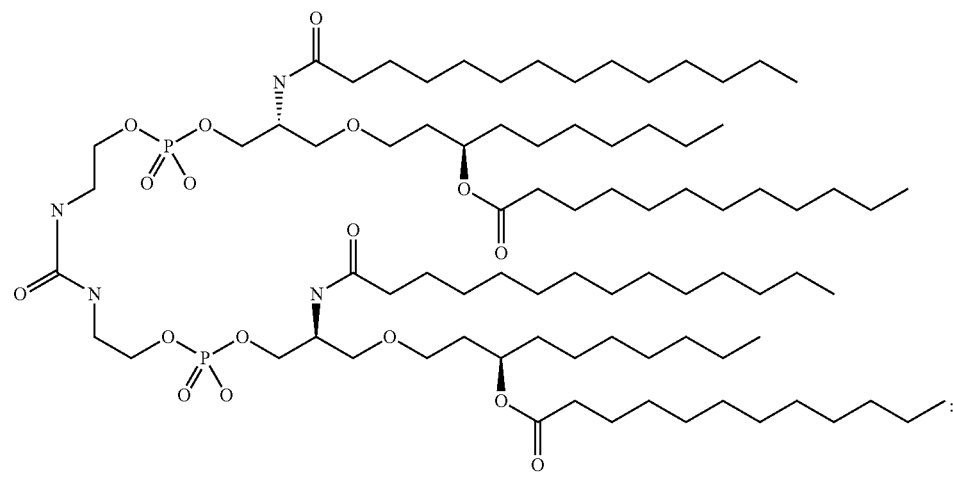
ER-803022

F. Human Immunomodulators

Human immunomodulators suitable for use as immunological adjuvants include cytokines, such as interleukins (e.g. IL-1, IL-2, IL-4, IL-5, IL-6, IL-7, IL-12, etc.), interferons (e.g. interferon-γ), macrophage colony stimulating factor (M-CSF), and tumor necrosis factor (TNF).

G. Bioadhesives and Mucoadhesives

Bioadhesives and mucoadhesives may also be used as immunological adjuvants. Suitable bioadhesives include esterified hyaluronic acid microspheres (Singh et al. (2001) *J. Cont. Release* 70:267-276) or mucoadhesives such as cross-linked derivatives of polyacrylic acid, polyvinyl alcohol, polyvinyl pyrollidone, polysaccharides and carboxymethylcellulose. Chitosan and derivatives thereof may also be used as adjuvants in the invention (see WO 99/27960).

H. Liposomes

Examples of liposome formulations suitable for use as immunological adjuvants are described in U.S. Pat. Nos. 6,090,406; 5,916,588; and EP Patent Publication No. EP 0 626 169.

I. Polyoxyethylene Ether and Polyoxyethylene Ester Formulations

Immunological adjuvants suitable for use in the invention include polyoxyethylene ethers and polyoxyethylene esters (see, e.g., WO 99/52549). Such formulations further include polyoxyethylene sorbitan ester surfactants in combination with an octoxynol (WO 01/21207) as well as polyoxyethylene alkyl ethers or ester surfactants in combination with at least one additional non-ionic surfactant such as an octoxynol (WO 01/21152).

Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

J. Polyphosphazene (PCPP)

PCPP formulations suitable for use as immunological adjuvants are described, for example, in Andrianov et al. (1998) *Biomaterials* 19(1-3):109-115; and Payne et al. (1998) *Adv. Drug Del. Rev.* 31(3):185-196.

K. Muramyl Peptides

Examples of muramyl peptides suitable for use as immunological adjuvants include N-acetyl-muramyl-L-threonyl-D-isoglutamine (thr-MDP), N-acetyl-normuramyl-1-alanyl-d-isoglutamine (nor-MDP), and N-acetylmuramyl-1-alanyl-d-isoglutaminyl-1-alanine-2-(1'-2'-dipalmitoyl-sn-glycero-3-hydroxyphosphoryloxy)-ethylamine MTP-PE).

L. Imidazoquinoline Compounds

Examples of imidazoquinoline compounds suitable for use as immunological adjuvants include Imiquimod and its analogues, which are described further in Stanley (2002) *Clin. Exp. Dermatol.* 27(7):571-577; Jones (2003) *Curr. Opin. Investig. Drugs* 4(2):214-218; and U.S. Pat. Nos. 4,689,338; 5,389,640; 5,268,376; 4,929,624; 5,266,575; 5,352,784; 5,494,916; 5,482,936; 5,346,905; 5,395,937; 5,238,944; and 5,525,612.

Imidazoquinolines for the practice of the present invention include imiquimod, resiquimod, and

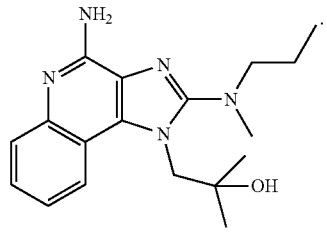 [SMILES: CCCN(C)c1nc2c(N)nc3ccccc3c2n1CC(C)(C)O]

See, e.g., International Publication Nos. WO 2006/031878 and WO 2007/109810. Such compounds are known to be TLR7 agonists.

M. Thiosemicarbazone Compounds

Examples of thiosemicarbazone compounds suitable for use as immunological adjuvants, as well as methods of formulating, manufacturing, and screening for such compounds, include those described in WO 04/60308. The thiosemicarbazones are particularly effective in the stimulation of human peripheral blood mononuclear cells for the production of cytokines, such as TNF-α.

N. Tryptanthrin Compounds

Examples of tryptanthrin compounds suitable for use as immunological adjuvants, as well as methods of formulating, manufacturing, and screening for such compounds, include those described in WO 04/64759. The tryptanthrin compounds are particularly effective in the stimulation of human peripheral blood mononuclear cells for the production of cytokines, such as TNF-α.

O. Nucleoside Analogs

Various nucleoside analogs can be used as immunological adjuvants, such as (a) Isatorabine (ANA-245; 7-thia-8-oxoguanosine):

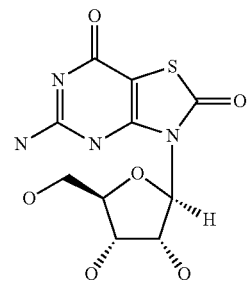 [SMILES: Nc1nc(=O)c2sc(=O)n([C@@H]3O[C@H](CO)[C@@H](O)[C@H]3O)c2[nH]1]

an U d prodrugs thereof; (b) ANA975; (c) ANA-025-1; (d) ANA380; (e) the compounds disclosed in U.S. Pat. No. 6,924,271; U.S. Publication No. 2005/0070556; and U.S. Pat. No. 5,658,731; (f) a compound having the formula:

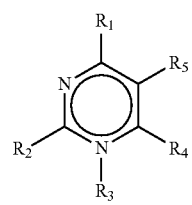

wherein:
- R$_1$ and R$_2$ are each independently H, halo, —NR$_a$R$_b$, —OH, C$_{1-6}$ alkoxy, substituted C$_{1-6}$ alkoxy, heterocyclyl, substituted heterocyclyl, C$_{6-10}$ aryl, substituted C$_{6-10}$ aryl, C$_{1-6}$ alkyl, or substituted C$_{1-6}$ alkyl;
- R$_3$ is absent, H, C$_{1-6}$ alkyl, substituted C$_{1-6}$ alkyl, C$_{6-10}$ aryl, substituted C$_{6-10}$ aryl, heterocyclyl, or substituted heterocyclyl;
- R$_4$ and R$_5$ are each independently H, halo, heterocyclyl, substituted heterocyclyl, —C(O)—Rd, C$_{1-6}$ alkyl, substituted C$_{1-6}$ alkyl, or bound together to form a 5 membered ring as in R$_{4-5}$:

$$R_{4-5}$$

the binding being achieved at the bonds indicated by a ∼∼∼

X$_1$ and X$_2$ are each independently N, C, O, or S;

R$_8$ is H, halo, —OH, C$_{1-6}$ alkyl, C$_{2-6}$ alkenyl, C$_{2-6}$ alkynyl, —OH, —NR$_a$R$_b$, —(CH$_2$)$_n$—O—R$_c$, —O—(C$_{1-6}$ alkyl), —S(O)$_p$R$_e$, or —C(O)—R$_d$;

R$_9$ is H, C$_{1-6}$ alkyl, substituted C$_{1-6}$ alkyl, heterocyclyl, substituted heterocyclyl or R$_{9a}$, wherein R$_{9a}$ is:

$$R_{9a}$$

the binding being achieved at the bond indicated by a ∼∼∼

R$_{10}$ and R$_{11}$ are each independently H, halo, C$_{1-6}$ alkoxy, substituted C$_{1-6}$ alkoxy, —NR$_a$R$_b$, or —OH;

each R$_a$ and R$_b$ is independently H, C$_{1-6}$ alkyl, substituted C$_{1-6}$ alkyl, —C(O)R$_d$, C$_{6-10}$ aryl;

each R$_c$ is independently H, phosphate, diphosphate, triphosphate, C$_{1-6}$ alkyl, or substituted C$_{1-6}$ alkyl;

each R$_d$ is independently H, halo, C$_{1-6}$ alkyl, substituted C$_{1-6}$ alkyl, C$_{1-6}$ alkoxy, substituted C$_{1-6}$ alkoxy, —NH$_2$, —NH(C$_{1-6}$ alkyl), —NH(substituted C$_{1-6}$ alkyl), —N(C$_{1-6}$ alkyl)$_2$, —N(substituted C$_{1-6}$ alkyl)$_2$, C$_{6-10}$ aryl, or heterocyclyl;

each R$_e$ is independently H, C$_{1-6}$ alkyl, substituted C$_{1-6}$ alkyl, C$_{6-10}$ aryl, substituted C$_{6-10}$ aryl, heterocyclyl, or substituted heterocyclyl;

each R$_f$ is independently H, C$_{1-6}$ alkyl, substituted C$_{1-6}$ alkyl, —C(O)R$_d$, phosphate, diphosphate, or triphosphate;

each n is independently 0, 1, 2, or 3;

each p is independently 0, 1, or 2; or or (g) a pharmaceutically acceptable salt of any of (a) to (f), a tautomer of any of (a) to (f), or a pharmaceutically acceptable salt of the tautomer.

P. Lipids Linked to a Phosphate-Containing Acyclic Backbone

Immunological adjuvants containing lipids linked to a phosphate-containing acyclic backbone include the TLR4 antagonist E5564 (Wong et al. (2003) *J. Clin. Pharmacol.* 43(7):735-742; US2005/0215517):

Q. Small Molecule Immunopotentiators (SMIPs)
SMIPs include:
N2-methyl-1-(2-methylpropyl)-1H-imidazo[4,5-c]quinoline-2,4-diamine;
N2,N2-dimethyl-1-(2-methylpropyl)-1H-imidazo[4,5-c]quinoline-2,4-diamine;
N2-ethyl-N2-methyl-1-(2-methylpropyl)-1H-imidazo[4,5-c]quinoline-2,4-diamine;
N2-methyl-1-(2-methylpropyl)-N2-propyl-1H-imidazo[4,5-c]quinoline-2,4-diamine;
1-(2-methylpropyl)-N2-propyl-1H-imidazo[4,5-c]quinoline-2,4-diamine;
N2-butyl-1-(2-methylpropyl)-1H-imidazo[4,5-c]quinoline-2,4-diamine;
N2-butyl-N2-methyl-1-(2-methylpropyl)-1H-imidazo[4,5-c]quinoline-2,4-diamine;
N2-methyl-1-(2-methylpropyl)-N2-pentyl-1H-imidazo[4,5-c]quinoline-2,4-diamine;
N2-methyl-1-(2-methylpropyl)-N2-prop-2-enyl-1H-imidazo[4,5-c]quinoline-2,4-diamine;
1-(2-methylpropyl)-2-[(phenylmethyl)thio]-1H-imidazo[4,5-c]quinolin-4-amine;
1-(2-methylpropyl)-2-(propylthio)-1H-imidazo[4,5-c]quinolin-4-amine;
2-[[4-amino-1-(2-methylpropyl)-1H-imidazo[4,5-c]quinolin-2-yl](methyl)amino]ethanol;
2-[[4-amino-1-(2-methylpropyl)-1H-imidazo[4,5-c]quinolin-2-yl](methyl)amino]ethyl acetate;

4-amino-1-(2-methylpropyl)-1,3-dihydro-2H-imidazo[4,5-c]quinolin-2-one;
N2-butyl-1-(2-methylpropyl)-N4,N4-bis(phenylmethyl)-1H-imidazo[4,5-c]quinoline-2,4-diamine;
N2-butyl-N2-methyl-1-(2-methylpropyl)-N4,N4-bis(phenylmethyl)-1H-imidazo[4,5-c]quinoline-2,4-diamine;
N2-methyl-1-(2-methylpropyl)-N4,N4-bis(phenylmethyl)-1H-imidazo[4,5-c]quinoline-2,4-diamine;
N2,N2-dimethyl-1-(2-methylpropyl)-N4,N4-bis(phenylmethyl)-1H-imidazo[4,5-c]quinoline-2,4-diamine;
1-{4-amino-2-[methyl(propyl)amino]-1H-imidazo[4,5-c]quinolin-1-yl}-2-methylpropan-2-ol;
1-[4-amino-2-(propylamino)-1H-imidazo[4,5-c]quinolin-1-yl]-2-methylpropan-2-ol;
N4,N4-dibenzyl-1-(2-methoxy-2-methylpropyl)-N2-propyl-1H-imidazo[4,5-c]quinoline-2,4-diamine.

R. Proteosomes

One adjuvant is an outer membrane protein proteosome preparation prepared from a first Gram-negative bacterium in combination with a liposaccharide preparation derived from a second Gram-negative bacterium, wherein the outer membrane protein proteosome and liposaccharide preparations form a stable non-covalent adjuvant complex. Such complexes include "IVX-908", a complex comprised of Neisseria meningitidis outer membrane and lipopolysaccharides. They have been used as adjuvants for influenza vaccines (WO02/072012).

s. Lipopeptides

Lipopeptides (i.e., compounds comprising one or more fatty acid residues and two or more amino acid residues) are also known to have immunostimulating character. Lipopeptides based on glycerylcysteine are particularly suitable for use as adjuvants. Specific examples of such peptides include compounds of the following formula

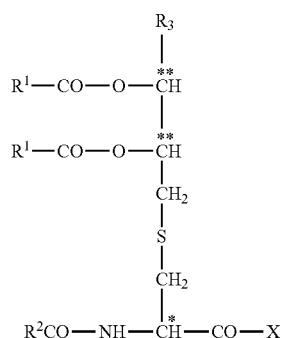

* = R
** = R or S in which each of $R^1$ and $R^2$ represents a saturated or unsaturated, aliphatic or mixed aliphatic-cycloaliphatic hydrocarbon radical having from 8 to 30, preferably 11 to 21, carbon atoms that is optionally also substituted by oxygen functions, $R^3$ represents hydrogen or the radical $R_1$—CO—O—$CH_2$— in which R' has the same meaning as above, and X represents an amino acid bonded by a peptide linkage and having a free, esterified or amidated carboxy group, or an amino acid sequence of from 2 to 10 amino acids of which the terminal carboxy group is in free, esterified or amidated form. In certain embodiments, the amino acid sequence comprises a D-amino acid, for example, D-glutamic acid (D-Glu) or D-gamma-carboxyglutamic acid (D-Gla).

Bacterial lipopeptides generally recognize TLR2, without requiring TLR6 to participate. (TLRs operate cooperatively to provide specific recognition of various triggers, and TLR2 plus TLR6 together recognize peptidoglycans, while TLR2 recognizes lipopeptides without TLR6.) These are sometimes classified as natural lipopeptides and synthetic lipopeptides. Synthetic lipopeptides tend to behave similarly, and are primarily recognized by TLR2.

Lipopeptides suitable for use as adjuvants include compounds of Formula I:

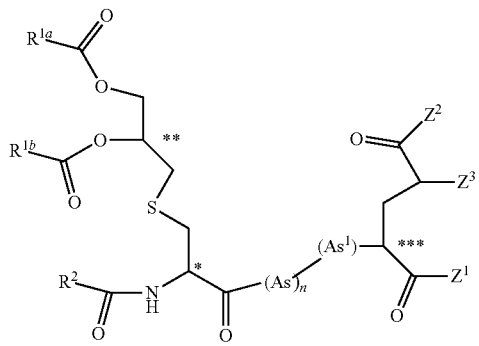

where the chiral center labeled * and the one labeled *** are both in the R configuration;

the chiral center labeled ** is either in the R or S configuration;

each $R^{1a}$ and $R^{1b}$ is independently an aliphatic or cycloaliphatic-aliphatic hydrocarbon group having 7-21 carbon atoms, optionally substituted by oxygen functions, or one of $R^{1a}$ and $R^{1b}$, but not both, is H;

$R^2$ is an aliphatic or cycloaliphatic hydrocarbon group having 1-21 carbon atoms and optionally substituted by oxygen functions;

n is 0 or 1;

As represents either —O-Kw-CO— or —NH-Kw-CO—, where Kw is an aliphatic hydrocarbon group having 1-12 carbon atoms;

$As^1$ is a D- or L-alpha-amino acid;

$Z^1$ and $Z^2$ each independently represent —OH or the N-terminal radical of a D- or L-alpha amino acid of an amino-(lower alkane)-sulfonic acid or of a peptide having up to 6 amino acids selected from the D- and L-alpha aminocarboxylic acids and amino-lower alkyl-sulfonic acids; and $Z^3$ is H or —CO—$Z^4$, where $Z^4$ is —OH or the N-terminal radical of a D- or L-alpha amino acid of an amino-(lower alkane)-sulfonic acid or of a peptide having up to 6 amino acids selected from the D and L-alpha aminocarboxylic acids and amino-lower alkyl-sulfonic acids; or an ester or amide formed from the carboxylic acid of such compounds. Suitable amides include —$NH_2$ and NH(lower alkyl), and suitable esters include $C_1$-$C_4$ alkyl esters. (lower alkyl or lower alkane, as used herein, refers to $C_1$-$C_6$ straight chain or branched alkyls).

Such compounds are described in more detail in U.S. Pat. No. 4,666,886. In one preferred embodiment, the lipopeptide is of the following formula:

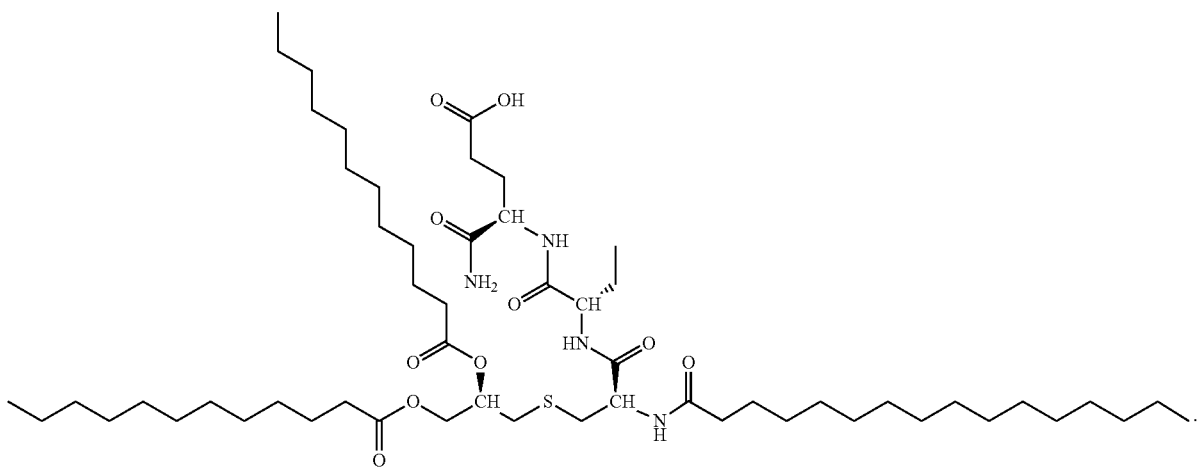 [SMILES: CCCCCCCCCCCCCCCC(=O)N[C@@H](CSC[C@@H](COC(=O)CCCCCCCCCCC)OC(=O)CCCCCCCCCCC)C(=O)N[C@@H](CC)C(=O)N[C@H](CCC(=O)O)C(N)=O]

Another example of a lipopeptide species is called LP40, and is an agonist of TLR2 (Akdis, et al., *Eur. J. Immunology*, 33: 2717-2726 (2003)).

These are related to a known class of lipopeptides from *E. coli*, referred to as murein lipoproteins. Certain partial degradation products of those proteins called murein lipopetides are described in Hantke, et al. (*Eur. J. Biochem.*, 34: 284-296 (1973)). These comprise a peptide linked to N-acetyl muramic acid and are thus related to Muramyl peptides, which are described in Baschang, et al. (*Tetrahedron*, 45(20): 6331-6360 (1989)).

T. Benzonaphthyridines

Examples of benzonaphthyridine compounds suitable for use as adjuvants include compounds having the structure of Formula (I), and pharmaceutically acceptable salts, solvates, N-oxides, prodrugs and isomers thereof:

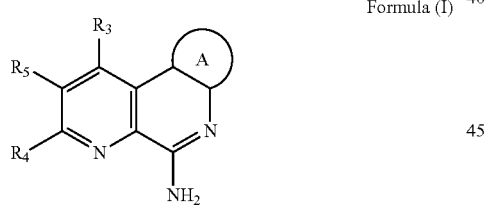

Formula (I)

wherein:

$R^3$ is H, halogen, $C_1$-$C_6$alkyl, $C_2$-$C_8$alkene, $C_2$-$C_8$alkyne, $C_1$-$C_6$heteroalkyl, $C_1$-$C_6$haloalkyl, $C_1$-$C_6$alkoxy, $C_1$-$C_6$haloalkoxy, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, $C_1$-$C_6$alkoxy, $C_1$-$C_6$haloalkoxy, $C_3$-$C_8$cycloalkyl, or $C_3$-$C_8$heterocycloalkyl groups of $R^3$ are each optionally substituted with 1 to 3 substituents independently selected from halogen, —CN, —$R^7$, —$OR^8$, —$C(O)R^8$, —$OC(O)R^8$, —$C(O)OR^8$, —$N(R^9)_2$, —$C(O)N(R^9)_2$, —$S(O)_2R^8$, —$S(O)_2N(R^9)_2$ and —$NR^9S(O)_2R^8$;

$R^4$ and $R^5$ are each independently selected from H, halogen, —$C(O)OR^7$, —$C(O)R^7$, —$C(O)N(R^{11}R^{12})$, —$N(R^{11}R^{12})$, —$N(R^9)_2$, —$NHN(R^9)_2$, —$SR^7$, —$(CH_2)_nOR^7$, —$(CH_2)_nR^7$, -$LR^8$, -$LR^{10}$, —$OLR^8$, -$OLR^{10}$, $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, aryl, heteroaryl, $C_3$-$C_8$cycloalkyl, and $C_3$-$C_8$heterocycloalkyl groups of $R^4$ and $R^5$ are each optionally substituted with 1 to 3 substituents independently selected from halogen, —CN, —$NO_2$, —$R^7$, —$OR^8$, —$C(O)R^8$, —$OC(O)R^8$, —$C(O)OR^8$, —$N(R^9)_2$, —$P(O)(OR^8)_2$, —$OP(O)(OR^8)_2$, —$P(O)(OR^{10})_2$, —$OP(O)(OR^{10})_2$, —$C(O)N(R^9)_2$, —$S(O)_2R^8$, —$S(O)R^8$, —$S(O)_2N(R^9)_2$, and —$NR^9S(O)_2R^8$;

or $R^3$ and $R^4$, or $R^4$ and $R^5$, when present on adjacent ring atoms, can optionally be linked together to form a 5-6 membered ring, wherein the 5-6 membered ring is optionally substituted with $R^7$;

each L is independently selected from a bond, —$O(CH_2)_m)_t$—, $C_1$-$C_6$alkyl, $C_2$-$C_6$alkenylene and $C_2$-$C_6$alkynylene, wherein the $C_1$-$C_6$alkyl, $C_2$-$C_6$alkenylene and $C_2$-$C_6$alkynylene of L are each optionally substituted with 1 to 4 substituents independently selected from halogen, —$R^8$, —$OR^8$, —$N(R^9)_2$, —$P(O)(OR^8)_2$, —$OP(O)(OR^8)_2$, —$P(O)(OR^{10})_2$, and —$OP(O)(OR^{10})_2$;

$R^7$ is selected from H, $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl, wherein the $C_1$-$C_6$alkyl, aryl, heteroaryl, $C_3$-$C_8$cycloalkyl, $C_1$-$C_6$heteroalkyl, $C_1$-$C_6$haloalkyl, $C_2$-$C_8$alkene, $C_2$-$C_8$alkyne, $C_1$-$C_6$alkoxy, $C_1$-$C_6$haloalkoxy, and $C_3$-$C_8$heterocycloalkyl groups of $R^7$ are each optionally substituted with 1 to 3 $R^{13}$ groups;

each $R^8$ is independently selected from H, —$CH(R^{10})_2$, $C_1$-$C_8$alkyl, $C_2$-$C_8$alkene, $C_2$-$C_8$alkyne, $C_1$-$C_6$haloalkyl, $C_1$-$C_6$alkoxy, $C_1$-$C_6$heteroalkyl, $C_3$-$C_8$cycloalkyl, $C_2$-$C_8$heterocycloalkyl, $C_1$-$C_6$hydroxyalkyl and $C_1$-$C_8$haloalkoxy, wherein the $C_1$-$C_8$alkyl, $C_2$-$C_8$alkene, $C_2$-$C_8$alkyne, $C_1$-$C_6$heteroalkyl, $C_1$-$C_6$haloalkyl, $C_1$-$C_6$alkoxy, $C_3$-$C_8$cycloalkyl, $C_2$-$C_8$heterocycloalkyl, $C_1$-$C_6$hydroxyalkyl and $C_1$-$C_6$haloalkoxy groups of $R^8$ are each optionally substituted with 1 to 3 substituents independently selected from —CN, $R^{11}$, —$OR^{11}$, —$SR^{11}$, —$C(O)R^{11}$, —$OC(O)R^{11}$, —$C(O)N(R^9)_2$, —$C(O)OR^{11}$, —$NR^9C(O)R^{11}$, —$NR^9R^{10}$, —$NR^{11}R^{12}$, —$N(R^9)_2$, —$OR^9$, —$OR^{10}$, —$C(O)NR^{11}R^{12}$, —$C(O)NR^{11}OH$, —$S(O)_2R^{11}$, —$S(O)R^{11}$, —$S(O)_2NR^{11}R^{12}$, —$NR^{11}S(O)_2R^{11}$, —$P(O)(OR^{11})_2$, and —$OP(O)(OR^{11})_2$;

each $R^9$ is independently selected from H, —$C(O)R^8$, —$C(O)OR^8$, —$C(O)R^{10}$, —$C(O)OR^{11}$, —$S(O)_2R^{10}$, —$C_1$-$C_6$ alkyl, $C_1$-$C_6$ heteroalkyl and $C_3$-$C_6$ cycloalkyl, or each $R^9$ is independently a $C_1$-$C_6$alkyl that together with N they are attached to form a $C_3$-$C_8$heterocycloalkyl, wherein the $C_3$-$C_8$heterocycloalkyl ring optionally contains an additional heteroatom selected from N, O and S, and wherein the $C_1$-$C_6$ alkyl, $C_1$-$C_6$ heteroalkyl, $C_3$-$C_6$ cycloalkyl, or $C_3$-$C_8$heterocycloalkyl groups of $R^9$ are each optionally substituted with 1 to 3 substituents independently selected from —CN, $R^{11}$, —$OR^{11}$, —$SR^{11}$, —$C(O)R^{11}$, —$OC(O)R^{11}$, —$C(O)OR^{11}$, —$NR^{11}R^{12}$, —$C(O)NR^{11}R^{12}$, —$C(O)NR^{11}OH$, —$S(O)_2R^{11}$, —$S(O)R^{11}$, —$S(O)_2NR^{11}R^{12}$, —$NR^{11}S(O)_2R^{11}$, —$P(O)(OR^{11})_2$, and —$OP(O)(OR^{11})_2$;

each $R^{10}$ is independently selected from aryl, $C_3$-$C_8$cycloalkyl, $C_3$-$C_8$heterocycloalkyl and heteroaryl, wherein the aryl, $C_3$-$C_8$cycloalkyl, $C_3$-$C_8$heterocycloalkyl and heteroaryl groups are optionally substituted with 1 to 3 substituents selected from halogen, —$R^8$, —$OR^8$, -$LR^9$, -$LOR^9$, —$N(R^9)_2$, —$NR^9C(O)R^8$, —$NR^9CO_2R^8$, —$CO_2R^8$, —$C(O)R^8$ and —$C(O)N(R^9)_2$; $R^{11}$ and $R^{12}$ are independently selected from H, $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl, wherein the $C_1$-$C_6$alkyl, $C_1$-$C_6$heteroalkyl, $C_1$-$C_6$haloalkyl, aryl, heteroaryl, $C_3$-$C_8$cycloalkyl, and $C_3$-$C_8$heterocycloalkyl groups of $R^{11}$ and $R^{12}$ are each optionally substituted with 1 to 3 substituents independently selected from halogen, —CN, $R^8$, —$OR^8$, —$C(O)R^8$, $OC(O)R^8$, —$C(O)OR^8$, —$N(R^9)_2$, —$NR^8C(O)R^8$, —$NR^8C(O)OR^8$, —$C(O)N(R^9)_2$, $C_3$-$C_8$heterocycloalkyl, —$S(O)_2R^8$, —$S(O)_2N(R^9)_2$, —$NR^9S(O)_2R^8$, $C_1$-$C_6$haloalkyl and $C_1$-$C_6$haloalkoxy;

or $R^{11}$ and $R^{12}$ are each independently $C_1$-$C_6$alkyl and taken together with the N atom to which they are attached form an optionally substituted $C_3$-$C_8$heterocycloalkyl ring optionally containing an additional heteroatom selected from N, O and S;

each $R^{13}$ is independently selected from halogen, —CN, -$LR^9$, -$LOR^9$, —$OLR^9$, -$LR^{10}$, -$LOR^{10}$, —$OLR^{10}$, -$LR^8$, -$LOR^8$, -$OLR^8$, -$LSR^8$, -$LSR^{10}$, -$LC(O)R^8$, -$OLC(O)R^8$, -$LC(O)OR^8$, -$LC(O)R^{10}$, -$LOC(O)OR^8$, -$LC(O)NR^9R^{11}$, -$LC(O)NR^9R^8$, -$LN(R^9)_2$, -$LNR^9R^8$, -$LNR^9R^{10}$, -$L=NOH$, -$LC(O)N(R^9)_2$, -$LS(O)_2R^8$, -$LS(O)R^8$, -$LC(O)NR^8OH$, -$LNR^9C(O)R^8$, -$LNR^9C(O)OR^8$, -$LS(O)_2N(R^9)_2$, $OLS(O)_2N(R^9)_2$, -$LNR^9S(O)_2R^8$, -$LC(O)NR^9LN(R^9)_2$, -$LP(O)(OR^8)_2$, -$LOP(O)(OR^8)_2$, -$LP(O)(OR^{11}O)_2$ and —$OLP(O)(OR^{10})_2$;

Ring A is an aryl or a heteroaryl, wherein the aryl and heteroaryl groups of Ring A are optionally substituted with 1 to 3 $R^A$ groups, wherein each $R^A$ is independently selected from halogen, —$R^8$, —$R^7$, —$OR^7$, —$OR^8$, —$R^{10}$, —$OR^{10}$, —$SR^8$, —$NO_2$, —CN, —$N(R^9)_2$, —$NR^9C(O)R^8$, —$NR^9C(S)R^8$, —$NR^9C(O)N(R^9)_2$, —$NR^9C(S)N(R^9)_2$, —$NR^9CO_2R^8$, —$NR^9NR^9C(O)R^8$, —$NR^9NR^9C(O)N(R^9)_2$, —$NR^9NR^9CO_2R^8$, —$C(O)C(O)R^8$, —$C(O)CH_2C(O)R^8$, —$CO_2R^8$, —$(CH_2)_nCO_2R^8$, —$C(O)R^8$, —$C(S)R^8$, —$C(O)N(R^9)_2$, —$C(S)N(R^9)_2$, —$OC(O)N(R^9)_2$, —$OC(O)R^8$, —$C(O)N(OR^8)R^8$, —$C(NOR^8)R^8$, —$S(O)_2R^8$, —$S(O)_3R^8$, —$SO_2N(R^9)_2$, —$S(O)R^8$, —$NR^9SO_2N(R^9)_2$, —$NR^9SO_2R^8$, —$P(O)(OR^8)_2$, —$OP(O)(OR^8)_2$, —$P(O)(OR^{10})_2$, —$OP(O)(OR^{10})_2$, —$N(OR^8)R^8$, —$CH=CHCO_2R^8$, —$C(=NH)$—$N(R^9)_2$, and —$(CH_2)_nNHC(O)R^8$; or two adjacent $R^A$ substituents on Ring A form a 5-6 membered ring that contains up to two heteroatoms as ring members;

n is, independently at each occurrence, 0, 1, 2, 3, 4, 5, 6, 7 or 8;

each m is independently selected from 1, 2, 3, 4, 5 and 6, and t is 1, 2, 3, 4, 5, 6, 7 or 8.

In certain embodiments of compounds of Formulas (I), ring A an aromatic ring, such as phenyl, pyridyl, or pyrimidinyl, which can be substituted with the same substituents with optionally substituted $C_1$-$C_4$ alkyl or $C_1$-$C_4$ alkoxy, and each of $R^3$, $R^4$, and $R^5$ independently represent H, halo, or an optionally substituted $C_1$-$C_4$ alkyl or optionally substituted $C_1$-$C_4$ alkoxy group. In certain embodiments, $R^3$ and $R^5$ each represent H.

In these compounds, $R^4$ is typically an optionally substituted $C_1$-$C_4$ alkyl, and in some embodiments, $R^4$ is $C_1$-$C_4$ alkyl substituted with an optionally substituted phenyl ring or heteroaryl ring (e.g., pyridine, pyrimidine, indole, thiophene, furan, oxazole, isoxazole, benzoxazole, benzimidazole, and the like). In some of these embodiments, $R^5$ is H. The optionally substituted phenyl or hereoaryl ring can have up to three substituents selected from Me, CN, $CF_3$, halo, OMe, $NH_2$, NHMe, $NMe_2$, and optionally substituted $C_1$-$C_4$ alkyl or $C_1$-$C_4$ alkoxy, wherein substituents for the optionally substituted $C_1$-$C_4$ alkyl or $C_1$-$C_4$ alkoxy groups in Formula (I) are selected from halo, —OH, —OMe, $C_1$-$C_4$ alkyl, $C_1$-$C_4$ alkoxy, COOH, —$PO_3H_2$, —$OPO_3H_2$, $NH_2$, $NMe_2$, $C_3$-$C_6$ cycloalkyl, aryl (preferably phenyl or substituted phenyl), $C_5$-$C_6$ heterocyclyl (e.g. piperidine, morpholine, thiomorpholine, pyrrolidine); and the pharmaceutically acceptable salts of these compounds.

Other examples of benzonaphthyridine compounds suitable for use as adjuvants include compounds of the following formula:

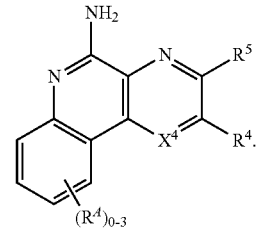

where each $R^A$ is independently halo, CN, $NH_2$, NHMe, $NMe_2$, or optionally substituted $C_1$-$C_4$ alkyl or optionally substituted $C_1$-$C_4$ alkoxy; $X^4$ is CH or N;

and $R^4$ and $R^5$ independently represent H or an optionally substituted alkyl or optionally substituted alkoxy group.

Preferably compounds of the above formula have 0-1 $R^A$ substituents present.

In these compounds, $R^4$ is typically an optionally substituted $C_1$-$C_4$ alkyl, and in some embodiments, $R^4$ is $C_1$-$C_4$ alkyl substituted with an optionally substituted phenyl ring or heteroaryl ring (e.g., pyridine, pyrimidine, indole, thiophene, furan, oxazole, isoxazole, benzoxazole, benzimidazole, and the like). In some of these embodiments, $R^5$ is H. The optionally substituted phenyl or hereoaryl ring can have up to three substituents selected from Me, CN, $CF_3$, halo, OMe, $NH_2$, NHMe, $NMe_2$, and optionally substituted $C_1$-$C_4$ alkyl or $C_1$-$C_4$ alkoxy, wherein substituents for the optionally substituted $C_1$-$C_4$ alkyl or $C_1$-$C_4$ alkoxy groups in Formula (X) are selected from halo, —OH, —OMe, $C_1$-$C_4$ alkyl, $C_1$-$C_4$ alkoxy, COOH, —$PO_3H_2$, —$OPO_3H_2$, $NH_2$, $NMe_2$, $C_3$-$C_6$ cycloalkyl, aryl (preferably phenyl or substituted phenyl), $C_5$-$C_6$ heterocyclyl (e.g. piperidine, morpholine, thiomorpholine, pyrrolidine); and the pharmaceutically acceptable salts of these compounds.

In certain embodiments, the benzonaphthyridine compound is selected from: 2-(4-(2-(5-amino-8-methylbenzo[f][1,7]naphthyridin-2-yl)ethyl)-3-methylphenyl)propan-2-ol; 2-(4-methoxy-2-methylphenethyl)-8-methylbenzo[f][1,7]naphthyridin-5-amine; 2-(2,4-dimethylphenethyl)benzo[f][1,7]naphthyridin-5-amine; ethyl 4-(2-(5-amino-8-methylbenzo[f][1,7]naphthyridin-2-yl)ethyl)-3-methylbenzoate; 2-(4-(dimethylamino)phenethyl)-8-methylbenzo[f][1,7]naphthyridin-5-amine, and 2-(4-methoxyphenethyl)-8-methylbenzo[f][1,7]naphthyridin-5-amine.

Other examples of benzonaphthyridine compounds suitable for use as adjuvants, as well as methods of formulating and manufacturing, include those described in International Application No. PCT/US2009/35563 (published as WO2009/111337).

U. Other Adjuvants

Other substances that act as immunological adjuvants are disclosed in Burdman, J. R. et al. (eds) (1995) (*Vaccine Design: Subunit and AdjuvantApproach* (Springer) (Chapter 7) and O'Hagan, D. T. (2000) (*Vaccine Adjuvants: Preparation Methods and Research Protocols* (Humana Press) (Volume 42 of *Methods in Molecular Medicine* series)).

Further useful adjuvant substances include:

Methyl inosine 5'-monophosphate ("MIMP") (Signorelli & Hadden (2003) *Int. Immunopharmacol.* 3(8): 1177-1186).

A polyhydroxlated pyrrolizidine compound (WO2004/064715), such as one having formula:

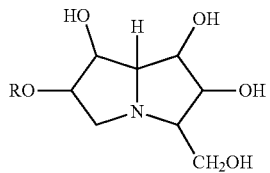

where R is selected from the group comprising hydrogen, straight or branched, unsubstituted or substituted, saturated or unsaturated acyl, alkyl (e.g. cycloalkyl), alkenyl, alkynyl and aryl groups, or a pharmaceutically acceptable salt or derivative thereof. Examples include, but are not limited to: casuarine, casuarine-6-α-D-glucopyranose, 3-pi-casuarine, 7-epi-casuarine, 3,7-diepi-casuarine, etc.

A gammainulin (Cooper (1995) *Pharm. Biotechnol.* 6:559-580) or derivative thereof, such as algammulin. Compounds disclosed in PCT/US2005/022769.

Compounds disclosed in WO2004/87153, including: Acylpiperazine compounds, Indoledi one compounds, Tetrahydrais oquinoline (THIQ) compounds, Benz ocyclodi one compounds, Aminoazavinyl compounds, Aminobenzimidazole quinolinone (ABIQ) compounds (U.S. Pat. No. 6,605,617; WO 02/18383), Hydrapthalamide compounds, Benzophenone compounds, Isoxazole compounds, Sterol compounds, Quinazilinone compounds, Pyrrole compounds (WO2004/018455), Anthraquinone compounds, Quinoxaline compounds, Triazine compounds, Pyrazalopyrimidine compounds, and Benzazole compounds (WO03/082272).

Loxoribine (7-allyl-8-oxoguanosine) (U.S. Pat. No. 5,011,828).

A formulation of a cationic lipid and a (usually neutral) co-lipid, such as aminopropyl-dimethyl-myristoleyloxy-propanaminium bromide-diphytanoylphosphatidyl-ethanol amine (VAXFECTIN™) or aminopropyl-dimethyl-bis-dodecyl oxy-propanaminium bromide-dioleoylphosphatidyl-ethanolamine ("GAP-DLRIE: DOPE"). Formulations containing (±)-N-(3-aminopropyl)-N,N-dimethyl-2,3-bis(syn-9-tetradeceneyloxy)-1-propanaminium salts are preferred (U.S. Pat. No. 6,586,409)

The invention may also comprise combinations of aspects of one or more of the immunological adjuvants identified above. For example, the following adjuvant compositions may be used in the invention: (1) a saponin and an oil-in-water emulsion (WO 99/11241); (2) a saponin (e.g., QS21)+a non-toxic LPS derivative (e.g. 3dMPL) (see WO 94/00153); (3) a saponin (e.g., QS21)+a non-toxic LPS derivative (e.g. 3dMPL)+a cholesterol; (4) a saponin (e.g., QS21)+3dMPL+IL-12 (optionally+a sterol) (WO 98/57659); (5) combinations of 3dMPL with, for example, QS21 and/or oil-in-water emulsions (see EP 0 835 318; EP 0 735 898; and EP 0 761 231); (6) SAF, containing 10% Squalane, 0.4% TWEEN 80 (polyoxyethylene sorbitan monooleate), 5% pluronic-block polymer L121, and thr-MDP, either microfluidized into a submicron emulsion or vortexed to generate a larger particle size emulsion; (7) RIBI adjuvant system (RAS), (Ribi Immunochem, Hamilton, Mont.) containing 2% Squalene, 0.2% TWEEN 80 (polyoxyethylene sorbitan monooleate), and one or more bacterial cell wall components from the group consisting of monophosphorylipid A (MPL), trehalose dimycolate (TDM), and cell wall skeleton (CWS), preferably MPL+CWS (DETOX); (8) one or more mineral salts (such as an aluminum salt)+a non-toxic derivative of LPS (such as 3dPML); (9) one or more mineral salts (such as an aluminum salt)+an immunostimulatory oligonucleotide (such as a nucleotide sequence including a CpG motif).

Aluminum salts and MF59 adjuvant are preferred adjuvants for use with injectable influenza vaccines. Bacterial toxins and bioadhesives are preferred adjuvants for use with mucosally-delivered vaccines, such as nasal vaccines.

4. Therapeutic Agents

Therapeutic agents suitable for use in the invention include small molecule drugs and biologics.

Such therapeutic agents include therapeutic agents used in the treatment of respiratory diseases and/or disorders including, but not limited to, asthma, bronchial asthma, allergic asthma, intrinsic asthma, extrinsic asthma, exercise-induced asthma, drug-induced asthma (including aspirin and NSAID-induced) and dust-induced asthma, chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavinrus (including SARS) and adenovirus.

Such therapeutic agents include therapeutic agents used in the treatment of dermatological disorders including, but not limited to, psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, basal cell carcinoma, actinic keratosis, discoid lupus erythematosus, pemphigus, pemphigoid, epidermolysis bullosa, urticaria, angioedema, vasculitides, toxic erythemas, cutaneous eosinophilias, alopecia areata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions.

Such therapeutic agents include therapeutic agents used in the treatment of ocular diseases and/or disorders including, but not limited to, blepharitis; conjunctivitis, including perennial and vernal allergic conjunctivitis; iritis; anterior and posterior uveitis; choroiditis; autoimmune, degenerative or inflammatory disorders affecting the retina; ophthalmitis including sympathetic ophthalmitis; sarcoidosis; infections including viral, fungal, and bacterial.

Such therapeutic agents include therapeutic agents used in the treatment of genitourinary diseases and/or disorders including, but not limited to, nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female).

Such therapeutic agents include therapeutic agents used in the treatment of allograft rejection including, but not limited to, acute and chronic following, for example, transplantation of kidney, heart, liver, lung, bone marrow, skin or cornea or following blood transfusion; or chronic graft versus host disease.

Such therapeutic agents include therapeutic agents used in the treatment of other auto-immune and allergic disorders including, but not limited to, rheumatoid arthritis, irritable bowel syndrome, systemic lupus erythematosus, multiple sclerosis, Hashimoto's thyroiditis, Crohns disease, inflammatory bowel disease (IBD), Graves' disease, Addison's disease, diabetes mellitus, idiopathic thrombocytopaenic purpura, eosinophilic fasciitis, hyper-IgE syndrome, antiphospholipid syndrome and Sazary syndrome.

Such therapeutic agents include therapeutic agents used in the treatment of cancer including, but not limited to, prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumor recurrences, and paraneoplastic syndromes. In certain embodiments, the compounds of Formula (I), pharmaceutically acceptable salts, solvates, N-oxides, prodrugs and isomers thereof, and pharmaceutical compositions provided herein are useful as modulators of toll-like receptor activity, and are used in the treatment of neoplasias including, but not limited to, basal cell carcinoma, squamous cell carcinoma, actinic keratosis, melanoma, carcinomas, sarcomas, leukemias, renal cell carcinoma, Kaposi's sarcoma, myelogeous leukemia, chronic lymphocytic leukemia and multiple myeloma.

Such therapeutic agents include therapeutic agents used in the treatment of infectious diseases including, but not limited to, viral diseases such as genital warts, common warts, plantar warts, respiratory syncytial virus (RSV), hepatitis B, hepatitis C, Dengue virus, herpes simplex virus (by way of example only, HSV-I, HSV-II, CMV, or VZV), molluscum contagiosum, vaccinia, variola, lentivirus, human immunodeficiency virus (HIV), human papilloma virus (HPV), cytomegalovirus (CMV), varicella zoster virus (VZV), rhinovirus, enterovirus, adenovirus, coronavirus (e.g., SARS), influenza, para-influenza, mumps virus, measles virus, papovavirus, hepadnavirus, flavivirus, retrovirus, arenavirus (by way of example only, LCM, Junin virus, Machupo virus, Guanarito virus and Lassa Fever) and filovirus (by way of example only, ebola virus or marbug virus).

Such therapeutic agents include therapeutic agents used in the treatment of bacterial, fungal, and protozoal infections including, but not limited to, tuberculosis and *Mycobacterium avium*, leprosy; *Pneumocystis carnii*, cryptosporidiosis, histoplasmosis, toxoplasmosis, trypanosome infection, leishmaniasis, infections caused by bacteria of the genus *Escherichia, Enterobacter, Salmonella, Staphylococcus, Klebsiella, Proteus, Pseudomonas, Streptococcus,* and *Chlamydia*, and fungal infections such as candidiasis, aspergillosis, histoplasmosis, cryptococcal meningitis.

5. Cryoprotective Agents

As previously noted, cryoprotective agents can be added to the microparticle compositions of the present invention in some embodiments, for example, to prevent substantial microparticle agglomeration from occurring when lyophilized compositions in accordance with the invention are resuspended.

Cryoprotective agents include (a) amino acids such as glutamic acid and arginine, among others; (b) polyols, including diols such as ethylene glycol, propanediols such as 1,2-propylene glycol and 1,3-propylene glycol, and butane diols such as 2,3-butylene glycol, among others, triols such as glycerol, among others, as well as other higher polyols; and (c) carbohydrates including, for example, (i) monosaccharides (e.g., glucose, galactose, and fructose, among others), (ii) polysaccharides including disaccharides (e.g., sucrose, lactose, trehalose, maltose, gentiobiose and cellobiose, among others), trisaccharides (e.g., raffinose, among others), tetrasaccharides (e.g., stachyose among others), pentasaccharides (e.g., verbascose among others), as well as numerous other higher polysaccharides, and (iii) alditols such as xylitol, sorbitol, and mannitol, among others (in this regard, is noted that alditols are higher polyols, as well as being carbohydrates).

Compositions in accordance with the invention can contain varying amounts of cryoprotective agent, where provided, depending on the amount that is effective to prevent substantial microparticle agglomeration from occurring when the lyophilized compositions of the invention are resuspended.

6. Charged Species

As noted above, microparticle compositions in accordance with the present invention may include charged species in order to impart a surface charge to the microparticles. Examples of charged species include, for example, charged surfactants, charged polymers and charged small molecules. Such species may be provided, for example, in an amount effective to promote adsorption of species to the surfaces of the microparticles (e.g., antigens, immunological adjuvants, etc.). Such species may also be provided, for example, in an amount effective to promote acceptable microparticle suspension (e.g., during microparticle formation and/or resuspension after lyophilization).

Specific examples of charged small molecules include biotin and charged small molecule immune potentiators.

Charged surfactants include cationic and anionic surfactants. Cationic surfactants include, for example, cetyltrimethylammonium bromide or "CTAB" (e.g., cetrimide), benzalkonium chloride, DDA (dimethyl dioctodecyl ammonium bromide), and DOTAP (dioleoyl-3-trimethylammonium-propane), among others. Anionic surfactants include, for example, SDS (sodium dodecyl sulfate), SLS (sodium lauryl sulfate), DSS (disulfosuccinate), and sulphated fatty alcohols, among others.

Charged polymers are polymers having multiple charged groups. (Such polymers are also commonly referred to as "polyelectrolytes.") Some charged polymers have only anionic groups at physiological pH and thus have a negative net charge (referred to herein as polyanions). Other charged polymers have only cationic groups at physiological pH and thus have a positive net charge at physiological pH (referred to herein as polycations). Still other charged polymers have both anionic and cationic groups (e.g., peptides, proteins, etc.) and may have a negative net charge (e.g., because the anionic groups contribute more charge than the cationic groups) or a positive net charge (e.g., because the cationic groups contribute more charge than the anionic groups). Depending on which groups predominate at physiological pH, charged polymers containing both cationic and anionic groups may be categorized herein as either polycations (where the polymer has a positive net charge) or polyanions (where the polymer has a negative net charge).

Specific examples of polycations include, for instance, polyamines, including poly(amino methacrylates) including poly(dialkylaminoalkyl methacrylates) such as poly(dimethylaminoethyl methacrylate) and poly(diethylaminoethyl methacrylate), polyvinylamines, polyvinylpyridines including quaternary polyvinylpyridines such as poly(N-ethyl-4-vinylpyridine), poly(vinylbenzyltrimethylamines), polyallylamines such as poly(allylamine hydrochloride) (PAH) and poly(diallyldialklylamines) such as poly(diallyldimethylammonium chloride), polyamidoamines, polyimines including polyalkyleneimines such as poly(ethylene imine) (PEI), poly(propylene imine) and ethoxylated poly(ethylene imines), polycationic peptides and proteins, including histone peptides and homopolymer and copolymers containing basic amino acids such as lysine, arginine, ornithine and combinations thereof, gelatin, protamine and protamine sulfate, spermine, spermidine, hexadimethrene bromide (polybrene), and polycationic polysaccharides such as cationic starch and chitosan, as well as copolymers, salts, derivatives and combinations of the preceding, among various others.

Specific examples of polyanions include, for instance, polysulfonates such as polyvinylsulfonates, poly(styrenesulfonates) such as poly(sodium styrenesulfonate) (PSS), sulfonated poly(tetrafluoroethylene), polysulfates such as polyvinylsulfates, sulfated and non-sulfated glycosaminoglycans as well as certain proteoglycans, for example, heparin, heparin sulfate, chondroitin sulfate, keratan sulfate, dermatan sulfate, polycarboxylates such as acrylic acid polymers and salts thereof (e.g., ammonium, potassium, sodium, etc.), for instance, those available from Atofina and Polysciences Inc., methacrylic acid polymers and salts thereof (e.g., EUDRAGIT, a methacrylic acid and ethyl acrylate copolymer), carboxymethylcellulose, carboxymethylamylose and carboxylic acid derivatives of various other polymers, polyanionic peptides and proteins such as homopolymers and copolymers of acidic amino acids such as glutamic acid, aspartic acid or combinations thereof, homopolymers and copolymers of uronic acids such as mannuronic acid, galaturonic acid and guluronic acid, and their salts, alginic acid and its salts, hyaluronic acid and its salts, albumin, gelatin, carrageenan, polyphosphates such as phosphoric acid derivatives of various polymers, polyphosphonates such as polyvinylphosphonates, as well as copolymers, salts, derivatives, and combinations of the preceding, among various others.

7. Further Excipients

One or more additional pharmaceutically acceptable excipients such as biological buffering substances, tonicity adjusting agents, and the like, may also be present in the microparticle compositions of the present invention.

8. Administration

Once formulated (and resuspended as necessary), the microparticle compositions of the invention can be administered parenterally, e.g., by injection (which may be needleless), among other routes of administration. In this regard, the microparticle compositions are typically supplied lyophilized in a vial or other container which is supplied with a septum or other suitable means for supplying a resuspension medium (e.g., Water for Injection) and for withdrawing the resultant suspension. A suitable syringe may also be supplied for injection.

As noted above, in certain embodiments, the microparticle compositions are gamma irradiated in which case it may be desirable to add antigen(s) and any other radiation sensitive species (e.g., immunological adjuvants, etc.) at the time of administration.

For example, a solution or suspension containing one or more antigens and/or one or more immunological adjuvants may be introduced to a lyophilized microparticle composition within a vial and the vial agitated (e.g., swirled) to thoroughly mix the contents. The contents are then withdrawn for administration to a vertebrate subject.

In some embodiments, a predetermined period of time is allowed to pass after contact between the antigen(s) and/or immunological adjuvant(s), before the composition is administered. For example, the composition may be administered after time ranging from 30 minutes to 10 minutes to 5 minutes to 1 minute to immediately after such contact.

The compositions can be injected subcutaneously, intradermally, intramuscularly, intravenously, intraarterially, or intraperitoneally, for example. Other modes of administration include nasal, mucosal, intraoccular, rectal, vaginal, oral and pulmonary administration, and transdermal or transcutaneous applications.

In some embodiments, the compositions of the present invention can be used for site-specific targeted delivery. For example, intravenous administration of the compositions can be used for targeting the lung, liver, spleen, blood circulation, or bone marrow.

Treatment may be conducted according to a single dose schedule or a multiple dose schedule. A multiple dose schedule is one in which a primary course of administration may be given, for example, with 1-10 separate doses, followed by other doses given at subsequent time intervals, chosen to maintain and/or reinforce the therapeutic response, for example at 1-4 months for a second dose, and if needed, a subsequent dose(s) after several months. The dosage regimen will also be, at least in part, determined by the need of the subject and be dependent on the judgment of the practitioner.

Furthermore, if prevention of disease is desired, the compositions are generally administered prior to the arrival of the primary occurrence of the infection or disorder of interest. If other forms of treatment are desired, e.g., the reduction or elimination of symptoms or recurrences, the compositions are generally administered subsequent to the arrival of the primary occurrence of the infection or disorder of interest.

9. Kits

This invention encompasses kits which can simplify the administration of appropriate amounts of immunological compositions to a subject.

A typical kit of the invention comprises a unit dosage form of a lyophilized microparticle composition in accordance with the invention, preferably in a sealed container.

Kits of the invention can further comprise a sealed container which contains one or more antigens and/or one or more immunological adjuvants. The antigens and/or adjuvants may be in lyophilized form or provided in the form of an aqueous fluid.

Kits of the invention can further comprise a sealed container which contains one or more therapeutic agents and/or charged drugs. The therapeutic agents and/or charged drugs may be in lyophilized form or provided in the form of an aqueous fluid.

Kits of the invention can further comprise a sealed container which contains a pharmaceutically acceptable vehicle that can be used to suspend and administer the lyophilized microparticle composition and in some embodiments to suspend/dissolve any lyophilized antigen and/or adjuvant composition that is supplied, and in other embodiments to suspend/dissolve any lyophilized therapeutic agent and/or charged drug composition.

The kit may further include one or more devices that can be used to administer the compositions of the invention to a vertebrate subject. Examples of such devices include, but are not limited to, syringes, drip bags, and inhalers.

For instance, a syringe may be used to introduce a suitable pharmaceutically acceptable vehicle (e.g., Water for Injection) to a lyophilized composition containing one or more antigens (and optionally one or more adjuvants) in a sealed container. The resulting antigen-containing suspension/solution may then be withdrawn from the container and introduced to a microparticle composition in an additional container. The resulting suspension may then be withdrawn from the additional container and administered to a subject.

As noted above, in certain embodiments, a suitable period (e.g., to allow for sufficient antigen adsorption to the microparticles) is allowed to elapse between (a) the time where the antigen-containing suspension/solution is introduced to the microparticle composition and (b) the time of introduction to a vertebrate subject.

10. Definitions

In describing the present invention, the following terms will be employed, and are intended to be defined as indicated below.

The term "microparticle" as used herein, refers to a particle of less than 10,000 nm in diameter, for example, from about 10 nm or less to about 150 µm in diameter, more particularly, ranging from 10 nm to 25 nm to 50 nm to 100 nm to 250 nm to 500 nm to 1000 nm to 2500 nm to 5000 nm to 10,000 nm. In some embodiments, dry microparticles exist in aggregates that are greater than 10,000 nm in diameter, but which disperse into microparticle sizes less than 10,000 nm upon addition of an aqueous fluid. The microparticles within the compositions of the present invention typically have a size distribution in aqueous fluid, wherein the Z average and/or the D(v,0.5) value is less than 5,000 nm, for example, ranging from 5,000 nm to 2,500 nm to 1,000 nm to 500 nm to 250 nm or less.

Particle size can be determined (measured) using methods available in the art. For example, particle size can be determined using photon correlation spectroscopy, dynamic light scattering or quasi-elastic light scattering. These methods are based on the correlation of particle size with diffusion properties of particles obtained from Brownian motion measurements. Brownian motion is the random movement of the particles due to bombardment by the solvent molecules that surround the particles. The larger the particle, the more slowly the Brownian motion will be. Velocity is defined by the translational diffusion coefficient (D). The value measured refers to how a particle moves within a liquid (hydrodynamic diameter). The diameter that is obtained is the diameter of a sphere that has the same translational diffusion coefficient as the particle.

Particle size can also be determined using static light scattering, which measures the intensity of light scattered by particles in a solution at a single time. Static light scattering measures light intensity as a function of scattering angle and solute concentration. Particles passing though a light source, for example, a laser beam, scatter light at an angle that is inversely proportional to their size. Large particles generate a diffraction pattern at low scattering angles with high intensity, whereas small particles give rise to wide angle low intensity signals. Particle size distributions can be calculated if the intensity of light scattered from a sample are measured as a function of angle. The angular information is compared with a scattering model (e.g., Mie theory) in order to calculate the size distribution.

Generally, particle size is determined at room temperature and involves multiple analyses of the sample in question (e.g., at least 3 repeat measurements on the same sample) to yield an average value for the particle diameter.

For photon correlation spectroscopy, Z average (also called the cumulant mean or hydrodynamic diameter) is typically calculated from cumulants (monomodal) analysis.

For static light scattering measurements (and also for photon correlation spectroscopy in some embodiments), volume-based size parameters may be measured. For instance, the D(v,0.5) (where v means volume) is a size parameter whose value is defined as the point where 50% of the particles (volume basis) in the composition, as measured, have a size that is less than the D(v,0.5) value, and 50% of the particles in the composition have a size that is greater than the D(v,0.5) value.

As defined herein, a "suspension" is a liquid phase that contains suspended solid particulate material. Suspensions can be stable or unstable. As defined herein, a "solution" is a liquid phase that contains dissolved material. As defined herein, an "aqueous" suspension or solution is a suspension or solution that contains water, typically 50 wt % water or more, for example, ranging from 50 wt % to 75 wt % to 90 wt % to 95 wt % or more water.

As defined herein, "dry" microparticle compositions are microparticle compositions that are not immersed in a liquid (e.g., not within a liquid suspension). Typically, a "dry" microparticle composition will comprise less than 3% water.

As defined herein, "blank" microparticle compositions are microparticle compositions that are free of active agents (i.e., they are free of pharmaceuticals, including drugs, immunological adjuvants, antigens, etc.).

Microparticle compositions for use herein are typically formed from polymers that are sterilizable, substantially non-toxic and biodegradable. Such materials include polyesters (e.g., poly[hydroxy acids] such as polylactide and polyglcolide, poly[cyclic esters] such as caprolactone, etc.), polycarbonates, polyorthoesters, polyanhydrides, polycyanoacrylates, polyphosphazines, and combinations thereof, among others. More typically, microparticles for use with the present invention are polymer microparticles derived from poly($\alpha$-hydroxy acids), for example, from a poly (lactide) ("PLA") such as poly(L-lactide) or poly(D,L-lactide), from a copolymer of lactide and glycolide ("PLGA") such as a poly(L-lactide-co-glycolide) or poly(D,L-lactide-co-glycolide), or from a copolymer of lactide and caprolactone. The polymer microparticles may thus be formed using any of various polymeric starting materials which have a variety of molecular weights and, in the case of the copolymers, such as PLGA, a variety of monomer (e.g., lactide: glycolide) ratios, the selection of which will be largely a matter of choice, depending in part on the coadministered species. These parameters are discussed further below.

"Zeta potential," as used herein, refers to the electrical potential that exists across the interface of all solids and liquids, e.g., the potential across the diffuse layer of ions surrounding a charged colloidal particle. Zeta potential can be calculated from electrophoretic mobilities, i.e., the rates at which colloidal particles travel between charged electrodes placed in contact with the substance to be measured, using techniques well known in the art.

The term "surfactant" comes from the phrase "surface active agent". Surfactants accumulate at interfaces (e.g., at liquid-liquid, liquid-solid and/or liquid-gas interfaces) and change the properties of that interface. As used herein, surfactants include detergents, dispersing agents, suspending agents, emulsion stabilizers, and the like.

As defined herein, "carbohydrates" include monosaccharides, oligosaccharides and polysaccharides, as well as substances derived from monosaccharides, for example, by reduction (e.g., alditols), by oxidation of one or more terminal groups to carboxylic acids (e.g., glucuronic acid), or by replacement of one or more hydroxy group(s) by a hydrogen atom or an amino group (e.g., beta-D-glucosamine and beta-D-galactosamine).

As defined herein, a "monosaccharide" is a polyhydric alcohol, i.e., an alcohol that further comprises either an aldehyde group (in which case the monosaccharide is an aldose) or a keto group (in which case the monosaccharide is a ketose). Monosaccharides typically contain from 3-10 carbons. Moreover, monosaccharides commonly have the empirical formula $(CH_2O)_n$, where n is an integer of three or greater, typically 3-10. Examples of 3-6 carbon aldoses include glyceraldehyde, erythrose, threose, ribose, 2-deoxyribose, arabinose, xylose, lyxose, allose, altrose, glucose, mannose, gulose, idose, galactose, and talose. Examples of 3-6 carbon ketoses include dihydroxyacetone, erythrulose, ribulose, xylulose, psicose, fructose, sorbose, and tagatose. Naturally occurring monosaccharides are normally found in the D-isomer form, as opposed to the L-form.

An "oligosaccharide" refers to a relatively short monosaccharide polymer, i.e., one containing from 2 to 30 monosaccharide units. A "polysaccharide" is a monosaccharide polymer that is beyond oligosaccharide length (i.e., one containing more than 30 monosaccharide units). Moreover, as used herein, the term "polysaccharide" also refers to a monosaccharide polymer that contains two or more linked monosaccharides. To avoid ambiguity, the second definition is to be applied at all times, unless there are explicit indications to the contrary. The term "polysaccharide" also includes polysaccharide derivatives, such as amino-functionalized and carboxyl-functionalized polysaccharide derivatives, among many others. Monosaccharides are typically linked by glycosidic linkages. Specific examples include disaccharides (such as sucrose, lactose, trehalose, maltose, gentiobiose and cellobiose), trisaccharides (such as raffinose), tetrasaccharides (such as stachyose), and pentasaccharides (such as verbascose).

As used herein the term "saccharide" encompasses monosaccharides, oligosaccharides and polysaccharides. A "saccharide-containing species" is a molecule, at least a portion of which is a saccharide. Examples include saccharide cryoprotective agents, saccharide antigens, antigens comprising saccharides conjugated to carrier peptides, and so forth. A "polysaccharide-containing species" is a molecule, at least a portion of which is a polysaccharide.

As used herein, a "cryoprotective agent" is an agent that protects a composition from experiencing adverse effects upon freezing and thawing. For example, in the present invention, cryoprotective agents may be added to prevent substantial microparticle agglomeration from occurring when the lyophilized compositions of the invention are resuspended.

As used herein, the term "polynucleotide" means a homopolymer or heteropolymer of at least 2 nucleotide units (also referred to herein as "nucleotides"). Nucleotides forming polynucleotides as defined herein include naturally occurring nucleotides, such as ribonucleotides and deoxyribonucleotides, as well as equivalents, derivatives, variants and analogs of naturally occurring nucleotides.

A polynucleotide may be in either single-stranded form or multi-stranded form (e.g., double-stranded, triple-stranded, etc.). A polynucleotide may be in linear form or non-linear form (e.g., comprising circular, branched, etc. elements). A polynucleotide may be natural, synthetic or a combination of both.

A polynucleotide may be capable of self-replication when introduced into a host cell. Examples of polynucleotides thus include self-replicating RNAs and DNAs and, for instance, selected from replicons, plasmids, cosmids, phagemids, transposons, viral vectors, artifical chromosomes (e.g., bacterial, yeast, etc.) as well as other self-replicating species.

Polynucleotides include those that express antigenic polypeptides in a host cell (e.g., polynucleotide-containing antigens). Polynucleotides include self-replicating polynucleotides within which natural or synthetic sequences derived from eucaryotic or prokaryotic organisms (e.g, genomic DNA sequences, genomic RNA sequences, cDNA sequences, etc.) have been inserted. Specific examples of self-replicating polynucleotides include RNA vector constructs and DNA vector constructs, among others. Sequences that may be expressed include native sequences and modifications, such as deletions, additions and substitutions (generally conservative in nature), to native sequences, among others. These modifications may be deliberate, as through site-directed mutagenesis, or may be accidental, such as through mutations of hosts that produce antigens.

As define herein an "oligonucleotide" is a polynucleotide having in the range of 5 to 100 and more preferably 5 to 30 nucleotides in size.

As used herein, the phrase "nucleic acid" includes DNA, RNA, and chimeras formed therefrom.

A "polynucleotide-containing species" is a molecule, at least a portion of which is a polynucleotide.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include modifications, such as deletions, additions and substitutions (generally conservative in nature), to a native sequence, for example, such that the protein maintains the ability to elicit an immunological response or have a therapeutic effect on a subject to which the protein is administered.

A "polypeptide-containing species" is a molecule, at least a portion of which is a polypeptide. Examples include polypeptides, proteins including glycoproteins, saccharide antigens conjugated to carrier proteins, and so forth.

The term "pharmaceutical" refers to biologically active compounds such as drugs, antibiotics, antiviral agents, growth factors, hormones, antigens, adjuvants and the like.

The term "adjuvant" refers to any substance that assists or modifies the action of a pharmaceutical, including but not limited to immunological adjuvants, which increase or diversify the immune response to an antigen. Hence, immunological adjuvants are compounds that are capable of potentiating an immune response to antigens. Immunological adjuvants can potentiate humoral and/or cellular immunity.

By "antigen" is meant a molecule that contains one or more epitopes capable of stimulating a host's immune system to make a cellular antigen-specific immune response when the antigen is presented, or a humoral antibody response. An antigen may be capable of eliciting a cellular and/or humoral response by itself or when present in combination with another molecule.

An "epitope" is that portion of an antigenic molecule or antigenic complex that determines its immunological specificity. An epitope is within the scope of the present definition of antigen.

Commonly, an epitope is a polypeptide or polysaccharide in a naturally occurring antigen. In artificial antigens it can be a low molecular weight substance such as an arsanilic acid derivative. An epitope will react specifically in vivo or in vitro with, for example, homologous antibodies or T lymphocytes. Alternative descriptors are antigenic determinant, antigenic structural grouping and haptenic grouping.

Frequently, an epitope will include between about 5 to 15 amino acids. Epitopes of a given protein can be identified using any number of epitope mapping techniques, well known in the art. See, e.g., *Epitope Mapping Protocols in Methods in Molecular Biology*, Vol. 66 (Glenn E. Morris, Ed., 1996) Humana Press, Totowa, N.J. For example, linear epitopes may be determined by, for example, concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) (*Proc. Natl. Acad. Sci. USA* 81:3998-4002); Geysen et al. (1986) (*Molec. Immunol.* 23:709-715). Similarly, conformational epitopes are readily identified by determining spatial conformation of amino acids such as by, e.g., x-ray crystallography and two-dimensional nuclear magnetic resonance. See, e.g., *Epitope Mapping Protocols*, supra.

The term "antigen" as used herein denotes both subunit antigens, i.e., antigens which are separate and discrete from a whole organism with which the antigen is associated in nature, as well as killed, attenuated or inactivated bacteria, viruses, parasites or other pathogens or tumor cells. Antibodies such as anti-idiotype antibodies, or fragments thereof, and synthetic peptide mimotopes, which can mimic an antigen or antigenic determinant, are also captured under the definition of antigen as used herein.

Similarly, an oligonucleotide or polynucleotide that expresses an immunogenic protein, or antigenic determinant in vivo, such as in nucleic acid immunization applications, is also included in the definition of antigen herein.

Furthermore, for purposes of the present invention, an "antigen" refers to a protein having modifications, such as deletions, additions and substitutions (generally conservative in nature), to the native sequence, as long as the protein maintains the ability to elicit an immunological response. These modifications may be deliberate, as through site-directed mutagenesis, or may be accidental, such as through mutations of hosts which produce the antigens.

An "immunological response" or "immune response" to an antigen or composition is the development in a subject of a humoral and/or a cellular immune response to molecules present in the composition of interest.

Immune responses include innate and adaptive immune responses. Innate immune responses are fast-acting responses that provide a first line of defense for the immune system. In contrast, adaptive immunity uses selection and clonal expansion of immune cells having somatically rearranged receptor genes (e.g., T- and B-cell receptors) that recognize antigens from a given pathogen or disorder (e.g., a tumor), thereby providing specificity and immunological memory. Innate immune responses, among their many effects, lead to a rapid burst of inflammatory cytokines and activation of antigen-presenting cells (APCs) such as macrophages and dendritic cells. To distinguish pathogens from self-components, the innate immune system uses a variety of relatively invariable receptors that detect signatures from pathogens, known as pathogen-associated molecular patterns, or PAMPs. The addition of microbial components to experimental vaccines is known to lead to the development of robust and durable adaptive immune responses. The mechanism behind this potentiation of the immune responses has been reported to involve pattern-recognition receptors (PRRs), which are differentially expressed on a variety of immune cells, including neutrophils, macrophages, dendritic cells, natural killer cells, B cells and some nonimmune cells such as epithelial and endothelial cells. Engagement of PRRs leads to the activation of some of these cells and their secretion of cytokines and chemokines, as well as maturation and migration of other cells. In tandem, this creates an inflammatory environment that leads to the establishment of the adaptive immune response. PRRs include nonphagocytic receptors, such as Toll-like receptors (TLRs) and nucleotide-binding oligomerization domain (NOD) proteins, and receptors that induce phagocytosis, such as scavenger receptors, mannose receptors and 3-glucan receptors.

Reported TLRs (along with examples of some reported TLR agonists, which may be used as immunological adjuvants in various embodiments of the invention) include the following: TLR1 (bacterial lipoproteins from Mycobacteria, *Neisseria*), TLR2 (zymosan yeast particles, peptidoglycan, lipoproteins, glycolipids, lipopolysaccharide, lipopeptide), TLR3 (viral double-stranded RNA, poly:IC), TLR4 (bacterial lipopolysaccharides and analogues, plant product taxol), TLR5 (bacterial flagellins), TLR6 (yeast zymosan particles, lipotechoic acid, lipopeptides from *mycoplasma*), TLR7 (single-stranded RNA, imiquimod, resimiquimod, and other synthetic compounds such as loxoribine and bropirimine), TLR8 (single-stranded RNA, resimiquimod) and TLR9 (CpG oligonucleotides), among others. Dendritic cells are recognized as some of the most important cell types for initiating the priming of naive $CD4^+$ helper T (TH) cells and for inducing $CD8^+$ T cell differentiation into killer cells. TLR signaling has been reported to play an important role in determining the quality of these helper T cell responses, for instance, with the nature of the TLR signal determining the specific type of TH response that is observed (e.g., TH1 versus TH2 response). A combination of antibody (humoral) and cellular immunity are produced as part of a $T_H1$-type response, whereas a $T_H2$-type response is predominantly an antibody response. Various TLR ligands such as CpG DNA (TLR9) and imidazoquinolines (TLR7, TLR8) have been documented to stimulate cytokine production from immune cells in vitro. The imidazoquinolines are the first small, drug-like compounds shown to be TLR agonists. For further information, see, e.g., A. Pashine, N. M. Valiante and J. B. Ulmer (*Nature Medicine* 11, 563-68 (2005)), K. S. Rosenthal and D. H. Zimmerman (Clinical and Vaccine Immunology, 13(8), 821-829 (2006)), and the references cited therein.

For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTLs"). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

A composition such as an immunogenic composition or a vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

The ability of a particular antigen or composition to stimulate a cell-mediated immunological response may be determined by a number of assays known in the art, such as by lymphoproliferation (lymphocyte activation) assays, CTL cytotoxic cell assays, by assaying for T-lymphocytes specific for the antigen in a sensitized subject, or by measurement of cytokine production by T cells in response to restimulation with antigen. Such assays are well known in the art. See, e.g., Erickson et al. (1993) (*J. Immunol.* 151:4189-4199); Doe et al. (1994) (*Eur. J. Immunol.* 24:2369-2376); and the examples below.

Hence, an immunological response may include, for example, one or more of the following effects: the production of antibodies by B-cells; and/or the activation of suppressor T-cells and/or γδ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art, for instance, radioimmunoassays and ELISAs.

Immunogenic compositions of the present invention display "enhanced immunogenicity" when they possess a greater capacity to elicit an immune response than the immune response elicited by an equivalent amount of the antigen in a differing composition. Thus, a composition may display "enhanced immunogenicity," for example, because the composition generates a stronger immune response, or because a lower dose of antigen is necessary to achieve an immune response in the subject to which it is administered. Such enhanced immunogenicity can be determined, for example, by administering the compositions of the invention, and antigen controls, to animals and comparing assay results of the two.

As used herein, "treatment" (including variations thereof, for example, "treat" or "treated") refers to any of (i) the prevention of a pathogen or disorder in question (e.g. cancer or a pathogenic infection, as in a traditional vaccine), (ii) the reduction or elimination of symptoms, and (iii) the substantial or complete elimination of the pathogen or disorder in question. Treatment may be effected prophylactically (prior to arrival of the pathogen or disorder in question) or therapeutically (following arrival of the same).

The terms "effective amount" or "pharmaceutically effective amount" of an immunogenic composition of the present invention refer herein to a sufficient amount of the immunogenic composition to treat or diagnose a condition of interest. The exact amount required will vary from subject to subject, depending, for example, on the species, age, and general condition of the subject; the severity of the condition being treated; the particular antigen of interest; in the case of an immunological response, the capacity of the subject's immune system to synthesize antibodies, for example, and the degree of protection desired; and the mode of administration, among other factors. An appropriate "effective" amount in any individual case may be determined by one of ordinary skill in the art. Thus, a "therapeutically effective amount" will typically fall in a relatively broad range that can be determined through routine trials.

By "vertebrate subject" or "vertebrate animal" is meant any member of the subphylum cordata, including, without limitation, mammals such as cattle, sheep, pigs, goats, horses, and humans; domestic animals such as dogs and cats; and birds, including domestic, wild and game birds such as cocks and hens including chickens, turkeys and other gallinaceous birds. The term does not denote a particular age. Thus, both adult and newborn animals are covered.

By "pharmaceutically acceptable" or "pharmacologically acceptable" is meant a material which is not biologically or otherwise undesirable, i.e., the material may be administered to an individual without causing any excessively undesirable biological effects in the individual or interacting in an excessively deleterious manner with any of the components of the composition in which it is contained.

The term "excipient" refers to any essentially accessory substance that may be present in the finished dosage form. For example, the term "excipient" includes vehicles, binders, disintegrants, fillers (diluents), lubricants, glidants (flow enhancers), compression aids, colors, sweeteners, preservatives, suspending/dispersing agents, film formers/coatings, flavors and printing inks.

By "physiological pH" or a "pH in the physiological range" is meant a pH in the range of approximately 7.2 to 8.0 inclusive, more typically in the range of approximately 7.2 to 7.6 inclusive.

As used herein, the phrase "vector construct" generally refers to any assembly that is capable of directing the expression of a nucleic acid sequence(s) or gene(s) of interest. A vector construct typically includes transcriptional promoter/enhancer or locus defining element(s), or other elements which control gene expression by other means such as alternate splicing, nuclear RNA export, post-translational modification of messenger, or post-transcriptional modification of protein. In addition, the vector construct typically includes a sequence which, when transcribed, is operably linked to the sequence(s) or gene(s) of interest and acts as a translation initiation sequence. The vector construct may also optionally include a signal that directs polyadenylation, a selectable marker, as well as one or more restriction sites and a translation termination sequence. In addition, if the vector construct is placed into a retrovirus, the vector construct may include a packaging signal, long terminal repeats (LTRs), and positive and negative strand primer binding sites appropriate to the retrovirus used (if these are not already present).

A "DNA vector construct" refers to a DNA molecule that is capable of directing the expression of a nucleic acid sequence(s) or gene(s) of interest.

One specific type of DNA vector construct is a plasmid, which is a circular episomal DNA molecule capable of autonomous replication within a host cell. Typically, a plasmid is a circular double stranded DNA, loop into which additional DNA segments can be ligated. pCMV is one specific plasmid that is well known in the art. A preferred pCMV vector contains the immediate-early enhancer/promoter of CMV and a bovine growth hormone terminator. A specific example is described in detail in Chapman, B. S., et al. (1991) (*Nucleic Acids Res.* 19:3979-3986).

Other DNA vector constructs are known, which are based on RNA viruses. These DNA vector constructs typically comprise a promoter that functions in a eukaryotic cell, 5' of a cDNA sequence for which the transcription product is an RNA vector construct (e.g., an alphavirus RNA vector replicon), and a 3' termination region. The RNA vector construct preferably comprises an RNA genome from a picornavirus, togavirus, flavivirus, coronavirus, paramyxovirus, yellow fever virus, or alphavirus (e.g., Sindbis virus, Semliki Forest virus, Venezuelan equine encephalitis virus, or Ross River virus), which has been modified by the replacement of one or more structural protein genes with a selected heterologous nucleic acid sequence encoding a product of interest. The RNA vector constructs can be obtained by transcription in vitro from a DNA template. Specific examples include Sindbis-virus-based plasmids (pSIN) such as pSINCP, described, for example, in U.S. Pat. Nos. 5,814,482 and 6,015,686, as well as in International Publication Nos. WO 97/38087, WO 99/18226 and WO 02/26209. The construction of such vectors, in general, is described in U.S. Pat. Nos. 5,814,482 and 6,015,686.

Other examples of vector constructs include RNA vector constructs (e.g., alphavirus vector constructs) and the like. As used herein, "RNA vector construct", "RNA vector replicon" and "replicon" refer to an RNA molecule that is capable of directing its own amplification or self-replication in vivo, typically within a target cell. The RNA vector construct is used directly, without the requirement for introduction of DNA into a cell and transport to the nucleus where transcription would occur. By using the RNA vector for direct delivery into the cytoplasm of the host cell, autonomous replication and translation of the heterologous nucleic acid sequence occurs efficiently.

GENERAL

The practice of the present invention will employ, unless otherwise indicated, conventional methods of chemistry, biochemistry, molecular biology, immunology and pharmacology, within the skill of the art. Such techniques are explained fully in the literature. See, e.g., *Remington's Pharmaceutical Sciences*, 18th ed. (Easton, Pa.: Mack Publishing Company, 1990); *Methods In Enzymology* (S. Colowick and N. Kaplan, eds., Academic Press, Inc.); Weir, D. M., *Handbook of Experimental Immunology*, Vols. I-IV, 5th ed. (Blackwell Publishers, 1996); Sambrook, J. et al., *Molecular Cloning: A Laboratory Manual*, 3rd ed. (Cold Spring Harbor Laboratory Press, 2001); Ausubel, F. M. et al., *Short Protocols In Molecular Biology*, 5th ed. (*Current Protocols*, 2002); *Handbook of Surface and Colloidal Chemistry* (Birdi, K. S., ed, CRC Press, 2003) and *Seymour/Carraher's Polymer Chemistry*, 5th ed. (Marcel Dekker Inc., 2007).

Unless stated otherwise or unless the context clearly dictates otherwise, all percentages and ratios herein are given on a weight basis.

EXPERIMENTAL

Below are examples of specific embodiments for carrying out the present invention. The examples are offered for illustrative purposes only, and are not intended to limit the scope of the present invention in any way.

RG503 and RG505 poly(D,L-lactide-co-glycolide) 50:50 copolymer composition were obtained from Boehringer Ingelheim (Ingelheim, Germany). Dioctyl sodium sulfosuccinate (DSS) was from Sigma Chemical (St. Louis, Mo.). *Escherichia coli* (*E. coli*)-derived recombinant meningococcal B protein (Men B) antigens, 287-953, 936-741 and 961c (also known as GNA2132-1030, GNA2091-1870, and NadA, respectively, obtained from Novartis Vaccines (IRIS, Siena, Italy) were isolated and purified as described previously in WO02004/032958 and M. Pizza et al., *Science* 287: 1816-1820 (2000). Enzyme-linked immunosorbent assay (ELISA) microtiter plates were obtained from Nunc (Roskilde, Denmark).

All other reagents were procured from Sigma Chemical Company. All animal studies performed were approved by the Novartis Animal Use and Care Committee.

Further supporting experiments, including further details and optional variations, can be found in S. Jain. et al., *J. Pharm. Sci.* 100:646-654 (2010).

Example 1 Preparation of Microparticles

Microparticles were prepared by a solvent evaporation method as previously described (M. Singh et al., *J. Pharm. Sci.* 93: 273-282 (2004) and J. Kazzaz et al., *J. Control Release* 67: 347-356 (2000)). Microparticles were synthesized using W/O/W emulsion technique. 6 mL of phosphate-buffered saline was added to 30 mL of 6% w/v RG503 or RG505 poly(lactide-co-glycolide) polymer solution in dichloromethane, and homogenized for 2 min at 24,000 rpm using a 10-mm probe (Ultra-Turrax T25 IKA-Labortechnik, Wasserburg, Germany) to form W/O primary emulsion. This emulsion was added to 150 mL of water containing 0.05% w/w DSS, and homogenized at 16800 rpm for 15-20 min using a 20-mm probe (ES-15 Omni International, Jarrenton, Va.) for 20 min in an ice bath. The resulting emulsion was stirred at 1000 rpm overnight to evaporate dichloromethane. Microparticles were collected by filtration through a 53 µm filter and stored with stirring at 2-8° C.

The size distribution of the resulting microparticles was determined with a particle size analyzer (LA-920, Horiba). To pre-weighed glass vials, 1 mL of particle suspension was added and lyophilized (FreeZone 4.5 L Bench top freeze dry system Labconco). Polymer recovery was determined from the difference in the weights. PLG particle suspension (48 mg of PLG) was added to each glass vial (Metrohm) with 54 mg of mannitol and 18 mg of sucrose. These excipients were added to stabilize the formulation during lyophilization at 4.5% and 1.5% w/v of the final reconstitution volume, respectively. The particle suspensions were lyophilized for two days using a controlled cycle shelf lyophilizer (Virtis). Following lyophilization, the head space of the vial was purged with nitrogen to remove oxygen. (Oxygen content in the vials during gamma-irradiation can affect polymer degradation (T. N. Bowmer et al., *Journal of Applied Polymer Science* 24: 425-439 (1979)). The vials were sealed and certain of the vials were gamma-irradiated at 15 kGy or 25 kGy (H. Nguyen et al., *Cell Tissue Bank* 8: 93-105 (2007), H. Nguyen et al., *Cell Tissue Bank* 8: 81-91 (2007), H. Nguyen et al., *Cell Tissue Bank* 9: 139-147 (2008)). Vials were stored at 2-8° C. until used.

The lyophilized product was analyzed for the residual moisture content using Karl-Fischer Volumetric Titration system according to the manufacturer's instructions. Residual oxygen was determined by gas chromatography. The microparticles were reconstituted in sterile water and were tested for endotoxin content using EndoSafe PTS System (Charles River Laboratories, USA) according to the manufacturer's instructions.

Results of the above procedures (prior to irradiation) are presented in Table 1. PLG microparticles synthesized with RG503 or RG505 resulted in a homogeneous population with the particle size ~1 µm. A measure of the efficiency of the particle synthesis process is PLG recovery. For both RG503 and RG505 polymers, PLG recovery was determined to be >70%. The residual moisture content for the formulations was <3%. The endotoxin content was significantly less than the recommended limit of 1 EU/dose in 100 µL dose.

TABLE 1

MICROPARTICLE CHARACTERIZATION RESULTS POST-PARTICLE SYNTHESIS AND PRIOR TO GAMMA-IRRADIATION.

| | Median Particle Size (µm) | PLG Recovery (%) | Moisture Content (%) | Residual Oxygen Content (%) | Endotoxin Content (EU/dose) |
|---|---|---|---|---|---|
| RG503 PLG | 0.8 | 90 | 0.1 | 0.2 | 0.03 |
| RG505 PLG | 1.0 | 71 | 0.0 | <0.1 | 0.36 |

The non-irradiated and gamma-irradiated (25 kGy) RG503 microparticles were characterized for particle size and molecular weight to identify the effect of the irradiation process on the microparticles. Number average molecular weight (Mn) and weight average molecular weight (Mw) were measured for non-irradiated (non GI) and gamma-irradiated (GI) PLG particles by gel permeation chromatography.

As shown in Table 2 below, the mean particle size of the RG503 microparticles increased to 4.3 µm following gamma-irradiation. Similar increase in the mean particle size was observed for the RG505 microparticles post-irradiation (data not shown). This increase in particle size with gamma irradiation has been reported in literature (R. Dorati et al. *J Control Release* 107: 78-90 (2005); R. Dorati et al., *J. Microencapsul.* 23: 123-133 (2006); C. E. Holy et al., *Biomaterials* 22: 25-31 (2001)). RG503 polymer underwent degradation that was associated with 23% loss in molecular weight when gamma-irradiated at 25 kGy.

TABLE 2

RG503 PLG MICROPARTICLE CHARACTERIZATION RESULTS PRE- AND POST GAMMA-IRRADIATION.

| | Median Particle Size (µm) | Number Average Molecular Weight, Mn (Da) | Weight Average Molecular Weight, Mw (Da) | Mw/Mn |
|---|---|---|---|---|
| Pre-irradiation | 0.8 | 18800 | 34700 | 1.85 |
| Post-irradiation (25 kGy) | 4.3 | 14700 | 26800 | 1.82 |

Example 2 Preparation of Irradiated and Non-Irradiated Lyophilized Microparticle Compositions for Adsorption Efficiency Analysis and In Vivo Administration For each MenB antigen tested below, three groups of lyophilized microparticles were prepared.

Group I (overnight adsorption/lyophilization). Microparticles (RG503 or RG505) were prepared as described in Example 1. Three bacterial MenB antigens (287-953, 961c, 936-741) were independently adsorbed to the microparticles at 2-8° C. overnight. The protein-adsorbed microparticles were added to the vials in amounts corresponding to 4.8 and 48 mg that were sufficient to obtain a total antigen dose of 1 and 10 µg per antigen, respectively. 54 mg of D-Mannitol and 18 mg Sucrose were added to each vial and lyophilized using a Virtis shelf lyophilizer. The vials were reconstituted with water for injection prior to immunization to obtain 4 and 40 mg/mL of microparticle concentrations and a total antigen dose of 1 and 10 µg per antigen, respectively.

Group II (lyophilized/irradiated blank microparticles). Microparticles (RG503 or RG505) prepared as described in Example 1 were added at 48 mg per vial into a 5-mL vial along with 54 mg of D-Mannitol and 18 mg Sucrose, and were lyophilized in a Virtis shelf lyophilizer as described above. After lyophilization, the vials were treated with 15 or 25 kGy gamma-irradiation under nitrogen atmosphere and stored at 2-8° C.

Group III (lyophilized/non-irradiated blank microparticles). Microparticles (RG503 or RG505) prepared as described in Example 1 were added at 48 mg per vial into a 5-mL vial along with 54 mg of D-Mannitol and 18 mg Sucrose, and were lyophilized in a Virtis shelf lyophilizer as described above. After lyophilization, the vials were stored at 2-8° C.

Example 3. Adsorption Efficiency for Three Men B Strains

Three bacterial antigens of a trivalent MenB vaccine (287-953, 961c and 936-741) were independently added with water for injection to gamma-irradiated (Group II) and non-irradiated (Group III) microparticle compositions in vials prepared as described in Example 2, to obtain 4 and 40 mg/mL of microparticle concentrations and a total antigen dose per 100 µl of 1 and 10 µg per antigen, respectively. For 1 µg antigen dose, 10 µg dose adsorbed antigen was diluted 10-fold in water. The vials were incubated at room temperature for 30 min and 2 hours. Group I vials were reconstituted with water for injection.

These microparticle suspensions with 10 µg antigen dose were subsequently subjected to the RP-HPLC-based procedure as described in Malyala et al. (*J. Pharm. Sci.*, 97:1155-1164 (2008)) to determine the % adsorption for each MenB antigen onto the irradiated and non-irradiated microparticles. Specifically, 100 µL of the supernatant was injected on a C4 4.6 mm×150 mm column (Waters) with a Waters 2690/432 instrument (Bedford, Mass.). Linear calibration curves were established in the range of 10-200 µg/mL with Men B protein, and the amount of protein present in the supernatant was calculated. The total amount of unbound protein was then subtracted from the total amount of protein added initially and the difference was used to calculate the actual loading efficiency.

The efficiency of protein adsorption after particle reconstitution was also measured by semi-quantitative SDS-PAGE. Microparticles with adsorbed protein were separated from the adsorption medium by centrifugation and the amount of unbound protein remaining in the supernatant was measured by SDS-PAGE. Essentially, 10 µL of the supernatant corresponding to 10% of total supernatant was loaded. Linear calibration curves were established in the range of 0.5-10 µg/mL with MenB protein, and the amount of protein present in the supernatant was calculated. The total amount of unbound protein was then subtracted from the total amount of protein added initially and the difference was used to calculate the actual loading efficiency ($R^2$ of all standard regression curve were superior to 0.98). The efficiency of protein adsorption on γ-irradiated particles was compared with protein adsorption on the non-irradiated particles.

The 287-953 and 936-741 proteins were observed to adsorb on the microparticles within 30 min at >90% efficiency which was comparable to the protein adsorption after 30 min with the non-irradiated microparticles (Table 3). 961c protein adsorbed on the irradiated microparticles within 30 min at >35%. In comparison, control PLG particles that were incubated overnight resulted in 961c adsorption of >80%.

TABLE 3

EFFICIENCY OF MENB PROTEIN ANTIGENS PLG PARTICLES (% OF TOTAL ANTIGEN)

| Antigen | Untreated | | 15 kGy Irradiation [b] | | 25 kGy Irradiation [b] | |
|---|---|---|---|---|---|---|
| | RG503 | RG505 | RG503 | RG505 | RG503 | RG505 |
| 287-953 | 86.5 [a] (86.5) [b] | 96.6 [a] (>97.5) [b] | >97.5 | >97.5 | >97.5 | >96.0 |
| 936-741 | 88.5 [a] (>97.5) [b] | 92.8 [a] (>97.5) [b] | >97.5 | >97.5 | >97.5 | >97.5 |
| 961c | 95.8 [a] (86.0) [b] | 90.1 [a] (88.5) [b] | 42.0 | 40.0 | 36.0 | 38.0 |

[a] Analyzed by using RP-HPLC on supernatant samples
[b] Estimated by densitometric analysis of SDS-PAGE gels Adsorbed proteins were evaluated for integrity by SDS-PAGE following extraction from microparticles. In this case, proteins were extracted from 1 mg microparticles, with 100 µL of SDS sample buffer, and 10 µL corresponding to 10% of the formulation was loaded on a 4-12% gradient Tris/glycine polyacrylamide gel (Novex, San Diego, Calif.) for SDS-PAGE analysis. The gel was stained with Colloidal blue stain (Novex), destained, and scanned. Antigens desorbed from the irradiated and non-irradiated microparticles were comparable and maintained the antigen structure based on the molecular weights, suggesting that gamma-irradiation of the PLG microparticles has minimal impact on the antigen adsorption efficiency or on the antigen integrity when the antigens are adsorbed post-irradiation. Also, the results demonstrate that the loss in PLG molecular weight does not impair antigen adsorption.

Example 4. ELISA Antibody Titers in Mice

Prior to immunization, three bacterial antigens of a trivalent MenB vaccine (287-953, 961c and 936-741) were independently added with water for injection to vials of gamma-irradiated (Group II) (15 kGy or 25 kGy) and non-irradiated (Group III) microparticle compositions (RG503 or RG505) prepared as described in Example 2, to obtain 4 mg/mL or 40 mg/mL of microparticle concentration, and desired antigen concentrations (1 and 10 µg dosages per 100 µl per antigen, respectively). The vials were incubated at room temperature for 30 min and the contents were subsequently used for animal (CD-1 mice) immunizations. Mice were immunized intramuscularly with 100 µl of injection volume from each vial (corresponding to antigen dosages of 1 or 10 µg per antigen dosage) in groups of 10, three times, at days 0, 21, and 35. Also injected in this fashion was the content of the vials from Group I of Example 2 for each of the 287-953, 961c and 936-741 antigens, after injecting water for injection to obtain 4 and 40 mg/mL microparticle concentrations at total antigen doses per 100 µl of 1 and 10 µg per antigen, respectively. ELISA antibody titers were measured in mice after 2 weeks using the method published previously in Malyala et al. (*J. Pharm. Sci.*, 97, 1155-1164 (2008)).

The results are shown in FIG. 1. (The first and fourth groups of three bars correspond to the results obtained with the Group I microparticles.) The IgG titers are statistically similar for gamma-irradiated and non-irradiated microparticles. These results demonstrate that gamma-irradiation does not have a significant impact on the efficacy of PLG microparticles and that gamma-irradiation followed by antigen adsorption can be used as a viable vaccination strategy.

Example 5. Complement-Mediated Serum Bactericidal Activity in Mice-First Study In a first study, the effect of treatment on the immunogenicity of RG503 PLG polymer was evaluated and the incubation period for protein adsorption (30 min vs. 2 h) was optimized.

Prior to immunization, three bacterial MenB antigens (i.e., 287-953, 961c and 936-741) were independently added with water for injection to vials of gamma-irradiated (Group II) (25 kGy) and non-irradiated (Group III) microparticle compositions (RG503) prepared as described in Example 2, to obtain 4 mg/mL or 40 mg/mL of microparticle concentration, and desired antigen concentrations (1 and 10 μg per antigen dosages per 100 μl, respectively). The vials were incubated at room temperature for 30 min and 2 hours and were subsequently used for animal (CD-1 mice) immunizations.

Mice were immunized intramuscularly in groups of 10, three times, at days 0, 21, and 35. Blood samples were collected at 2 weeks following the third immunization (day 49), sera collected, and Serum Bactericidal Activity (SBA) titers were measured in the mice after 2 weeks for five strains (H44/76, 5/99, M4407, NZ 98/254 and GB364) using the method published previously by Malyala et al. (*J. Pharm Sci.*, 97:1155-1164 (2008)). The SBA assay measures the ability of antibody to fix complement on the surface of the bacterium and trigger bacterial lysis (M. Pizza, et al., *Science* 287: 1816-1820 (2000); R. A. Wall, *Ann Med* 34: 624-634 (2002), and S. S. Wildes et al., *BioDrugs* 16: 321-329 (2002). The extent of SBA was assayed as previously described (M. Pizza, et al., *Science* 287: 1816-1820 (2000)). Sera were analyzed for SBA titers against a panel of *N. meningitides* strains. The assay involves evaluation of pooled mouse sera in dilutions of two-fold. Based on the design of this assay, a two-fold difference between the SBA titers is considered insignificant (e.g., SBA titers of 512 and 1024 are considered as equivalent, as are titers of 1024 and 2048).

The results of these studies are presented in Table 4 to follow and are designated PLG/DSS(non-GI)+MenB-30 min, PLG/DSS (non-GI)+MenB-2 hrs, PLG/DSS(GI)+MenB-30 min, PLG/DSS(GI)+MenB-2 hrs.

Also injected and tested in this fashion was the content of the vials from Group I of Example 2 for each of the 287-953, 961 and 936-741 antigens, after injecting water for injection to obtain 4 and 40 mg/mL microparticle concentrations at total antigen doses per 100 μl injection volume of 1 and 10 μg per antigen, respectively. The results of these studies are also presented in Table 4 to follow and are designated PLG/DSS/MenB STD.

Also injected and tested in this fashion was the three antigen combination adsorbed on aluminum hydroxide (Alum/MenB). Aluminum hydroxide at 3 mg/mL was mixed with 100 μg/mL of each of the three antigens, 10 mM Histidine buffer and 150 mM sodium chloride. Antigens were allowed to adsorb on aluminum hydroxide at 2-8° C. overnight. The Alum/MenB formulation was characterized using SDS-PAGE and mice immunized at 100 μL/dose corresponding to 1 μg and 10 μg of each antigen per dose. The results of these studies are also presented in Table 4 to follow and are designated Alum/MenB.

As can be seen from Table 4, functional bactericidal titers for Men B proteins adsorbed onto non-irradiated PLG microparticles are similar to those adsorbed onto gamma-irradiated PLG microparticles for the higher antigen dose, but at the lower dose some reduction in BCA titers for certain strains is observed with gamma irradiation. The two incubation periods of 30 min and 2 hours resulted in comparable immunogenicity responses. The SBA titers for these formulations were also comparable to alum-adsorbed antigens. Based on these results, 30 min was identified as the optimal incubation period for the adsorption of MenB protein antigens on the PLG particles.

TABLE 4

IN VIVO IMMUNOGENICITY RESPONSE MEASURED AS SBA TITERS TO MENB ANTIGENS.

| Adjuvant Description | Dose | H44/76 | 5/99 | M4407 | NZ 98/254 | GB364 |
|---|---|---|---|---|---|---|
| PLG/DSS/MenB STD | 10 ug | 8192 | 4096 | 1024 | 512 | 1024 |
| PLG/DSS(non-GI) + MenB-30 min | 10 ug | 16384 | 4096 | 1024 | 512 | 2048 |
| PLG/DSS(non-GI) + MenB-2 hrs | 10 ug | 32768 | 2048 | 2048 | 512 | 1024 |
| PLG/DSS(GI) + MenB-30 min | 10 ug | 16384 | 4096 | 2048 | 512 | 2048 |
| PLG/DSS(GI) + MenB-2 hs | 10 ug | 16384 | 1024 | 2048 | 512 | 1024 |
| Alum/MenB | 10 ug | 65536 | 4096 | 2048 | 512 | 2048 |
| PLG/DSS/MenB STD | 1 ug | 8192 | 8192 | 256 | 128 | 2048 |
| PLG/DSS(non-GI) + MenB-30 min | 1 ug | 16384 | 2048 | 1024 | 512 | 512 |
| PLG/DSS(non-GI) + MenB-2 hs | 1 ug | 8192 | 2048 | 1024 | 512 | 512 |
| PLG/DSS(GI) + MenB-30 min | 1 ug | 8192 | 256 | 512 | 128 | 256 |
| PLG/DSS(GI) + MenB-2 hs | 1 ug | 16384 | 256 | 512 | 256 | 128 |
| Alum/MenB | 1 ug | 8192 | 1024 | 256 | 128 | 512 |

Example 6. Complement-Mediated Bactericidal Activity in Mice-Second Study

In a second study RG503 was compared with a higher molecular weight PLG polymer, RG505, using conditions identified in the first study. In order to understand the effect of PLG molecular weight on the PLG formulations, the PLG polymers RG503 (Mw 35 kDa) and RG505 ($M_w$ 69 kDa) (R. Zange et al., *Eur J Pharm Biopharm* 44: 149-157 (1997)), were compared for the effect of gamma-irradiation on the immunogenicity of PLG/MenB formulations.

Prior to immunization, three bacterial MenB antigens (i.e., 287-953, 961c and 936-741) were independently added with water for injection to vials of gamma-irradiated (Group II) microparticle compositions prepared as described in Example 2, to obtain 4 mg/mL or 40 mg/mL of microparticle concentration, and desired antigen concentrations (1 and 10 μg per antigen dosages per 100 μl, respectively). The vials were incubated at room temperature for 30 minutes and were subsequently used for animal (CD-1 mice) immunizations. Each animal was immunized with 100 μl of volume from each vial (corresponding to antigen dosages of 1 or 10 g per antigen dosage) intramuscularly twice at an interval of 4 weeks.

Serum Bactericidal Activity (SBA) titers were measured in the mice after 2 weeks for five strains (H44/76, 5/99, M4407, NZ 98/254 and GB364) using the method published previously in Malyala et al. (*J. Pharm Sci.*, 97:1155-1164 (2008)). The results of these studies are presented in Table 5 to follow and are designated PLG 15 kGy GI 30 min and PLG 25 kGy GI 30 min.

Also injected and tested in this fashion was the content of the vials from Group I of Example 2 for each of the 287-953, 961c and 936-741 antigens, after injecting water for injection to obtain 4 and 40 mg/mL microparticle concentrations at total antigen doses per 100 μl injection volume of 1 and 10 μg per antigen, respectively. The results of these studies are also presented in Table 3 to follow and are designated PLG non-GI overnight.

As can been seen from Table 5, the SBA titers are comparable for the two PLG polymers. While the adsorption of 961c protein on the irradiated particles was inferior to the control particles, SBA titers against the corresponding *N. meningitides* strains (5/99 and GB364) were equivalent between the treated and untreated particles. Similar to the first study, gamma-irradiation did not have an effect on the immunogenicity of the MenB antigens delivered with treated versus control PLG microparticles.

TABLE 5

IN VIVO IMMUNOGENICITY RESPONSE MEASURED AS SBA TITERS TO MENB ANTIGENS.

| Vaccine | PLG | Dose | H44/76 | 5/99 | M4407 | NZ 98/254 | GB364 |
|---|---|---|---|---|---|---|---|
| PLG non-GI overnight | RG503 | 1 ug | 32768 | 512 | 512 | 256 | 512 |
| PLG 15 kGy GI 30 min | RG503 | 1 ug | ≥32768 | 512 | 512 | 256 | 512 |
| PLG 25 kGy GI 30 min | RG503 | 1 ug | ≥32768 | 2048 | 512 | 256 | 256 |
| PLG non-GI overnight | RG505 | 1 ug | 8192 | 2048 | 512 | 256 | 1024 |
| PLG 15 kGy GI 30 min | RG505 | 1 ug | >32768 | 2048 | 4096 | 4096 | 1024 |
| PLG 25 kGy GI 30 min | RG505 | 1 ug | 16384 | 1024 | 512 | 256 | 512 |
| PLG non-GI overnight | RG503 | 10 ug | 16384 | 4096 | 2048 | 512 | 2048 |
| PLG 15 kGy GI 30 min | RG503 | 10 ug | >32768 | 8192 | 1024 | 512 | 512 |
| PLG 25 kGy GI 30 min | RG503 | 10 ug | >32768 | 16384 | 2048 | 512 | 1024 |
| PLG non-GI overnight | RG505 | 10 ug | 8192 | 4096 | 1024 | 512 | 1024 |
| PLG 15 kGy GI 30 min | RG505 | 10 ug | >32768 | 8192 | 1024 | 512 | 4096 |
| PLG 25 kGy GI 30 min | RG505 | 10 ug | >32768 | ≥65536 | 512 | 512 | 4096 |
| Alum/MenB | — | 20 ug | >32768 | 4096 | 256 | 128 | 512 |

Thus, we have developed a two-step approach in which hPLG microparticles are synthesized, lyophilized and gamma-irradiated in a first step. In a second step that occurs prior to immunization, the particles are reconstituted and incubated with sterile antigens to allow surface adsorption of proteins on the microparticles.

The preceding studies demonstrate a scalable strategy for the terminal sterilization of the PLG-based formulations for use as vaccines. The PLG particles can be bulk-lyophilized and bulk-sterilized for use in a commercial vaccine. This strategy for the sterilization of vaccine formulations can overcome the need for aseptic manufacturing thereby reducing the development cost and increasing the ease of manufacturing. In addition, adsorption of antigens prior to immunization allows the sterilized PLG particles to be used for multiple vaccine antigens. This strategy is, in particular, of extensive value for the developing countries and for pandemics where the delivery systems such as PLG microparticles can be stockpiled and maintained in bulk. Furthermore, irradiated particles can be used with a variety of antigens thereby increasing the versatility of the PLG formulations.

Example 7. Preparation of Microparticles (with and without Compound 47)

Compound 47 is prepared as described in Example 44 of WO 2010/144734. Microparticles are prepared using an oil-in-water (o/w) single emulsion technique. Briefly, 4 mL of 15% w/v RG503 PLG (available Boehringer Ingelheim) solution with 6 mg Compound 47, for 1% loading relative to PLG, in dichloromethane is added to 33 mL of water containing 6 mg of dioctyl sulfosuccinate (adjusted to pH 7.2). The mixture is homogenized for one minute at 24,000 rpm using IKA Ultra Turrex T-25 homogenizer followed by homogenization for six minutes at 12,900 rpm using Omni Macro homogenizer. The emulsion is shaken for 3-4 hours at 150 rpm in a ventilated chemical fume hood to evaporate dichloromethane. Microparticles without Compound 47 are synthesized as described above, except that no Compound 47 is added during the microparticle synthesis. All microparticle suspensions are filtered using a 53 micron filter.

Particle size of the microparticles within each resulting suspension is measured using a Horiba LA-930 particle sizer. At this stage (prior to lyophilization), microparticle formulations with a target mean size of 0.5-5 μm are desired.

To determine PLG content, 1 mL of the microparticle suspension is added to pre-weighed scintillation vials and the vials are lyophilized using Labconco bench lyophilizer. PLG content is calculated as the difference between the lyophilized and empty vials. PLG recovery for all PLG formulations is targeted for >70%.

Compound 47 is analyzed by Reversed Phase High Performance Liquid Chromatography (RP-HPLC) using a Waters Acquity System using C18 XTerra column (Waters Corporation) and a gradient of 90% water+0.1% TFA/10% acetonitrile+0.1% TFA to 100% acetonitrile+0.1% TFA in six minutes.

To determine Compound 47 concentration, 100 μL of the particle suspension described above is mixed with 900 μL of DMSO and analyzed by RP-HPLC. Compound 47 recovery is determined based on the Compound 47 concentration in the particle suspension with a target of >75%.

To determine encapsulation efficiency, 100 μL of the microparticle suspension described above is diluted to 1 mL with 10 mM HCl and rocked for 30 minutes at room temperature. The resulting particle suspension is centrifuged. The pellet is then dissolved in 1 mL DMSO and analyzed on the RP-UPLC system to determine the amount of encapsulated Compound 47. The supernatant is also analyzed on the RP-UPLC system to determine the amount of non-encapsulated Compound 47. The amount of Compound 47 encapsulated in microparticles is targeted for >90%.

Example 8. Preparation of Control Microparticle Compositions with Adsorbed Antigen (with and without Compound 47)

MenB antigen 287-953 is adsorbed on the particles at 2-8° C. overnight with 10 mM histidine buffer, pH 5.5, at a 100 μg/mL final concentration of antigen (which ultimately corresponds to 10 μg of antigen per dose). MenB antigen adsorption is conducted on the following micro particle compositions:
Adsorption 1: Compound 47-encapsulated microparticles with 1% Compound 47 loading relative to PLG are provided in an amount that supplies 250 μg/mL Compound 47 for the particles.
Adsorption 2: Microparticles without encapsulated Compound 47 are provided in an amount that yields a PLG content equal to that supplied in Adsorption 1.

MenB antigen adsorption on the microparticles is characterized by SDS-PAGE followed by Coomassie blue staining, and by Experion system (Bio-Rad). See Malyala et al., J. Pharm. Sci. 97:1155-1164 (2008).

Lyophilized formulations are then formed in 6 mL borosilicate glass vials as follows:
Vial 1: The microparticle suspension formed in Adsorption 1 is added to a vial in an amount corresponding to 350 μg Compound 47 (14 doses of 25 μg Compound 47), along with 63 mg mannitol, 21 mg sucrose and 5% w/w PVA relative to PLG, and lyophilized (using a Virtis shelf lyophilizer).
Vial 2: For a co-lyophilized formulation, the microparticle suspension formed in Adsorption 2 (PLG without encapsulated Compound 47) is added to a vial in an amount equal to the same PLG content as in Vial 1, along with the Compound 47 suspension in an amount corresponding to 350 μg of Compound 47, 63 mg mannitol, 21 mg sucrose and 5% w/w PVA relative to PLG, and the contents are lyophilized. Compound 47 suspension is prepared as described in International Patent Application No. PCT/US2010/060621, filed Dec. 15, 2010.
Vial 3: For a control formulation, the microparticle suspension formed in Adsorption 2 (PLG without encapsulated Compound 47) is added to a vial in an amount equal to the same PLG content as in Vial 1, along with 63 mg mannitol and 21 mg sucrose and 5% w/w PVA relative to PLG, and the contents are lyophilized.

Moisture content is determined using the Karl-Fischer titration method and measured with a target of <5% for all lyophilized formulations.

Endosafe PTS system (Charles River Labs) is used for determining the endotoxin content in the lyophilized formulations with a target of <1 EU/dose.

Example 9. Preparation of Irradiated Microparticle Compositions with Adsorbed Antigen (with and without Compound 47)

Microparticles are prepared as described in Example 7. Formulations are formed in 6 mL borosilicate glass vials as follows:

Vial 4: Compound 47-encapsulated microparticles with 1% Compound 47 loading relative to PLG are added to a vial in an amount corresponding to 350 μg Compound 47 (14 doses of 25 jg Compound 47), along with 63 mg mannitol, 21 mg sucrose and 5% w/w PVA relative to PLG, and lyophilized (using a Virtis shelf lyophilizer).
Vial 5: Microparticles without encapsulated Compound 47 are added to a vial in an amount equal to the same PLG content as in Vial 4, along with the Compound 47 suspension in an amount corresponding to 350 μg of Compound 47, 63 mg mannitol, 21 mg sucrose and 5% w/w PVA relative to PLG, and lyophilized (using a Virtis shelf lyophilizer). Compound 47 suspension is prepared as described in International Patent Application No. PCT/US2010/060621, filed Dec. 15, 2010.
Vial 6: Microparticles without encapsulated Compound 47 are added to a vial in an amount equal to the same PLG content as in Vial 4, along with 63 mg mannitol, 21 mg sucrose and 5% w/w PVA relative to PLG, and lyophilized (using a Virtis shelf lyophilizer).

After lyophilization, Vials 4-6 are purged with nitrogen and treated with 25 kGy gamma-irradiation and stored at 2-8° C. MenB antigen 287-953 is added with water for injection at a 100 jg/mL final concentration of antigen (which ultimately corresponds to 10 jg of antigen per dose) to each of the vials of gamma-irradiated microparticle compositions. The vials are incubated at room temperature for 30 minutes to allow protein adsorption.

The microparticle suspensions with 10 μg antigen dose are subsequently subjected to the RP-HPLC-based procedure as described in Malyala et al. (J. Pharm. Sci., 97:1155-1164 (2008)) to determine the % adsorption for MenB antigen onto the irradiated microparticle compositions. Specifically, 100 μL of the supernatant is injected on a C4 4.6 mm×150 mm column (Waters) with a Waters 2690/432 instrument (Bedford, Mass.). Linear calibration curves are established in the range of 10-200 μg/mL with Men B protein, and the amount of protein present in the supernatant is calculated. The total amount of unbound protein is then subtracted from the total amount of protein added initially and the difference is used to calculate the actual loading efficiency.

The efficiency of protein adsorption after particle reconstitution is also measured by semi-quantitative SDS-PAGE. Microparticles with adsorbed protein are separated from the adsorption medium by centrifugation and the amount of unbound protein remaining in the supernatant is measured by SDS-PAGE. Essentially, 10 μL of the supernatant corresponding to 10% of total supernatant is loaded. Linear calibration curves are established in the range of 0.5-10 μg/mL with MenB protein, and the amount of protein present in the supernatant is calculated. The total amount of unbound protein is then subtracted from the total amount of protein added initially and the difference is used to calculate the actual loading efficiency ($R^2$ of all standard regression curve were superior to 0.98). The efficiency of protein adsorption on γ-irradiated particles is compared with protein adsorption on the non-irradiated particles.

Example 10. In Vivo Mouse Study-Bactericidal Assay

The microparticle formulations described in Examples 8 and 9 are reconstituted in 1.4 mL of water for injection with gentle mixing prior to immunizations. Vials 1-3 are ready-to use whereas vials 4-6 are incubated with protein antigen for 30 minutes, as described in Example 9, prior to use (reconstitution). 100 μL of each formulation is injected per mouse, corresponding to 10 μg of MenB antigen and in case of formulations containing Compound 47, 25 μg of the adjuvant. Each mouse is immunized intramuscularly (50 μL at two sites) on days 0 and 21. In some cases, the mice may also be immunized on day 35. Each mouse is bled two weeks after the final immunization.

For mice injected with MenB antigen, pooled sera is analyzed for bactericidal assay against the MenB strain NZ98 two weeks post final immunization.

It will be understood that the invention has been described by way of example only and modifications may be made whilst remaining within the scope and spirit of the invention.

The invention claimed is:

1. A process for preparing a sterile unit dosage form of a blank biodegradable microparticle composition, the process comprising:
   a) preparing a microparticle composition comprising blank biodegradable microparticles that comprise a biodegradable polymer;
   b) lyophilizing the microparticle composition;
   c) loading the microparticle composition into a sealed single dose container; and
   d) sterilizing the microparticle composition by exposing the sealed container to gamma irradiation, wherein the sterile unit dosage form comprises between 4 and 50 mg of said microparticles, and between 5 and 150 mg of one or more pharmaceutical excipients.

2. The process of claim 1, wherein the biodegradable polymer is poly(lactide-co-glycolide).

3. The process of claim 1, further comprising the step of adding a cryoprotective agent to the microparticle composition prior to step (b).

4. The process of claim 3, wherein the cryoprotective agent is selected from the group consisting of mannitol and sucrose.

5. The process of claim 1, further comprising the step of adding an immunological adjuvant to the microparticle composition prior to step (c).

6. The process of claim 5, wherein said immunological adjuvant is selected from monophosphoryl lipid A analogues, small molecule immune potentiators, muramyl tripeptide phosphatidylethanolamine and tocopherols.

7. The process of claim 6, wherein the immunological adjuvant is an activator of a Toll-like receptor (TLR).

8. The process of claim 1, wherein step (c) comprises exposing the sealed container to gamma irradiation at a dose of 15 to 25 kGy.

9. The process of claim 1, wherein the sealed container comprises a septum.

* * * * *